(12) United States Patent
Paz-Rojas et al.

(10) Patent No.: US 9,347,942 B2
(45) Date of Patent: May 24, 2016

(54) ULTRASENSITIVE CELL BASED SENSORS AND USES THEREOF

(75) Inventors: Elier Paz-Rojas, Cordoba (ES); Maria de Gracia Montero-Peñalvo, Cordoba (ES); Veronica Inmaculada Luna-Guerrero, Cordoba (ES); Fe Isabel Garcia Maceira, Cordoba (ES); Jose Andres Morales-Martínez, Cordoba (ES); Tania Garcia Maceira, Cordoba (ES); Ana Belén Aragón-Gómez, Cordoba (ES); Ana Quesada-Molina, Cordoba (ES); Aurora Maria Marquez-Morales, Cordoba (ES)

(73) Assignee: CANVAX BIOTECH SL, Cordoba (ES)

( * ) Notice: Subject to any disclaimer, the term of this patent is extended or adjusted under 35 U.S.C. 154(b) by 446 days.

(21) Appl. No.: 13/811,872

(22) PCT Filed: Jul. 28, 2010

(86) PCT No.: PCT/EP2010/004619
§ 371 (c)(1),
(2), (4) Date: Apr. 23, 2013

(87) PCT Pub. No.: WO2012/013204
PCT Pub. Date: Feb. 2, 2012

(65) Prior Publication Data
US 2013/0203078 A1    Aug. 8, 2013

(51) Int. Cl.
*C12N 5/00*       (2006.01)
*C12N 15/63*      (2006.01)
*G01N 33/566*     (2006.01)
*G01N 33/50*      (2006.01)
*C12N 15/85*      (2006.01)
*C12Q 1/37*       (2006.01)

(52) U.S. Cl.
CPC .............. *G01N 33/566* (2013.01); *C12N 15/85* (2013.01); *C12Q 1/37* (2013.01); *G01N 33/5044* (2013.01)

(58) Field of Classification Search
None
See application file for complete search history.

(56) References Cited

U.S. PATENT DOCUMENTS

2003/0190684 A1    10/2003    Fisher et al.

FOREIGN PATENT DOCUMENTS

WO        WO 0166723        *    3/2001

OTHER PUBLICATIONS

Shiver, John W., et al; "Cytoxicity with Target DNA Breakdown by Rat Basophilic Leukemia Cells Expressing Both Cytolysin and Granzyme A," Cell, Oct. 16, 1992, pp. 315-322, vol. 71.
International Search Report, Mar. 29, 2011.

* cited by examiner

*Primary Examiner* — Michail Belyavskyi
(74) *Attorney, Agent, or Firm* — Tristan A. Fuierer; Moore & Van Allen, PLLC

(57) ABSTRACT

The present invention relates to a novel cell based sensor useful for drug discovery that comprises a cell line with professional regulated exocytosis of secretory granules transfected with a protease as a reporter polypeptide stored in the regulated secretory granules of the cell line with professional regulated exocytosis and having either an endogenous or a heterologous molecule as a modulator of regulated secretory granules exocytosis, such said granule stored protease reporter having at least: a high resistance to conditions already present inside the granules such as low pH and proteolysis by other proteases; enzymatic activity after exocytosis; a highly specific cleavage sequence; a very low level of secretion under unstimulated or basal conditions; and a high signal to background activity in a media compatible with cell culture viability and granule exocytosis for a high throughput robust and sensitive detection.

6 Claims, 5 Drawing Sheets

SEQUENCE LISTING

<160> NUMBER OF SEQ ID NOS: 90

<210> SEQ ID NO 1
<211> LENGTH: 1205
<212> TYPE: DNA
<213> ORGANISM: Artificial Sequence
<220> FEATURE:
<223> OTHER INFORMATION: Synthetic Construct

<400> SEQUENCE: 1

```
ttgctgactt gcgtgaggct ccggtgcccg tcagtgggca gagcgcacat cgcccacagt      60
ccccgagaag ttgggggggag gggtcggcaa ttgaaccggt gcctagagaa ggtggcgcgg     120
ggtaaactgg gaaagtgatg tcgtgtactg gctccgcctt tttcccgagg gtgggggaga     180
accgtatata agtgcagtag tcgccgtgaa cgttcttttt cgcaacgggt ttgccgccag     240
aacacaggta agtgccgtgt gtggttcccg cgggcctggc ctctttacgg gttatggccc     300
ttgcgtgcct tgaattactt ccacgcccct ggctgcagta cgtgattctt gatcccgagc     360
```

```
ttcgggttgg aagtgggtgg gagagttcga ggccttgcgc ttaaggagcc ccttcgcctc      420
gtgcttgagt tgaggcctgg cctgggcgct ggggccgccg cgtgcgaatc tggtggcacc      480
ttcgcgcctg tctcgctgct ttcgataagt ctctagccat ttaaaatttt tgatgacctg      540
ctgcgacgct ttttttctgg caagatagtc ttgtaaatgc gggccaagat ctgcacactg      600
gtatttcggt ttttggggcc gcgggcggcg acggggcccg tgcgtcccag cgcacatgtt      660
cggcgaggcg gggcctgcga gcgcggccac cgagaatcgg acgggggtag tctcaagctg      720
gccggcctgc tctggtgcct ggcctcgcgc cgccgtgtat cgccccgccc tgggcggcaa      780
ggctggcccg tcggcacca gttgcgtgag cggaaagatg gccgcttccc ggccctgctg       840
cagggagctc aaaatggagg acgcggcgct cgggagagcg ggcgggtgag tcacccacac      900
aaaggaaaag gccttttccg tcctcagccg tcgcttcatg tgactccacg gagtaccggg      960
cgccgtccag gcacctcgat tagttctcga gcttttggag tacgtcgtct ttaggttggg      1020
gggaggggtt ttatgcgatg gagtttcccc acactgagtg ggtggagact gaagttaggc      1080
cagcttggca cttgatgtaa ttctccttgg aatttgccct ttttgagttt ggatcttggt      1140
tcattctcaa gcctcagaca gtggttcaaa gttttttct tccatttcag gtgtcgtgct       1200
agctt                                                                  1205

<210> SEQ ID NO 2
<211> LENGTH: 428
<212> TYPE: DNA
<213> ORGANISM: Artificial Sequence
<220> FEATURE:
<223> OTHER INFORMATION: Synthetic Construct

<400> SEQUENCE: 2
cgacctcatg gctgcgcccc gacacccgcc aacacccgct gacgcctgac gggcttgtct       60
gctcccggca tccgcttaca gacaagctgt gaccgtctcc gggagctgca tgtgtcagag      120
gttttcaccg tcatcaccga aacgcgcgag gcagccggat cataatcagc cataccacat      180
ttgtagaggt tttacttgct ttaaaaaacc tcccacacct cccctgaac ctgaaacata       240 aaatgaatgc aattgttgtt gttaacttgt ttattgcagc ttataatggt tacaaataaa      300
gcaatagcat cacaaatttc acaaataaag catttttttc actgcattct agttgtggtt      360
tgtccaaact catcaatgta tcttatcatg tctggatccg gccttgccgg cctcgagcgg      420
ccgctagc                                                               428

<210> SEQ ID NO 3
<211> LENGTH: 479
<212> TYPE: DNA
<213> ORGANISM: Artificial Sequence
<220> FEATURE:
<223> OTHER INFORMATION: Synthetic Construct

<400> SEQUENCE: 3
agtctccaga aaagggggg aatgaaagac cccacctgta ggtttggcaa gctagcttaa        60
gtaacgccat tttgcaaggc atggaaaaat acataactga gaatagagaa gttcagatca      120
aggtcaggaa cagatggaac agctgaatat gggccaaaca ggatatctgt ggtaagcagt      180
tcctgccccg gctcagggcc aagaacagat ggaacagctg aatatggccc aaacaggata      240
tctgtggtaa gcagttcctg ccccggctca gggccaagaa cagatggtcc ccagatgcgg      300
tccagccctc agcagtttct agagaaccat cagatgtttc cagggtgccc caaggacctg      360
```

```
aaatgaccct gtgccttatt tgaactaacc aatcagttcg cttctcgctt ctgttcgcgc    420
gcttctgctc cccgagctca ataaaagagc ccacaacccc tcactcgggg cgccagtcc    479
```

<210> SEQ ID NO 4
<211> LENGTH: 36
<212> TYPE: DNA
<213> ORGANISM: Artificial Sequence
<220> FEATURE:
<223> OTHER INFORMATION: Synthetic Construct

<400> SEQUENCE: 4

```
ctgagcacaa tggccccagg ctccaccgtg ggaaca                              36
```

<210> SEQ ID NO 5
<211> LENGTH: 5348
<212> TYPE: DNA
<213> ORGANISM: Artificial Sequence
<220> FEATURE:
<223> OTHER INFORMATION: Synthetic Construct

<400> SEQUENCE: 5

```
gacggatcgg gagatctccc gatccccTat ggtgcactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgtg atatcgaatt cagtctccag aaaaaggggg    240
gaatgaaaga ccccacctgt aggtttggca agctagctta agtaacgcca ttttgcaagg    300
catgaaaaaa tacataactg agaatagaga agttcagatc aaggtcagga acagatggaa    360
cagctgaata tgggccaaac aggatatctg tggtaagcag ttcctgcccc ggctcagggc    420
caagaacaga tggaacagct gaatatgggc caaacaggat atctgtggta agcagttcct    480
gccccggctc agggccaaga acagatggtc cccagatgcg gtccagccct cagcagtttc    540
tagagaacca tcagatgttt ccagggtgcc ccaaggacct gaaatgaccc tgtgccttat    600
ttgaactaac caatcagttc gcttctcgct tctgttcgcg cgcttctgct ccccgagctc    660
aataaaagag cccacaaccc ctcactcggg gcgccagtcc aagcttggta ccagctcgg    720 atcgatcatg gagacagaca cactcctgct atgggtactg ctgctctggg ttccaggttc    780
caccggtgac gaacaaaaac tcatctcaga agaggatctg ggccatcgc gactgagcac    840 aatggcccca ggctccaccg tgggaacact cgagggatcc gcggccgctc tagagggccc    900
tattctatag tgtcacctaa atgctagagc tcgctgatca gcctcgactg tgccttctag    960
ttgccagcca tctgttgttt gcccctcccc cgtgccttcc ttgaccctgg aaggtgccac    1020
tcccactgtc ctttcctaat aaaatgagga aattgcatcg cattgtctga gtaggtgtca    1080
ttctattctg gggggtgggg tggggcagga cagcaagggg gaggattggg aagacaatag    1140
caggcatgct ggggatgcgg tgggctctat ggcttctgag gcggaaagaa ccagctgggg    1200
ctctaggggg tatccccacg cgccctgtag cggcgcatta agcgcggcgg gtgtggtggt    1260
tacgcgcagc gtgaccgcta cacttgccag cgccctagcg cccgctcctt tcgctttctt    1320
cccttccttt ctcgccacgt tcgccggctt tccccgtcaa gctctaaatc ggggctccc    1380 tttagggttc cgatttagtg ctttacggca cctcgacccc aaaaaacttg attagggtga    1440
tggttcacgt agtgggccat cgccctgata gacggttttt cgccctttga cgttggagtc    1500
cacgttcttt aatagtggac tcttgttcca aactggaaca acactcaacc ctatctcggt    1560
ctattctttt gatttataag ggattttgcc gatttcggcc tattggttaa aaaatgagct    1620
```

```
gatttaacaa aaatttaacg cgaattaatt ctgtggaatg tgtgtcagtt agggtgtgga    1680
aagtccccag gctccccagc aggcagaagt atgcaaagca tgcatctcaa ttagtcagca    1740
accaggtgtg gaaagtcccc aggctcccca gcaggcagaa gtatgcaaag catgcatctc    1800
aattagtcag caaccatagt cccgcccta actccgccca tcccgcccct aactccgccc     1860
agttccgccc attctccgcc ccatggctga ctaattttt ttatttatgc agaggccgag      1920
gccgcctctg cctctgagct attccagaag tagtgaggag gcttttttgg aggcctaggc    1980
ttttgcaaaa agctcccggg agcttgtata tccattttcg gatctgatca agagacagga    2040
tgaggatcgt ttcgcatgat tgaacaagat ggattgcacg caggttctcc ggccgcttgg    2100
gtggagaggc tattcggcta tgactgggca acagacaa tcggctgctc tgatgccgcc      2160
gtgttccggc tgtcagcgca ggggcgcccg gttcttttg tcaagaccga cctgtccggt     2220
gccctgaatg aactgcagga cgaggcagcg cggctatcgt ggctggccac gacgggcgtt    2280
ccttgcgcag ctgtgctcga cgttgtcact gaagcgggaa gggactggct gctattgggc    2340
gaagtgccgg ggcaggatct cctgtcatct caccttgctc ctgccgagaa agtatccatc    2400
atggctgatg caatgcggcg gctgcatacg cttgatccgg ctacctgccc attcgaccac    2460
caagcgaaac atcgcatcga gcgagcacgt actcggatgg aagccggtct tgtcgatcag    2520
gatgatctgg acgaagagca tcaggggctc gcgccagccg aactgttcgc caggctcaag    2580
gcgcgcatgc ccgacggcga ggatctcgtc gtgacccatg gcgatgcctg cttgccgaat    2640
atcatggtgg aaaatggccg cttttctgga ttcatcgact gtggccggct gggtgtggcg    2700
gaccgctatc aggacatagc gttggctacc cgtgatattg ctgaagagct tggcggcgaa    2760
tgggctgacc gcttcctcgt gctttacggt atcgccgctc ccgattcgca gcgcatcgcc    2820
ttctatcgcc ttcttgacga gttcttctga gcgggactct ggggttcgaa atgaccgacc    2880
aagcgacgcc caacctgcca tcacgagatt tcgattccac cgccgccttc tatgaaaggt    2940
tgggcttcgg aatcgttttc cgggacgccg gctggatgat cctccagcgc ggggatctca    3000
tgctggagtt cttcgcccac cccaacttgt ttattgcagc ttataatggt tacaaataaa    3060
gcaatagcat cacaaatttc acaaataaag catttttttc actgcattct agttgtggtt    3120
tgtccaaact catcaatgta tcttatcatg tctgtatacc gtcgacctct agctagagct    3180
tggcgtaatc atggtcatag ctgtttcctg tgtgaaattg ttatccgctc acaattccac    3240
acaacatacg agccggaagc ataaagtgta aagcctgggg tgcctaatga gtgagctaac    3300
tcacattaat tgcgttgcgc tcactgcccg ctttccagtc gggaaacctg tcgtgccagc    3360
tgcattaatg aatcggccaa cgcgcgggga gaggcggttt gcgtattggg cgctcttccg    3420
cttcctcgct cactgactcg ctgcgctcgg tcgttcggct gcggcgagcg gtatcagctc    3480
actcaaaggc ggtaatacgg ttatccacag aatcagggga taacgcagga aagaacatgt    3540
gagcaaaagg ccagcaaaag gccaggaacc gtaaaaaggc cgcgttgctg gcgttttcc     3600 ataggctccg cccccctgac gagcatcaca aaaatcgacg ctcaagtcag aggtggcgaa    3660
acccgacagg actataaaga taccaggcgt ttccccctgg aagctccctc gtgcgctctc    3720
ctgttccgac cctgccgctt accggatacc tgtccgcctt ctcccttcg ggaagcgtgg      3780 cgctttctca tagctcacgc tgtaggtatc tcagttcggt gtaggtcgtt cgctccaagc    3840
tgggctgtgt gcacgaaccc cccgttcagc ccgaccgctg cgccttatcc ggtaactatc    3900
gtcttgagtc aacccggta agacacgact tatcgccact ggcagcagcc actggtaaca     3960
```

```
ggattagcag agcgaggtat gtaggcggtg ctacagagtt cttgaagtgg tggcctaact    4020
acggctacac tagaagaaca gtatttggta tctgcgctct gctgaagcca gttaccttcg    4080
gaaaaagagt tggtagctct tgatccggca acaaaccac cgctggtagc ggttttttg    4140 tttgcaagca gcagattacg cgcagaaaaa aaggatctca agaagatcct ttgatctttt    4200
ctacggggtc tgacgctcag tggaacgaaa actcacgtta agggattttg gtcatgagat    4260
tatcaaaaag gatcttcacc tagatccttt taaattaaaa atgaagtttt aaatcaatct    4320
aaagtatata tgagtaaact tggtctgaca gttaccaatg cttaatcagt gaggcaccta    4380
tctcagcgat ctgtctattt cgttcatcca tagttgcctg actccccgtc gtgtagataa    4440
ctacgatacg ggagggctta ccatctggcc ccagtgctgc aatgataccg cgagacccac    4500
gctcaccggc tccagattta tcagcaataa accagccagc cggaagggcc gagcgcagaa    4560
gtggtcctgc aactttatcc gcctccatcc agtctattaa ttgttgccgg gaagctagag    4620
taagtagttc gccagttaat agtttgcgca acgttgttgc cattgctaca ggcatcgtgg    4680
tgtcacgctc gtcgtttggt atggcttcat tcagctccgg ttcccaacga tcaaggcgag    4740
ttacatgatc ccccatgttg tgcaaaaaag cggttagctc cttcggtcct ccgatcgttg    4800
tcagaagtaa gttggccgca gtgttatcac tcatggttat ggcagcactg cataattctc    4860
ttactgtcat gccatccgta agatgctttt ctgtgactgg tgagtactca accaagtcat    4920
tctgagaata gtgtatgcgg cgaccgagtt gctcttgccc ggcgtcaata cgggataata    4980
ccgcgccaca tagcagaact ttaaaagtgc tcatcattgg aaaacgttct cggggcgaaa    5040
aactctcaag gatcttaccg ctgttgagat ccagttcgat gtaacccact cgtgcaccca    5100
actgatcttc agcatctttt actttcacca gcgtttctgg gtgagcaaaa acaggaaggc    5160
aaaatgccgc aaaaaaggga ataagggcga cacggaaatg ttgaatactc atactcttcc    5220
tttttcaata ttattgaagc atttatcagg gttattgtct catgagcgga tacatatttg    5280
aatgtattta gaaaaataaa caaatagggg ttccgcgcac atttccccga aaagtgccac    5340
ctgacgtc                                                              5348
```

<210> SEQ ID NO 6
<211> LENGTH: 790
<212> TYPE: DNA
<213> ORGANISM: Artificial Sequence
<220> FEATURE:
<223> OTHER INFORMATION: Synthetic Construct

<400> SEQUENCE: 6

```
agatctcccg atccctatg gtgcactctc agtacaatct gctctgatgc cgcatagtta     60
agccagtatc tgctccctgc ttgtgtgttg gaggtcgctg agtagtgcgc gagcaaaatt    120
taagctacaa caaggcaagg cttgaccgac aattgcatga agaatctgct tagggttagg    180
cgttttgcgc tgcttcgcga tgtacgggcc agatatacgc gttgacattg attattgact    240
agagtcatac ctgtttggat ccaaccgggt aggggaggcg cttttcccaa ggcagtctgg    300
agcatgcgct ttagcagccc cgctgggcac ttggcgctac acaagtggcc tctggcctcg    360
cacacattcc acatccaccg gtaggcgcca accggctccg ttctttggtg gcccctttcgc   420 gccaccttct actcctcccc tagtcaggaa gttcccccc gccccgcagc tcgcgtcgtg    480
caggacgtga caaatggaag tagcacgtct cactagtctc gtgcagatgg acagcaccgc    540
tgagcaatgg aagcgggtag gcctttgggg cagcggccaa tagcagcttt gctccttcgc    600
tttctgggct cagaggctgg gaagggggtgg gtccgggggc gggctcaggg gcgggctcag    660
```

```
gggcggggcg gcgcccgaa ggtcctccgg aggcccggca ttctgcacgc ttcaaaagcg    720
cacgtctgcc gcgctgtcct cctcttcctc atctcgggct cgagtaggaa ttatctgcgg    780
cctagctagc                                                           790
```

<210> SEQ ID NO 7
<211> LENGTH: 182
<212> TYPE: DNA
<213> ORGANISM: Artificial Sequence
<220> FEATURE:
<223> OTHER INFORMATION: Synthetic Construct

<400> SEQUENCE: 7

```
ggtgtccccg gaagaaatat atttgcatgt ctttagttct atgatgacac aaaccccgcc     60
cagcgtcttg tcattggcga attcgaacac gcagatgcag tcggggcggc gcggtccgag    120
gtccacttcg catattaagg tgacgcgtgt ggcctcgaac accgagcgac cctgcagcga    180
cc                                                                   182
```

<210> SEQ ID NO 8
<211> LENGTH: 589
<212> TYPE: DNA
<213> ORGANISM: Artificial Sequence
<220> FEATURE:
<223> OTHER INFORMATION: Synthetic Construct

<400> SEQUENCE: 8

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatc               589
```

<210> SEQ ID NO 9
<211> LENGTH: 1092
<212> TYPE: DNA
<213> ORGANISM: Artificial Sequence
<220> FEATURE:
<223> OTHER INFORMATION: Synthetic Construct

<400> SEQUENCE: 9

```
ggatccaccg gtcgccacca tgcaaccgat actcctgctg ctcgcttttc tcctgctccc     60
tcgtgctgac gccggcgaga ttatcggggg acacgaagct aggccacata gcagacccta    120
catggccctg gtgcaatttc tggtcgagga aaagaaacat cggtgcggtg gtgtgctggt    180
ccgccaggat ttcgtcctga ccgcagctca ttgttggggt agctccttca aggtgacact    240
cggtgcccac gacattgaga acaggagac tacacaacag aacttctcag tgaaagcagc    300
tatccctcat ccggatccac cggtcgccac catgcaaccg atactcctgc tgctcgcttt    360
tctcctgctc cctcgtgctg acgccggcga gattatcggg ggacacgaag ctaggccaca    420
```

```
tagcagaccc tacatggccc tggtgcaatt tctggtcgag gaaaagaaac atcggtgcgg    480
tggtgtgctg gtccgccagg atttcgtcct gaccgcagct cattgttggg gtagctcctt    540
caaggtgaca ctcggtgccc acgacattga aaacaggag actacacaac agaacttctc    600
agtgaaagca gctatccctc atccagatta taatcccaag aactacagta atgacattat    660
gctgctgaag ctggagcgaa aagctaagct cacagtcgca gtcaggactc tgagcctgcc    720
tcgggcaaaa gcccaagttc gaccacgaca agtgtgccgg gttgccgggt ggggcagggt    780
gtccctgatg gggtctttta gtgataccct ccaagaggtc gaactgaccg tgcagcaaga    840
ccgggaatgt gagagttatc tgcgcaacta ctataattcc acaactcagc tgtgcgtggg    900
agatcccaag gaaaagaaat ctagttttaa gggcgactcc gggggccctc tggtctgtaa    960
gaacgtgatc cagggaattg tcagttacgg cagaaataac ggtactccac ccagggcttt   1020
tactaaggtg tcaagcttcc tgccctggat caaaaagacc atgaaatctc tgtgatagta   1080
agatctgaat tc                                                       1092
```

<210> SEQ ID NO 10
<211> LENGTH: 767
<212> TYPE: DNA
<213> ORGANISM: Artificial Sequence
<220> FEATURE:
<223> OTHER INFORMATION: Synthetic Construct

<400> SEQUENCE: 10

```
actagttatt aatagtaatc aattacgggg tcattagttc atagcccata tatggagttc     60
cgcgttacat aacttacggt aaatggcccg cctggctgac cgcccaacga ccccccgccca    120 ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct agtattagtc atcgctatta    360
ccatggtgat gcggttttgg cagtacatca atgggcgtgg atagcggttt gactcacggg    420
gatttccaag tctccacccc attgacgtca atggagtttt gttttggcac caaaatcaac    480
gggactttcc aaaatgtcgt aacaactccg ccccattgga cgcaaatggg cggtaggcg    540 tgtacggtgg gaggtctat ataagcagag ctcaataaaa gagcccacaa cccttcactc    600
ggcgcgccag tcctccgatt gactgagtcg cccgggtacc cgtgtatcca ataaaccctc    660
ttgcagttgc atccgacttg tggtctcgct gttccttggg agggtctcct ctgagtgatt    720 gactaccgt cagcgggggt ctttcatttg ggggctcgtc cgggatc                  767
```

<210> SEQ ID NO 11
<211> LENGTH: 249
<212> TYPE: PRT
<213> ORGANISM: Artificial Sequence
<220> FEATURE:
<223> OTHER INFORMATION: Synthetic Construct

<400> SEQUENCE: 11

Ser Gly Ile Ser Leu Asp Asn Ser Tyr Lys Met Asp Tyr Pro Glu Met
1               5                   10                  15

Gly Leu Cys Ile Ile Ile Asn Asn Lys Asn Phe His Lys Ser Thr Gly
            20                  25                  30

Met Thr Ser Arg Ser Gly Thr Asp Val Asp Ala Ala Asn Leu Arg Glu
        35                  40                  45

Thr Phe Arg Asn Leu Lys Tyr Glu Val Arg Asn Lys Asn Asp Leu Thr
 50                  55                  60

Arg Glu Glu Ile Val Glu Leu Met Arg Asp Val Ser Lys Glu Asp His
 65                  70                  75                  80

Ser Lys Arg Ser Ser Phe Val Cys Val Leu Leu Ser His Gly Glu Glu
                 85                  90                  95

Gly Ile Ile Phe Gly Thr Asn Gly Pro Val Asp Leu Lys Lys Ile Thr
                100                 105                 110

Asn Phe Phe Arg Gly Asp Arg Cys Arg Ser Leu Thr Gly Lys Pro Lys
            115                 120                 125

Leu Phe Ile Ile Gln Ala Cys Arg Gly Thr Glu Leu Asp Cys Gly Ile
130                 135                 140

Glu Pro Asp Val Leu Met Glu Asp Met Ala Cys His Lys Ile Pro
145                 150                 155                 160

Val Glu Ala Asp Phe Leu Tyr Ala Tyr Ser Thr Ala Pro Gly Tyr Tyr
                165                 170                 175

Ser Trp Arg Asn Ser Lys Asp Gly Ser Trp Phe Ile Gln Ser Leu Cys
            180                 185                 190

Ala Met Leu Lys Gln Tyr Ala Asp Lys Leu Glu Phe Met His Ile Leu
            195                 200                 205

Thr Arg Val Asn Arg Lys Val Ala Thr Glu Phe Glu Ser Phe Ser Phe
210                 215                 220

Asp Ala Thr Phe His Ala Lys Lys Gln Ile Pro Cys Ile Val Ser Met
225                 230                 235                 240

Leu Thr Lys Glu Leu Tyr Phe Tyr His
                245

<210> SEQ ID NO 12
<211> LENGTH: 1432
<212> TYPE: DNA
<213> ORGANISM: Artificial Sequence
<220> FEATURE:
<223> OTHER INFORMATION: Synthetic Construct

<400> SEQUENCE: 12
ccgcccctct ccctccccccc cccctaacgt tactggccga agccgcttgg aataaggccg      60
gtgtgcgttt gtctatatgt tattttccac catattgccg tcttttggca atgtgagggc     120
ccggaaacct ggccctgtct tcttgacgag cattcctagg ggtctttccc ctctcgccaa     180
aggaatgcaa ggtctgttga atgtcgtgaa ggaagcagtt cctctggaag cttcttgaag     240
acaaacaacg tctgtagcga ccctttgcag gcagcggaac cccccacctg cgacaggtg      300 cctctgcggc caaaagccac gtgtataaga tacacctgca aaggcggcac aaccccagtg     360
ccacgttgtg agttggatag ttgtggaaag agtcaaatgg ctctcctcaa gcgtattcaa     420
caaggggctg aaggatgccc agaaggtacc ccattgtatg ggatctgatc tggggcctcg     480
gtacacatgc tttacatgtg tttagtcgag gttaaaaaaa cgtctaggcc cccgaaacca     540
cggggacgtg gttttccttt gaaaaacacg atgataatat ggccacaacc atgggggcag     600
gtgccaccgg ccgcgccatg gacgggccgc gcctgctgct gttgctgctt ctgggggtgt     660
cccttggagg tgccaaggag gcatgcccca caggcctgta cacacacagc ggtgagtgct     720
gcaaagcctg caacctgggc gagggtgtgg cccagccttg tggagccaac cagaccgtgt     780
gtgagccctg cctggacagc gtgacgttct ccgacgtggt gagcgcgacc gagccgtgca     840
agccgtgcac cgagtgcgtg gggctccaga gcatgtcggc gccgtgcgtg gaggccgacg     900

```
acgccgtgtg ccgctgcgcc tacggctact accaggatga gacgactggg cgctgcgagg    960
cgtgccgcgt gtgcgaggcg ggctcgggcc tcgtgttctc ctgccaggac aagcagaaca   1020
ccgtgtgcga ggagtgcccc gacggcacgt attccgacga ggccaaccac gtggacccgt   1080
gcctgccctg caccgtgtgc gaggacaccg agcgccagct ccgcgagtgc acacgctggg   1140
ccgacgccga gtgcgaggag atccctggcc gttggattac acggtccaca cccccagagg   1200
gctcggacag cacagccccc agcacccagg agcctgaggc acctccagaa caagacctca   1260
tagccagcac ggtggcaggt gtggtgacca cagtgatggg cagctcccag cccgtggtga   1320
cccgaggcac caccgacaac ctcatccctg tctattgctc catcctggct gctgttggtt   1380
gtgggccttg tggcctacat agccttcaag aggtggacag ggggattctc ta           1432
```

<210> SEQ ID NO 13
<211> LENGTH: 33
<212> TYPE: DNA
<213> ORGANISM: Artificial Sequence
<220> FEATURE:
<223> OTHER INFORMATION: Synthetic Construct

<400> SEQUENCE: 13
gttacatatg tctggaatat ccctggacaa cag                                 33

<210> SEQ ID NO 14
<211> LENGTH: 38
<212> TYPE: DNA
<213> ORGANISM: Artificial Sequence
<220> FEATURE:
<223> OTHER INFORMATION: Synthetic Construct

<400> SEQUENCE: 14
gttctgctcg aggtgataga aatagagttc ttttgtga                            38

<210> SEQ ID NO 15
<211> LENGTH: 30
<212> TYPE: DNA
<213> ORGANISM: Artificial Sequence
<220> FEATURE:
<223> OTHER INFORMATION: Synthetic Construct

<400> SEQUENCE: 15
ttttctcgag agcagccaca atgaggaact                                     30

<210> SEQ ID NO 16
<211> LENGTH: 37
<212> TYPE: DNA
<213> ORGANISM: Artificial Sequence
<220> FEATURE:
<223> OTHER INFORMATION: Synthetic Construct

<400> SEQUENCE: 16
gtgcggccgc ttaactgctc ccttgatagt cataatt                             37

<210> SEQ ID NO 17
<211> LENGTH: 31
<212> TYPE: DNA
<213> ORGANISM: Artificial Sequence
<220> FEATURE:
<223> OTHER INFORMATION: Synthetic Construct

<400> SEQUENCE: 17
gatactcgag ggcagccttc ctgagaagat g                                   31

```
<210> SEQ ID NO 18
<211> LENGTH: 38
<212> TYPE: DNA
<213> ORGANISM: Artificial Sequence
<220> FEATURE:
<223> OTHER INFORMATION: Synthetic Construct

<400> SEQUENCE: 18
gttgttgcgg ccgcttagta gcgtttcatg gttttctt                           38

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
ttttctcgag ccttccaggg aagatgaagc t                                  31

<210> SEQ ID NO 20
<211> LENGTH: 37
<212> TYPE: DNA
<213> ORGANISM: Artificial Sequence
<220> FEATURE:
<223> OTHER INFORMATION: Synthetic Construct

<400> SEQUENCE: 20
ttttgcggcc gctagttagc tcttttttcat agttttc                           37

<210> SEQ ID NO 21
<211> LENGTH: 33
<212> TYPE: DNA
<213> ORGANISM: Artificial Sequence
<220> FEATURE:
<223> OTHER INFORMATION: Synthetic Construct

<400> SEQUENCE: 21
gttgttctcg agatgcaacc gatactcctg ctg                                33

<210> SEQ ID NO 22
<211> LENGTH: 39
<212> TYPE: DNA
<213> ORGANISM: Artificial Sequence
<220> FEATURE:
<223> OTHER INFORMATION: Synthetic Construct

<400> SEQUENCE: 22
ttttgcggcc gctcagagag atttcatggt cttttttgat                         39

<210> SEQ ID NO 23
<211> LENGTH: 31
<212> TYPE: DNA
<213> ORGANISM: Artificial Sequence
<220> FEATURE:
<223> OTHER INFORMATION: Synthetic Construct

<400> SEQUENCE: 23
gttactcgag atgaagtcac tgagcctgct c                                  31

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct
```

<400> SEQUENCE: 24
gttgttgcgg ccgcttagtg gcgtttcatg gttttctt             38

<210> SEQ ID NO 25
<211> LENGTH: 36
<212> TYPE: DNA
<213> ORGANISM: Artificial Sequence
<220> FEATURE:
<223> OTHER INFORMATION: Synthetic Construct

<400> SEQUENCE: 25
gttgttctcg agatgcagcc gatcctcctg ctgctc             36

<210> SEQ ID NO 26
<211> LENGTH: 36
<212> TYPE: DNA
<213> ORGANISM: Artificial Sequence
<220> FEATURE:
<223> OTHER INFORMATION: Synthetic Construct

<400> SEQUENCE: 26
ttttgcggcc gctcacacac taccttgacg tttata             36

<210> SEQ ID NO 27
<211> LENGTH: 31
<212> TYPE: DNA
<213> ORGANISM: Artificial Sequence
<220> FEATURE:
<223> OTHER INFORMATION: Synthetic Construct

<400> SEQUENCE: 27
ttatctcgag gagaaaatgc agccattcct c             31

<210> SEQ ID NO 28
<211> LENGTH: 33
<212> TYPE: DNA
<213> ORGANISM: Artificial Sequence
<220> FEATURE:
<223> OTHER INFORMATION: Synthetic Construct

<400> SEQUENCE: 28
ttttgcggcc gcttagaggc gcttcattgt tct             33

<210> SEQ ID NO 29
<211> LENGTH: 35
<212> TYPE: DNA
<213> ORGANISM: Artificial Sequence
<220> FEATURE:
<223> OTHER INFORMATION: Synthetic Construct

<400> SEQUENCE: 29
ttatctcgag aatatgacta agttttcttc ctttt             35

<210> SEQ ID NO 30
<211> LENGTH: 33
<212> TYPE: DNA
<213> ORGANISM: Artificial Sequence
<220> FEATURE:
<223> OTHER INFORMATION: Synthetic Construct

<400> SEQUENCE: 30
ttttgcggcc gcttaatttg tatgaggcgg gac             33

<210> SEQ ID NO 31
<211> LENGTH: 30

```
<212> TYPE: DNA
<213> ORGANISM: Artificial Sequence
<220> FEATURE:
<223> OTHER INFORMATION: Synthetic Construct

<400> SEQUENCE: 31
ttttctcgag agcgccatgg aggcctgcgt                              30

<210> SEQ ID NO 32
<211> LENGTH: 33
<212> TYPE: DNA
<213> ORGANISM: Artificial Sequence
<220> FEATURE:
<223> OTHER INFORMATION: Synthetic Construct

<400> SEQUENCE: 32
ttttgcggcc gccatcaccc cagggcatca ggc                          33

<210> SEQ ID NO 33
<211> LENGTH: 31
<212> TYPE: DNA
<213> ORGANISM: Artificial Sequence
<220> FEATURE:
<223> OTHER INFORMATION: Synthetic Construct

<400> SEQUENCE: 33
ttttctcgag atgcaaccga tactcctgct c                            31

<210> SEQ ID NO 34
<211> LENGTH: 36
<212> TYPE: DNA
<213> ORGANISM: Artificial Sequence
<220> FEATURE:
<223> OTHER INFORMATION: Synthetic Construct

<400> SEQUENCE: 34
ttttgcggcc gcttagcgtt tatcttccag agtttt                       36

<210> SEQ ID NO 35
<211> LENGTH: 32
<212> TYPE: DNA
<213> ORGANISM: Artificial Sequence
<220> FEATURE:
<223> OTHER INFORMATION: Synthetic Construct

<400> SEQUENCE: 35
ttttctcgag tggccccctc tagagcttca at                           32

<210> SEQ ID NO 36
<211> LENGTH: 34
<212> TYPE: DNA
<213> ORGANISM: Artificial Sequence
<220> FEATURE:
<223> OTHER INFORMATION: Synthetic Construct

<400> SEQUENCE: 36
ttttgcggcc gcttggttca atgctgtttt aatt                         34

<210> SEQ ID NO 37
<211> LENGTH: 30
<212> TYPE: DNA
<213> ORGANISM: Artificial Sequence
<220> FEATURE:
<223> OTHER INFORMATION: Synthetic Construct

<400> SEQUENCE: 37
```

-continued gaagctcgag cccaacaaca gcactgctct                           30

<210> SEQ ID NO 38
<211> LENGTH: 37
<212> TYPE: DNA
<213> ORGANISM: Artificial Sequence
<220> FEATURE:
<223> OTHER INFORMATION: Synthetic Construct

<400> SEQUENCE: 38
gatggcggcc gctaactact cagaattttt ctcaatg                   37

<210> SEQ ID NO 39
<211> LENGTH: 29
<212> TYPE: DNA
<213> ORGANISM: Artificial Sequence
<220> FEATURE:
<223> OTHER INFORMATION: Synthetic Construct

<400> SEQUENCE: 39
acgcctcgag ggatccctgc agccggacg                            29

<210> SEQ ID NO 40
<211> LENGTH: 36
<212> TYPE: DNA
<213> ORGANISM: Artificial Sequence
<220> FEATURE:
<223> OTHER INFORMATION: Synthetic Construct

<400> SEQUENCE: 40
ttctgcggcc gctcacacga tccgcttcct gtcccc                    36

<210> SEQ ID NO 41
<211> LENGTH: 29
<212> TYPE: DNA
<213> ORGANISM: Artificial Sequence
<220> FEATURE:
<223> OTHER INFORMATION: Synthetic Construct

<400> SEQUENCE: 41
aactctcgag gggcaaccag ggaacggca                            29

<210> SEQ ID NO 42
<211> LENGTH: 34
<212> TYPE: DNA
<213> ORGANISM: Artificial Sequence
<220> FEATURE:
<223> OTHER INFORMATION: Synthetic Construct

<400> SEQUENCE: 42
ctttgcggcc gcttacagca gtgagtcatt tgta                      34

<210> SEQ ID NO 43
<211> LENGTH: 34
<212> TYPE: DNA
<213> ORGANISM: Artificial Sequence
<220> FEATURE:
<223> OTHER INFORMATION: Synthetic Construct

<400> SEQUENCE: 43
aatagcctcg agattctcaa ctcttctact gaag                      34

<210> SEQ ID NO 44
<211> LENGTH: 35
<212> TYPE: DNA
<213> ORGANISM: Artificial Sequence
<220> FEATURE:
<223> OTHER INFORMATION: Synthetic Construct

<400> SEQUENCE: 44
gatgatgcgg ccgctcactc aacctcaaaa catgg              35

<210> SEQ ID NO 45
<211> LENGTH: 29
<212> TYPE: DNA
<213> ORGANISM: Artificial Sequence
<220> FEATURE:
<223> OTHER INFORMATION: Synthetic Construct

<400> SEQUENCE: 45
ttatctcgag ctcatggcgt ccaccactt                     29

<210> SEQ ID NO 46
<211> LENGTH: 32
<212> TYPE: DNA
<213> ORGANISM: Artificial Sequence
<220> FEATURE:
<223> OTHER INFORMATION: Synthetic Construct

<400> SEQUENCE: 46
tttagcggcc gctcacgatg aagtgtcctt gg                 32

<210> SEQ ID NO 47
<211> LENGTH: 31
<212> TYPE: DNA
<213> ORGANISM: Artificial Sequence
<220> FEATURE:
<223> OTHER INFORMATION: Synthetic Construct

<400> SEQUENCE: 47
gtatctcgag gaccagttcc ctgaatcagt g                  31

<210> SEQ ID NO 48
<211> LENGTH: 33
<212> TYPE: DNA
<213> ORGANISM: Artificial Sequence
<220> FEATURE:
<223> OTHER INFORMATION: Synthetic Construct

<400> SEQUENCE: 48
atcagcggcc gcttcagaga aggagcaatg cat                33

<210> SEQ ID NO 49
<211> LENGTH: 31
<212> TYPE: DNA
<213> ORGANISM: Artificial Sequence
<220> FEATURE:
<223> OTHER INFORMATION: Synthetic Construct

<400> SEQUENCE: 49
gtacctcgag gatgtggttg acagccttct t                  31

<210> SEQ ID NO 50
<211> LENGTH: 35
<212> TYPE: DNA
<213> ORGANISM: Artificial Sequence
<220> FEATURE:
<223> OTHER INFORMATION: Synthetic Construct

<400> SEQUENCE: 50
gttgttgcgg ccgctcactg gggtgggacc gaggc              35

<210> SEQ ID NO 51
<211> LENGTH: 31
<212> TYPE: DNA
<213> ORGANISM: Artificial Sequence
<220> FEATURE:
<223> OTHER INFORMATION: Synthetic Construct

<400> SEQUENCE: 51
ttttctcgag aacacttcag ccccacctgc t                          31

<210> SEQ ID NO 52
<211> LENGTH: 40
<212> TYPE: DNA
<213> ORGANISM: Artificial Sequence
<220> FEATURE:
<223> OTHER INFORMATION: Synthetic Construct

<400> SEQUENCE: 52
ttttgaattc gcggccgctc agcattgacg agagggagtg                 40

<210> SEQ ID NO 53
<211> LENGTH: 34
<212> TYPE: DNA
<213> ORGANISM: Artificial Sequence
<220> FEATURE:
<223> OTHER INFORMATION: Synthetic Construct

<400> SEQUENCE: 53
ctcactcgag aataactcaa caaactcctc taac                       34

<210> SEQ ID NO 54
<211> LENGTH: 36
<212> TYPE: DNA
<213> ORGANISM: Artificial Sequence
<220> FEATURE:
<223> OTHER INFORMATION: Synthetic Construct

<400> SEQUENCE: 54
ttatgcggcc gcttaccttg ttgctcctat gttctt                     36

<210> SEQ ID NO 55
<211> LENGTH: 28
<212> TYPE: DNA
<213> ORGANISM: Artificial Sequence
<220> FEATURE:
<223> OTHER INFORMATION: Synthetic Construct

<400> SEQUENCE: 55
aggtctcgag tccctccagg accagcac                              28

<210> SEQ ID NO 56
<211> LENGTH: 33
<212> TYPE: DNA
<213> ORGANISM: Artificial Sequence
<220> FEATURE:
<223> OTHER INFORMATION: Synthetic Construct

<400> SEQUENCE: 56
ttaagcggcc gctcagactg ctgtggactg ctt                        33

<210> SEQ ID NO 57
<211> LENGTH: 30
<212> TYPE: DNA
<213> ORGANISM: Artificial Sequence
<220> FEATURE:
<223> OTHER INFORMATION: Synthetic Construct

<400> SEQUENCE: 57
ccttctcgag aggactctga acacctctgc                                    30

<210> SEQ ID NO 58
<211> LENGTH: 34
<212> TYPE: DNA
<213> ORGANISM: Artificial Sequence
<220> FEATURE:
<223> OTHER INFORMATION: Synthetic Construct

<400> SEQUENCE: 58
aatagcggcc gcttaggttg ggtgctgacc gttt                              34

<210> SEQ ID NO 59
<211> LENGTH: 32
<212> TYPE: DNA
<213> ORGANISM: Artificial Sequence
<220> FEATURE:
<223> OTHER INFORMATION: Synthetic Construct

<400> SEQUENCE: 59
gttttctcga ggatccactg aatctgtcct gg                                32

<210> SEQ ID NO 60
<211> LENGTH: 33
<212> TYPE: DNA
<213> ORGANISM: Artificial Sequence
<220> FEATURE:
<223> OTHER INFORMATION: Synthetic Construct

<400> SEQUENCE: 60
gtaagcggcc gctcagcagt ggaggatctt cag                               33

<210> SEQ ID NO 61
<211> LENGTH: 28
<212> TYPE: DNA
<213> ORGANISM: Artificial Sequence
<220> FEATURE:
<223> OTHER INFORMATION: Synthetic Construct

<400> SEQUENCE: 61
gatgctcgag gagagaggat tcccgcct                                     28

<210> SEQ ID NO 62
<211> LENGTH: 37
<212> TYPE: DNA
<213> ORGANISM: Artificial Sequence
<220> FEATURE:
<223> OTHER INFORMATION: Synthetic Construct

<400> SEQUENCE: 62
ttttgcggcc gctcaagatg aactgtattt attactg                           37

<210> SEQ ID NO 63
<211> LENGTH: 29
<212> TYPE: DNA
<213> ORGANISM: Artificial Sequence
<220> FEATURE:
<223> OTHER INFORMATION: Synthetic Construct

<400> SEQUENCE: 63
acacctcgag ctggcggtcg ggaacctca                                    29

<210> SEQ ID NO 64

<210> SEQ ID NO 64
<211> LENGTH: 35
<212> TYPE: DNA
<213> ORGANISM: Artificial Sequence
<220> FEATURE:
<223> OTHER INFORMATION: Synthetic Construct

<400> SEQUENCE: 64
cgtagcggcc gctcacacat gatgacaatt ggttg    35

<210> SEQ ID NO 65
<211> LENGTH: 33
<212> TYPE: DNA
<213> ORGANISM: Artificial Sequence
<220> FEATURE:
<223> OTHER INFORMATION: Synthetic Construct

<400> SEQUENCE: 65
ttttctcgag gctctaaatg actgtttcct tct    33

<210> SEQ ID NO 66
<211> LENGTH: 35
<212> TYPE: DNA
<213> ORGANISM: Artificial Sequence
<220> FEATURE:
<223> OTHER INFORMATION: Synthetic Construct

<400> SEQUENCE: 66
ttttgcggcc gcctagacat accgttcgtg acaga    35

<210> SEQ ID NO 67
<211> LENGTH: 31
<212> TYPE: DNA
<213> ORGANISM: Artificial Sequence
<220> FEATURE:
<223> OTHER INFORMATION: Synthetic Construct

<400> SEQUENCE: 67
gtcagtcgac aaacccaaag gccaccctca c    31

<210> SEQ ID NO 68
<211> LENGTH: 34
<212> TYPE: DNA
<213> ORGANISM: Artificial Sequence
<220> FEATURE:
<223> OTHER INFORMATION: Synthetic Construct

<400> SEQUENCE: 68
ttttgcggcc gcctagattg catggttggt gtaa    34

<210> SEQ ID NO 69
<211> LENGTH: 28
<212> TYPE: DNA
<213> ORGANISM: Artificial Sequence
<220> FEATURE:
<223> OTHER INFORMATION: Synthetic Construct

<400> SEQUENCE: 69
ctggctcgag gaaccgggtg ctcagtgc    28

<210> SEQ ID NO 70
<211> LENGTH: 34
<212> TYPE: DNA
<213> ORGANISM: Artificial Sequence
<220> FEATURE:
<223> OTHER INFORMATION: Synthetic Construct

<400> SEQUENCE: 70
ttaggcggcc gctcaacttg tgcacttaaa acgt    34

<210> SEQ ID NO 71
<211> LENGTH: 32
<212> TYPE: DNA
<213> ORGANISM: Artificial Sequence
<220> FEATURE:
<223> OTHER INFORMATION: Synthetic Construct

<400> SEQUENCE: 71
cagcctcgag aatattacag atccacagat gt    32

<210> SEQ ID NO 72
<211> LENGTH: 33
<212> TYPE: DNA
<213> ORGANISM: Artificial Sequence
<220> FEATURE:
<223> OTHER INFORMATION: Synthetic Construct

<400> SEQUENCE: 72
tacagcggcc gctcagaggt tggaagagac att    33

<210> SEQ ID NO 73
<211> LENGTH: 31
<212> TYPE: DNA
<213> ORGANISM: Artificial Sequence
<220> FEATURE:
<223> OTHER INFORMATION: Synthetic Construct

<400> SEQUENCE: 73
agacctcgag gctgtgcagg gatcccagag a    31

<210> SEQ ID NO 74
<211> LENGTH: 34
<212> TYPE: DNA
<213> ORGANISM: Artificial Sequence
<220> FEATURE:
<223> OTHER INFORMATION: Synthetic Construct

<400> SEQUENCE: 74
cactgcggcc gcttcaccag gagcacgtca gcac    34

<210> SEQ ID NO 75
<211> LENGTH: 34
<212> TYPE: DNA
<213> ORGANISM: Artificial Sequence
<220> FEATURE:
<223> OTHER INFORMATION: Synthetic Construct

<400> SEQUENCE: 75
gacggtcgac aattcaacat tattttccca ggtt    34

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
tatcgcggcc gctcagattt tttcattatc atcattg    37

<210> SEQ ID NO 77
<211> LENGTH: 31
<212> TYPE: DNA

<210> SEQ ID NO 77
<211> LENGTH: 31
<212> TYPE: DNA
<213> ORGANISM: Artificial Sequence
<220> FEATURE:
<223> OTHER INFORMATION: Synthetic Construct

<400> SEQUENCE: 77
aatactcgag cctgcagcag aaacctggat a        31

<210> SEQ ID NO 78
<211> LENGTH: 36
<212> TYPE: DNA
<213> ORGANISM: Artificial Sequence
<220> FEATURE:
<223> OTHER INFORMATION: Synthetic Construct

<400> SEQUENCE: 78
atttgcggcc gcggaaatgg aattaagaat attcat        36

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gtcactcgag gacatggcgg atgaaccact c        31

<210> SEQ ID NO 80
<211> LENGTH: 33
<212> TYPE: DNA
<213> ORGANISM: Artificial Sequence
<220> FEATURE:
<223> OTHER INFORMATION: Synthetic Construct

<400> SEQUENCE: 80
tggtgcggcc gctcagatac tggtttggag gtc        33

<210> SEQ ID NO 81
<211> LENGTH: 31
<212> TYPE: DNA
<213> ORGANISM: Artificial Sequence
<220> FEATURE:
<223> OTHER INFORMATION: Synthetic Construct

<400> SEQUENCE: 81
gttatctcga gatggctcac cgtcccccca g        31

<210> SEQ ID NO 82
<211> LENGTH: 34
<212> TYPE: DNA
<213> ORGANISM: Artificial Sequence
<220> FEATURE:
<223> OTHER INFORMATION: Synthetic Construct

<400> SEQUENCE: 82
gttgttgcgg ccgctgtggg aggggcagtt cagg        34

<210> SEQ ID NO 83
<211> LENGTH: 28
<212> TYPE: DNA
<213> ORGANISM: Artificial Sequence
<220> FEATURE:
<223> OTHER INFORMATION: Synthetic Construct

<400> SEQUENCE: 83
ttttctcgag cgaccctcag ggacggcc        28

<210> SEQ ID NO 84
<211> LENGTH: 35
<212> TYPE: DNA
<213> ORGANISM: Artificial Sequence
<220> FEATURE:
<223> OTHER INFORMATION: Synthetic Construct

<400> SEQUENCE: 84
ttttgcggcc gcggtcatgc tccaataaat tcact           35

<210> SEQ ID NO 85
<211> LENGTH: 31
<212> TYPE: DNA
<213> ORGANISM: Artificial Sequence
<220> FEATURE:
<223> OTHER INFORMATION: Synthetic Construct

<400> SEQUENCE: 85
gttactcgag atgctgcttc ttcctctccc c               31

<210> SEQ ID NO 86
<211> LENGTH: 35
<212> TYPE: DNA
<213> ORGANISM: Artificial Sequence
<220> FEATURE:
<223> OTHER INFORMATION: Synthetic Construct

<400> SEQUENCE: 86
gttgttgcgg ccgcttaatt tgcctgcagg atctg           35

<210> SEQ ID NO 87
<211> LENGTH: 31
<212> TYPE: DNA
<213> ORGANISM: Artificial Sequence
<220> FEATURE:
<223> OTHER INFORMATION: Synthetic Construct

<400> SEQUENCE: 87
aaaactcgag ggaaagatgc agccactcct g               31

<210> SEQ ID NO 88
<211> LENGTH: 32
<212> TYPE: DNA
<213> ORGANISM: Artificial Sequence
<220> FEATURE:
<223> OTHER INFORMATION: Synthetic Construct

<400> SEQUENCE: 88
aaaagcggcc gccagtcaca gggggtctc ca               32

<210> SEQ ID NO 89
<211> LENGTH: 32
<212> TYPE: DNA
<213> ORGANISM: Artificial Sequence
<220> FEATURE:
<223> OTHER INFORMATION: Synthetic Construct

<400> SEQUENCE: 89
gatgactcga gatgaccctg ggccgccgac tc              32

<210> SEQ ID NO 90
<211> LENGTH: 33
<212> TYPE: DNA
<213> ORGANISM: Artificial Sequence
<220> FEATURE:

```
<223> OTHER INFORMATION: Synthetic Construct

<400> SEQUENCE: 90
gttgtgcggc cgctcagtgg gtcctgctgg ccg                                    33
```

ULTRASENSITIVE CELL BASED SENSORS AND USES THEREOF

CROSS-REFERENCE TO RELATED APPLICATIONS

This application is filed under the provisions of 35 U.S.C. §371 and claims the priority of International Patent Application No. PCT/EP2010/004619 filed on 28 Jul. 2010 entitled "NOVEL ULTRASENSITIVE CELL BASED SENSORS AND USES THEREOF" in the name of Elier PAZ-ROJAS, et al., which is hereby incorporated by reference herein in its entirety.

FIELD OF THE INVENTION

The present invention relates to a novel cell based sensor useful for drug discovery, diagnostic and determination of analytes that comprises a cell line with professional regulated exocytosis of secretory granules transfected with a protease as a reporter polypeptide stored in the regulated secretory granules of the cell line with professional regulated exocytosis and having either an endogenous or a heterologous molecule as a modulator of regulated secretory granules exocytosis, such said granule stored protease reporter having at least: a high resistance to conditions already present inside the granules such as low pH and proteolysis by other proteases; enzymatic activity after exocytosis; a highly specific cleavage sequence; a very low level of secretion under unstimulated or basal conditions; and a high signal to background activity in a media compatible with cell culture viability and granule exocytosis for a high throughput robust and sensitive detection.

When the cell based sensor is incubated with a specific ligand of the exocytosis modulator the reporter polypeptide is released from granules into the extracellular media and the enzymatic activity of such released reporter polypeptide is detected with a specific substrate' The present invention also allows the development of multiplex assays by mixing in the same reaction vessel at least two cells lines, each with a different pair of exocytosis modulator-granule stored protease reporter and detecting exocytosis with highly specific substrates of each granule stored protease reporter.

Such sensitive cell based sensor is useful for testing interactions between at least two molecules, one acting as the exocytosis modulator and the other as the specific ligand of the exocytosis modulator. Examples of uses of such sensors are: to test interactions between molecules in drug discovery, to quantify molecules such as proteins for diagnostic and for detection of drugs or molecules in several samples for example in the food industry, in environmental samples and in the pharmaceutical industry.

BACKGROUND OF THE INVENTION

The process of discovering a new therapeutic traditionally involves the following stages: (1) identification of a drug target, (2) validation of the target, (3) screening for compounds that affect the activity of the target, (4) testing lead compounds for toxicity, (5) testing lead compounds for side effects, and (6) examining the metabolism and stability of lead compounds, in the patient or in an appropriate model system.

High throughput screening (HTS) is one of the initial stages of the drug discovery process. It allows for testing of hundreds of thousands of chemical compounds per day to select the most prominent candidates for future examination. The compounds are tested against therapeutics targets. Recent developments in modern mass screening are highly influenced by the increasing number of targets identified by genomics and by the expansion of the libraries of compounds synthesized using methods of combinatorial chemistry.

For example, the plasma membrane plays host to more than 20 different families of receptors, including over 1000 different proteins, which have dubbed the receptorome. The G-protein coupled receptor (GPCR) superfamily represents the single largest slice of receptorome, although receptorome also includes toll-like receptors, integrin receptors, low-density lipoprotein receptors, protein tyrosine kinases receptors and phosphatases, cytokine receptors and even some ion channels that function as receptors.

The therapeutic exploitation of the interaction between extracellular and cell surface receptors, which originated as the "drug-receptor" concept, is considered to be one of the great ideas and insights in $20^{th}$-century biomedical science. Because of continuing advances in target identification, screening technologies and target validation, receptorome-based drug discovery efforts are likely to be productive for many decades to come. Not surprisingly, most experts conclude that the receptorome accounts for the largest portion in the druggable genome, with GPCR consistently leading the pack.

One of the first technologies for massive screening is the competition radioligand binding assay that relies on the use of high specific activity radioligands that selectively target the receptor of interest. Competition radioligand binding assays, as typically carried out, provide a reliable estimate of drug affinities for particular molecular targets but do not give information related to efficacy (as either agonist, antagonists or partial agonists). Traditionally, pharmacologists have relied on competition radioligand binding assays to measure ligand affinities and receptor specificities, as well as ascribe physiological relevance to GPCR. Competition radioligand screens are amenable to near—HTS techniques because they can be performed in 96+ well plates, which have been proven invaluable for the efficient screening of focused chemical libraries against an array of receptors. Competition radioligand binding assays are also helpful to link chemical structure with drugs side effects.

Even though radioligand screens are consistent across different cellular expression systems they have several drawbacks that have fueled research on alternative technologies. For example, radioligand assays do not differentiate between agonists, partial agonists, antagonists and inverse agonists. But more importantly, radioligand assays fail to detect responses that occur downstream of ligand binding and as such are not suited to deorphanizing orphan receptors because, by definition, these oGPCR have unknown ligands. Additionally, radioligand-binding assays are, typically, biased for detecting ligand binding to the endogenous receptor site (orthosteric site) and therefore might not detect small molecule modulators that exert their effect at sites distinct form the endogenous site, called allosteric site.

In contrast to radioligand binding assays, functional assays produce information rich ligand profiles that reveal how ligand modulate signal transduction for example in GPCR. Such functional assays rely on the detection of second messengers, which are produced as a result of receptor-specific signal transduction pathways. One of such methods, use the intracellular rise of calcium measured with a calcium sensitive fluorophore as signal while other methods use calcium or cAMP sensitive promoters coupled to reporters like luciferase to measure receptor activation or inhibition. The intracellular rise in calcium is measured with a calcium sensitive dye that increases its fluorescence as intracellular dye binds calcium or by a calcium sensing protein called aequorin that generates a luminescent signal when a coelenterazine derivative is added. But both calcium assays have the following disadvantages: (1) they can not be used to screen for inverse agonist; (2) the short time interval between ligand addition and calcium rise demands highly specialized equipment for simultaneous ligand addition and calcium measurement; and (3) the signal is not amplified. There are many technologies that measure cell or membrane based cAMP accumulation such as SPA™ (GE Healthcare), FlashPlate™ (Perkin Elmer), AlphaScreen™ (Perkin Elmer), HTRF cAMP (Cisbio) and HitHunter™ (DiscoveRx). Reporter gene-based screening technologies are cell-based assays where the increase in second messengers induces the expression of reporter molecules for example luciferase, beta-lactamase, SEAP and beta-galactosidase.

An ideal screening technology should be simple, nonradioactive, with high signal-to-noise ratio, homogeneous, with minimal reagents additions and be amenable to a microtiter plate format to facilitate robotic automation. Another consideration is whether to measure a proximal or distal signaling step. Measurement of events proximal to target activation will reduce the incidence of false positives; however signal-to-noise ratios can be enhanced moving down the signal transduction cascade owing to signal amplification. Another drawback of the use of reporter molecules coupled to second messengers like calcium or cAMP sensitive promoter is that those assays rely on inducible promoters that are usually weak promoters with a high background and that the reporter needs to be measured after transcription and translation either in lysates or as secreted products. The use of methods in which reporter molecules are rapidly secreted to the extracellular medium upon ligand-protein interaction would be desirable in drug discovery screening because it eliminates the cell lysis step to release the intracellular reporter. Also, the use of methods like the measurement of intracellular calcium with specific fluorophores eliminates the need of transcription and new protein synthesis, thus reducing the assay times. This reduction in assay time is very important in methods like homogeneous 3456 nanoplate screening, where the reaction volume is very low thus making reagents evaporation especially relevant. Also, the use of nanoplates for screening demands very sensitive methods for quantifying very small quantities of reporter molecules or second messengers and thus reporter molecules which can be coupled at will with signal amplification cascades are desirable. But as background is also amplified in signal amplification cascades, especially background due to the first steps in the cascade, there is a need of highly specific reporter molecules with the lowest possible signal background. Finally, methods with one or two reagent additions to each well of a nanoplate are preferred in a drug discovery process. Thus, a desirable screening technology should be a mix of: (1) the high sensitivity of reporter based methods; (2) the low false positive rate of second messengers methods; (3) the short assay times of second messengers methods that are transcription-free; (4) the stable signal of protein reporter based methods; (5) the minimal reagents additions or separations of assay products of homogeneous methods; (6) a robust signal with a high signal-to-noise ratio; (7) an amplifiable signal for reducing assay volumes while preserving a high signal-to-noise ratio and (8) a universal readout that could be used for the vast majority of human drugable genome.

Cell with regulated exocytosis of preformed reporters could meet several of the above conditions and thus such cell based sensors could be of high utility in drug discovery and compound characterization. Endogenous beta-hexosaminidase has been the most widely used lysosomal reporter for degranulation but this protein is considered to be a low sensitivity reporter. For example, Tiberghien et al (Tiberghien et al. Journal of Immunological Methods 223_1999.63-75) developed a method in which promyelocytic HL-60 cells were differentiated and employed to set up a 96-well microplate methodology using filtration instead of centrifugation to collect the extracellular fluid together with beta-hexosaminidase as the cell-released enzyme that was enzymatically measured. This method uses non-professional cells that need to be differentiated to induce secretion, both the beta-hexosaminidase reporter and the chemoattractant receptor are endogenous and thus low expressed and all the above combination of factors result in a method that needs at least 250.000 cells per well for screening. Thus, the authors claim that the main advantage of their method is the use of filtration instead of centrifugation to collect the extracellular fluid.

In another assay, Naal R M et al. Biosens Bioelectron 2004 Nov. 1; 20(4):791-6. Naal et al have developed a direct degranulation assay to enable the use of RBL-2H3 mast cells as a biosensor for screening chemical libraries for drug discovery and environmental toxicity evaluation based on the release of endogenous beta-hexosaminidase into the extracellular milieu in a single step. The authors anticipate the use of such method for detecting hapten-IgE interactions and for screening pharmacologic inhibitors of syk tyrosine kinase activity critical for degranulation. Those authors also use endogenous beta-hexosaminidase as reporter and only use the method for detecting hapten-IgE interactions and for screening of pharmacologic inhibitors of tyrosine kinases that participate in degranulation. In addition in this method only adherent cells are used and thus a washing step of each well is needed to eliminate background due to both basal beta-hexosaminidase activity accumulated during the 16 to 24 hours of cell culture before assay and due to beta-hexosaminidase activity normally present in bovine serum used in cell culture media. This washing step of individual wells limits throughput, increases costs and when done in a HTS environment with automatic pipeting robots the signal to background of assays is reduced due to residual volume in the wells containing beta-hexosaminidase activity. Finally as beta hexosaminidase enzyme is expressed by most hemopoyetic cell lines with professional regulated exocytosis, this enzyme allows only the development of monoplex assays and not multiplex assays.

In a third method, Graminski, G F et al (see Graminski G F et al J. Biol. Chem. (1993),268, 8, 5957-5964) have used pigment dispersion in frog melanophores mediated by receptors that activate protein kinase A or protein kinase C to rapidly evaluate chemicals for their effects on receptors that activate PKA or PLC via a functional assay that is used for investigations of ligand-receptor interactions and for massive drug screening. A major drawback of this method is that uses cells of non-mammalian origin for functional evaluation of receptor-ligand interaction and that colorimetric detection is of low sensitivity when compared with fluorescent or chemiluminescent methods.

Other methods have been developed to study intracellular trafficking and secretion of fusion proteins between a lysosomal targeted partner and a fluorescent protein, such as GFP. In a first method, El Meskini, R et al (see El Meskini R et al. Endocrinology 2001, 142-2, 864-873) have used preproneuropeptide Y fusions with GFP to explore routing of the chimeric proteins in AtT-20 cells, PC-12 cells, and primary pituitary cells to yield GFP storage in LDCVs that underwent stimulated release. At 2002, Rajotte (WO2004/016212)

claimed he has developed a technology by fusing RMCP to GFP for detecting and quantifying degranulation but this method is only useful for measuring trafficking but not for quantification because of the low sensitivity of GFP released by the cells.

Other researchers have transfected GPCR into professional secretory cells like RBL-2H3 but endogenous beta-hexosaminidase have been always the reporter used to measure degranulation, only adherent cells has been used for assays and thus an additional washing step is needed to eliminate background thus compromising throughput and this enzyme only allows the development of monoplex assays. Also, promoters and conditions used for expression of surface receptors like GPCR into hemopoyetic cells such as RBL-2H3 need to be carefully optimized to find consistent results. For example, adenosine 3 receptor is considered a GPCR that does not degranulate by itself but potentiates degranulation induced by suboptimal amounts of IgE-allergen. Thus, current state of the art does not teach us how to develop a robust and sensitive sensor based on degranulation suitable for use in HTS.

Until the present invention, there have been no reports on the use of highly specific serine proteases like granzymes A, B, human chymase, proteinase 3 or neutrophil elastase as reporters stored in secretory lysosomes to develop hemopoyetic cell based sensors useful for drug discovery or to detect molecules for diagnostic. Current state of the art employs endogenous beta-hexosaminidase as a reporter by measuring the activity of this enzyme from at least 50.000 cells, a relative large number of cells (see Schwartz et al. J. Immunol. 123: 1445-1450, 1979; and Dragonetti et al. J. Cell Sci. 1 13:3289-3298, 2000) or lysosomal enzymes fused to GFP to track the movement of secretory lysosomes is monitored in real time.

The present invention describes a highly sensitive hemopoyetic cell based sensor based on degranulation of protease reporters useful to test interactions between at least two molecules, with a high signal to background for robust detection, a fast kinetic, with minimal steps amenable for high throughput screening and using sensitive substrates of reporter enzymes for detection of secreted enzymes from a low number of cells to reduce costs. This cell based sensor could be used either in monoplex or multiplex. Multiplex assays have several advantages over monoplex assays for example: an increased throughput, cost reduction without compromising data quality or even improved data quality as every assay has as internal control the other assay made in the same well.

OBJECTS OF INVENTION

Definitions

Transducer is defined as any device that converts a signal from one form to another. For example, the cell based biosensor of the present invention converts a ligand to receptor interaction at the cell surface to a secretion of a reporter polypeptide previously stored inside the cell, thus the measure of the enzymatic activity of the reporter is associated to a ligand-receptor interaction.

Sensor is a type of transducer. Sensors that transduce a biological signal are called biosensors. All living organisms contain biological sensors with functions similar to those of the mechanical sensors. Most of these are specialized cells that are sensitive to: light, motion, temperature, magnetic fields, gravity, humidity, vibration, pressure, electrical fields, sound, and other physical aspects of the external environment; physical aspects of the internal environment, such as stretch, motion of the organism, and position of appendages (proprioception); an enormous array of environmental molecules, including toxins, nutrients, and pheromones; many aspects of the internal metabolic milieu, such as glucose level, oxygen level, or osmolality; and a varied range of internal signal molecules, such as hormones, neurotransmitters, and cytokines. Artificial sensors that mimic biological sensors by using a biological sensitive component, are called biosensors.

Regulated exocytosis, is a process where specialized cells secrete neurotransmitters, hormones, enzymes, peptides or low molecular weight substances (e.g. catecholamines, glutamate, etc). During exocytosis, cell activation generates a chain of intracellular events which lead to the delivery of cargo-containing vesicles to the cell surface membrane (the plasma membrane), culminating in the fusion of a sub-set of these vesicles with specialized regions of the plasma membrane. While a rise in intracellular Ca2+ concentration is often the trigger for exocytosis, other intracellular signals including cAMP, diacylglycerol (DAG), phospholipids, and ATP also regulate or modulate Ca2+-triggered exocytosis.

Secretory granules or secretory vesicles or secretory lysosomes are specialized intracellular organelles that serve as a storage pool for selected secretory products. Secretory granules move towards the periphery of the cell by a stimulus or a modulator, their membranes fuse with the cell membrane, and their content load is released. Although in most cell types, secretory granules appear to represent an entirely new class of organelle, granules in various hemopoyetic cells and certain other cell types share several properties with lysosomes.

Hemopoyetic cell, are cells derived from bone marrow stem cells and comprises all the blood cell types that include both the myeloid (monocytes and macrophages, neutrophils, basophils, eosinophils, erythrocytes, megakaryocytes/platelets and some dendritic cells) and lymphoid lineages (T-cells, B-cells, NK-cells, some dendritic cells).

Cell line with regulated exocytosis: As used herein, the terms "cell with regulated exocytosis," "professional secretory cell line," and "cell line with professional regulated exocytosis" may be used interchangeably. For the methods of the present invention important cell lines are hemopoyetic cell lines with professional regulated exocytosis. All of these terms also include their progeny, which is any and all subsequent generations. It is understood that all progeny may not be identical due to deliberate or inadvertent mutations. Useful cell lines with regulated exocytosis for cell based sensors are host cells generally engineered to express a granule stored reporter that is released into the culture media by a modulator of exocytosis like a cell surface receptor, such as a GPCR after an agonist ligand binding.

Reporter polypeptide or reporter: is a gene that researchers attach to another gene of interest in cell culture, animals or plants. Certain genes are chosen as reporters because the characteristics they confer on organisms expressing them are easily identified and measured, or because they are selectable markers. Reporter genes are generally used to determine whether the gene of interest has been taken up by or expressed in the cell or organism population. Reporter genes herein are polypeptides stored inside secretory granules of professional secretory cell lines like certain hemopoyetic cells and are released into the extracellular media by a stimulus or a modulator of exocytosis.

Protease: Proteins are composed of amino acids as the building blocks where an amide bond is formed between the COOH of one amino acid and the NH2 of the next amino acid to form the peptidic bond. The term protease is synonymous with peptidase, meaning peptide bond hydrolase, and includes endopeptidases and exopeptidases. The ability to catalyze the hydrolysis of the peptide bond at neutral pH and ambient temperatures therefore characterizes proteases, where various catalytic mechanisms are located in a variety of otherwise unrelated protein scaffolds. There are currently six classes of proteases: Serine proteases, Threonine proteases, Cysteine proteases, Aspartic acid proteases (e.g., plasmepsin), Metalloproteases and Glutamic acid proteases. The mechanism used to cleave a peptide bond involves making an amino acid residue that has the cysteine and threonine (peptidases) or a water molecule (aspartic acid, metallo- and glutamic acid peptidases) nucleophilic so that it can attack the peptide carbonyl group. One way to make a nucleophile is by a catalytic triad, where a histidine residue is used to activate serine, cysteine or threonine as a nucleophile. The substrate binding site in all proteases is composed of a fairly large number of amino acid residues that secure proper alignment of the substrates prior to hydrolysis and help promote catalysis through stabilization of the transition state. The binding site is divided into a number of sub-sites each securing a single amino acid residue of the substrate by multiple interactions. In addition to interactions with specific side-chains, binding of the peptide backbone also plays an important role in catalysis. Protease specificity is frequently studied in the context of subsites that flank the catalytic residues and provide the enzyme with specific preferences for peptide or protein substrates. For analysis of protease specificity the nomenclature of Berger and Schechter (see Schechter I, Berger A. Biochem. Biophys. Res. Commun. (1968) 32: 898-902) is used. According to this nomenclature amino acids present in the protease reactive sites are referred to as S4, S3, S2, S1, SV, S2', S3', and they correspond to amino acids present in the substrates with the sequence P4, P3, P2, P1, P1', P2\ P3', where the P1-P1' peptide bond is cleaved. For example, the papain cysteine protease family has well-defined sites from S3 to SV, with some individual proteases having more extended specificity. For example, the granzyme B peptide Ile-Glu-Pro-Asp-Amidomethylcoumarine has Ile as P4, Glu as P3, Pro as P2 and Asp as P1. For several proteases amino acids residues after the cleaved peptide bond, that is Pn' residues, also contribute to specificity. For example mouse granzyme B has a requirement of Glycine at P2 position for efficient cleavage of substrates. Also, a good extended substrate of human granzyme B is Ile-Glu-Pro-Asp-Ser-Gly-Met-Glu (P4-P3-P2-P1-P1

As enzymes, proteases can be kinetically characterized by their substrate affinity, the catalytic rate of the reaction and their substrate specificity or catalytic efficiency. The Michaelis and Menten equation describes the reaction rate and specificity for a simple one-site reaction. Michaelis and Menten divided the process of the conversion of a substrate S into a product P into two steps as shown:

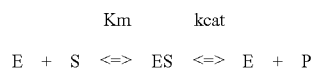

The first reaction step describes the binding of the substrate to the enzyme (catalyst) and the constant $K_m$ corresponds to the dissociation constant of the equilibrium under conditions where the product formation is very slow compared to the dissociation process of the substrate. $K_m$ equals the substrate concentration at half maximal reaction rate $V_{max}/2$. In this case $K_m$ is a good approximation for the dissociation constant and thus describes the affinity of the substrate for the enzyme.

For more complex reactions the constant reflects the dissociation equilibrium of all substrates bound to the enzyme. The second reaction step describes the catalytic rate or the rate of product formation and referred to as the turnover number $k_{cat}$. The turnover rate is defined as the maximal number of product P per active site per unit time. The Michaelis-Menten kinetic is valid only under saturation conditions, that is, when the concentration of substrate S is much larger than the enzyme concentration. Another important property of proteases is their substrate specificity. The ratio $k^{\hat{}}/K_m$ defines a measure of the catalytic efficiency of an enzyme-substrate pair. It refers to the properties and reactions of free enzyme and free substrate. The specificity of an enzyme is therefore a measure of the specificity of an enzyme for competing substrates or of competing enzymes for a single substrate. Proteases are classified as endopeptidases if their cleavage sequence is internal in a target substrate or exopeptidases if they need an amino terminal or a carboxy terminal group for cleavage. Exopeptidases are thus classified into aminopeptidases and carboxypeptidases.

Granules of several hemopoteic cells naturally store proteases like granzymes, mast cell proteases, elastase, proteinase 3, metalloproteases like MMP-8 and MMP-9, serine protease cathepsins like cathepsins A and G and cysteine cathepsins. Granzymes and mast cell proteases belong to the chymotrypsin superfamily of serine proteases because of their high degree of amino acid sequence identity to extensively documented serine proteases; their ability to cleave synthetic serine protease substrates and their inhibition by typical serine protease inhibitors, (see for example Smith M J et al J. Leukoc. Biol. 1996, 60: 555-562). The enzymatic activity of granzymes and mast cell proteases has been classified as tryptase-like (cleavage after Arginine or Lysine), Asp-ase-like (cleavage after Aspartic Acid), chymase-like (cleavage after Phenylalanine, Tryptophan or Tyrosine) and elastase-like (cleavage after Valine, Alanine, Isoleucine, Methionine or Leucine).

Cathepsins are a class of globular proteases, initially described as intracellular peptide hydrolases, although several cathepsins also have extracellular functions. Cathepsins B, C, F, H, L, K, O, S, V, W, and X are cysteine proteases of the papain family, and represent the largest and best-known class of the cathepsins. They primarily function as intracellular proteases mediating terminal nonspecific bulk proteolysis in the acidic environment of lysosomes (see for example Turk V, Turk B and Turk D. EMBO J. 2001; 20:4629-33). Cathepsins A and G are both serine proteases but cathepsin G is an endopeptidase while cathepsin A is a carboxypeptidase. Cathepsins D and E are aspartic proteases. Cathepsins are synthesized as inactive proenzymes and processed to become mature and active enzymes.

Granzymes: Granzymes are structurally related serine proteases that differ in their substrate specificity. They are naturally expressed in cytototxic lymphocytes such as CD8 positive T lymphocytes and natural killers cells but also in testis. To date, five different granzymes have been described in humans: granzymes A, B, H, K and M (see for example Grossman, W J. et al. Curr. Opin. Immunol. (2003) 15, 544-552). In mice, clear orthologues of four of these granzymes (A, B, K and M) can be found, and granzyme C seems the most probable murine orthologue of granzyme H. The murine genome encodes several additional granzymes (D, E, F, G, L and N), of which D, E, F and G are expressed by cytotoxic lymphocytes; L appears to be a pseudogene and N is expressed in the testis.

Modulator of regulated exocytosis, refers to a compound, molecule, or composition that is capable of altering one or more signal transduction pathways downstream involved in regulated exocytosis process. This alteration in activity encompasses inhibition (i.e., the compound, molecule or composition is an "inhibitor" of exocytosis), as well as stimulation, induction or enhancement (i.e., the compound, molecule or composition is a "stimulator", "inductor" or "enhancer" of exocytosis). These modulators are identified using in vitro and/or in vivo assays. In these assays, controls are used in order to permit comparisons between samples.

Drug discovery, process by which drugs are discovered and/or designed. As used herein drug discovery comprises drug identification and modifications for affinity, side effects, bioavailability but also testing the effect of a drug previously launched to the market in a new therapeutic indication, a process also known as reprofiling.

Gene, is the fundamental physical and functional unit of heredity. In biochemical terms, a gene is an ordered sequence of nucleotides located in a particular position on a particular chromosome that encodes a specific functional product (i.e., a protein or RNA molecule). As used herein, a gene is composed not only of coding sequences but can comprise adjacent DNA regions involved in control of the transcription of the coding sequences (e.g., promoters, enhancers) and introns. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Stably introduced" or "stably transformed" or "stably transduced" or "stably transfected" or "stably electroporated", refers to the fraction of cells with the desirable foreign DNA integrated into their genome. Depending upon the expression vector and transfection technique used, only a fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and puromycin. Nucleic acid encoding a selectable marker can be introduced into a host cell on the same vector as that encoding a detectable translation product or can be introduced on a separate vector. Cells stably transfected with the introduced nucleic acid can be identified by drug selection (e.g., cells that have incorporated the selectable marker gene will survive, while the other cells die).

Surface receptor, refers to molecules that occurs on the surface of cells, interact with the extracellular environment and transmit or transduce the information regarding the environment intracellularly in a manner that ultimately modulates transcription of specific promoters, resulting in transcription of specific genes. Examples of surface receptor are tyrosine kinase receptors, ion channel receptors, cytokine receptors, chemokine receptors or a G-protein coupled receptors (GPCRs), such as chemoattractant peptide receptors, neuropeptide receptors, light receptors, neurotransmitter receptors, or polypeptide hormone receptors.

G protein-coupled receptors (GPCRs), also known as seven transmembrane receptors, 7TM receptors, heptahelical receptors, and G protein linked receptors (GPLR), are a large protein family of transmembrane receptors characterized by seven membrane-spanning domains with an extracellular N terminus and a cytoplasmic C terminus. Ligand binding to GPCRs promotes conformational changes leading to small G-protein coupling, the initiation of signal transduction pathways, and ultimately to cellular responses. The ligands that bind and activate these receptors include light-sensitive compounds, odors, pheromones, hormones, and neurotransmitters, and vary in size from small molecules to peptides to large proteins. G protein-coupled receptors are only found in higher eukaryotes, including yeast, plants, and, especially, animals. G protein-coupled receptors are involved in many diseases, but are also the target of around half of all modern medicinal drugs.

GPCRs operate through a similar molecular mechanism. Activation of GPCR by extracellular stimuli causes conformational changes in the receptor, which results in the intermediate coupling and activation of GTP-binding proteins (G proteins). G proteins are heterotrimeric in nature and are composed of alpha (a), beta (β), and gamma (γ) subunits encoded by distinct genes. The alpha subunit is responsible for the binding of GDP and GTP. Binding of a ligand to a GPCR results in a transition of the alpha (α) subunit from a GDP-bound form to a GTP-bound form and leads to the activation of the heterotrimer through dissociation of the a-GTP from the βγ dimer. Both a-GTP and the βγ dimer regulate the activities of a variety of effectors that transmit the signal to the cell interior through the production of second messenger molecules (e.g., calcium, cAMP, etc). There are at least 17 Galpha (Gα) genes, and members of G proteins can be grouped into four main classes termed $G\alpha i/_o$, $G\alpha_{q/11}$, $G\alpha_s$ and $G\alpha_{12/13}$—(see e.g. Preininger A M and Hamm H E. Sci. STKE 2004, re3 and Cabrera-Vera T M et al. Endocr Rev. 2003 December; 24(6):765-81. As used herein, a GPCR comprises receptors coupled to either $G\alpha i/_o$, $G\alpha_{q/11}$, $G\alpha_s$ and $G\alpha_{12/13}$.

Receptor with intrinsic enzymatic tyrosine kinase activity (RTKs), are high affinity cell surface receptors for many polypeptide growth factors, cytokines and hormones. Of the ninety unique tyrosine kinase genes idenitified in the human genome, 58 encode receptor tyrosine kinase proteins. Most RTKs are single subunit receptors but some e.g. the insulin receptor exist as multimeric complexes. Each monomer has a single transmembrane spanning domain, an extracellular N-terminal region and an intracellular C-terminal region. The extracellular N-terminal region is composed of a very large protein domain which binds to extracellular ligands (e.g. a particular growth factor). The intracellular C-terminal region is comprised of regulatory domains and domains responsible for the kinase activity of these receptors, which specifically phosphorylate tyrosine amino acids.

Chimeric receptors, is based of an artificial receptor that combined parts of one receptor with parts of another receptor, protein fragments, tags and any combination thereof, including both entire domains and portions thereof. In general, a chimeric protein or "fusion protein" is a polypeptide comprising at least one portion of the desired protein product fused to at least another peptide sequence or to another polypeptide.

ITAM bearing receptor: An immunoreceptor tyrosine-based activation motif (ITAM) is a conserved sequence of four amino acids that is repeated twice in the cytoplasmic tails of certain cell surface proteins of the immune system. The motif contains a tyrosine separated from a leucine or isoleucine by any two other amino acids, giving the signature YxxL. Two of these signatures are typically separated by between 7 and 12 amino acids in the tail of the molecule (YxxLX$_{(7-12)}$ XxxL). ITAMs are important for signal transduction in certain hemopoyetic cells like immune cells. Thus, they are found in the tails of important cell signaling molecules such as the CD3 and zeta-chains of the T cell receptor complex, the CD79-alpha and -beta chains of the B cell receptor complex, and certain Fc receptors. The tyrosine residues within these motifs become phosphorylated following interaction of the receptor molecules with their ligands and form sites for interaction with other proteins involved in the release of calcium from intracellular stores. Certain chimeric receptors may be developed that comprise the extracellular ligand binding domain of one receptor and at least the transmembrane and intracellular region of an ITAM bearing receptor. Such chimeric receptors induce, upon crosslinking, the release of calcium from intracellular stores.

Antagonist or receptor inhibitor, refers to an agent that down-regulates at least one bioactivity of a protein. An antagonist, used in the broadest sense, includes any molecule that partially or fully blocks, inhibits, or neutralizes a biological activity of a specific tag. An antagonist can also be a compound that down-regulates expression of a gene or which reduces the amount of expressed protein present. They can competitively, noncompetitively, and/or allosterically inhibit one bioactivity of a protein.

Agonist or receptor activator, refers to an agent that mimics, induce or up-regulates (e.g., potentiates or supplements or enhance) the bioactivity of a protein. An agonist can be a wild-type protein or derivative thereof having at least one bioactivity of the wild-type protein. An agonist can also be a compound that up-regulates expression of a gene or which increases at least one bioactivity of a protein. An agonist can also be a compound which increases the interaction of a polypeptide with another molecule, e.g., a target peptide or nucleic acid.

Extracellular signals, include a molecule or a change in the environment that is transduced intracellularly via cell surface proteins that interact, directly or indirectly, with the signal. An extracellular signal or effector molecule includes any compound or substance that in some manner specifically alters the activity of a cell surface protein. Examples of such signals include, but are not limited to, molecules such as acetylcholine, growth factors and hormones, that bind to cell surface and/or intracellular receptors and ion channels and modulate the activity of such receptors and channels. This term also include as yet unidentified substances that modulate the activity of a cellular receptor, and thereby influence intracellular functions. Such extracellular signals are potential pharmacological agents that may be used to treat specific diseases by modulating the activity of specific cell surface receptors.

Orphan receptors, is a designation given to a receptors for which no specific natural ligand has been described.

Signal transduction, is the processing of chemical signals from the cellular environment through the cell membrane, and may occur through one or more of several mechanisms, such as phosphorylation, activation of ion channels, effector enzyme activation via guanine nucleotide binding protein intermediates, formation of inositol phosphate, activation of adenylyl cyclase, and/or direct activation (or inhibition) of a transcriptional factor, etc.

Vector or plasmid vector or plasmid: The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis, et at., Molecular Cloning, A Laboratory Manual (Cold Spring Harbor, 1990) and Ausubel, et al., 1994, Current Protocols In Molecular Biology (John Wiley & Sons, 1996), both incorporated herein by reference).

Expression vector: The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleotide sequences that serve other functions as well and are described below.

Promoter: a "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under the control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 1 10 bp upstream of the start site, although a number of promoters have been shown to contain functional elements downstream of the start site as well. To bring a coding sequence "under the control of a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid molecule, as may be obtained by isolating the 5' non-coding sequences located upstream of the coding segment and/or exon. Such a promoter can be referred to as "endogenous." Similarly, an enhancer may be one naturally associated with a nucleic acid molecule, located either downstream or upstream of that sequence. Alternatively, certain advantages will be gained by positioning the coding nucleic acid segment under the control of a recombinant or heterologous promoter, which refers to a promoter that is not normally associated with a nucleic acid molecule in its natural environment. A recombinant or heterologous enhancer refers also to an enhancer not normally associated with a nucleic acid molecule in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different trahscriptional regulatory regions, and/or mutations that alter expression. The promoter may be heterologous or endogenous.

Poly-A signal or termination signal: The vectors or constructs of the present invention will generally comprise at least one termination signal. A "termination signal" or "terminator" comprises a DNA sequence involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 adenosine residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Signal peptide or a signal sequence: A signal peptide is a short (3-60 amino acids long) peptide chain that directs the post-translational transport of a protein. Signal peptides may also be called targeting signals, signal sequences, transit peptides, or localization signals. The amino acid sequences of signal peptides direct proteins (which are synthesized in the cytosol) to certain organelles such as the nucleus, mitochondrial matrix, endoplasmic reticulum, chloroplast, apoplast and peroxisome. Some signal peptides are cleaved from the protein by signal peptidase after the proteins are transported.

Zymogen or proenzyme: A zymogen (or proenzyme) is an inactive enzyme precursor. A zymogen requires a biochemical change (such as a hydrolysis reaction revealing the active site, or changing the configuration to reveal the active site) for it to become an active enzyme. The biochemical change usually occurs in a lysosome where a specific part of the precursor enzyme is cleaved in order to activate it. The amino acid chain that is released upon activation is called the activation peptide.

Zymogenicity: Zymogenicity or zymogenicity index is the ratio of the activity of a processed enzyme, for example by a protease, to the activity of the zymogen on any given substrate. It is a measure of how effectively the zymogen is constrained, with a large number corresponding to insignificant activity of the zymogen. For example, caspase-3 has a zymogenicity index of about 10.000 while caspase-8 has 100, caspase-9 has 10 and tissue plasminogen activator has 2-10 (see for example Stennicke H R and Salvesen G S. Cell Death and Differentiation (1999) 6, 1054-1059).

Circularly permuted protein: A protein has been circularly permuted if the N and C terminus of the protein has been artificially moved to another position in the protein structure for example by molecular biology techniques. If a protein sequence is readed from the N to the C terminus and represented by ABCDEFGH then a circularly permuted molecule could be DEFGHABC. Thus, circular permutation represents a form of macromolecular isomerization when the normal termini are covalently linked and new termini introduced by breaking the protein backbone elsewhere. Circularly permuted enzymes useful for the methods of the present invention are only enzymes where circular permutation creates a proenzyme or zymogen with a high zymogenicity index devoid of enzymatic activity that could be converted into an active enzyme by a protease cleavage.

Peptide tag: Peptide tags are short peptides that may be used to detect proteins for example with antibodies when specific antibodies to the protein are not available or for protein purification. Examples of known peptide tag that could be used for cell surface detection and separation are c-myc tag, HA tag and FLAG sup™ tag. In general any peptide tag for which is available a specific binding protein could be used for surface detection and or separation provided such specific binding protein is labeled either directly or indirectly with a fluorophore or for example with a bead for surface separation.

Amplification cascade: Coupled enzyme amplification cascades represent a method of enhancing the magnitude of the initial signal to be quantified. These cascades are based into inherent multiplicative property of multienzyme systems, namely, that a product of one of the reactions must be a catalyst or cofactor for a subsequent enzymatic reaction.

The best example of a protease amplification cascade is the blood coagulation cascade where the first protease activates a zymogen to produce an activate protease and this second protease also activates a zymogen to produce a second active protease, thus creating a cascade where the initial signal is amplified up to 1000 fold.

Enzymatic basal activity or zymogen basal activity: The basal activity of an zymogen is defined as the ratio of enzymatic activity in a defined media where no zymogen activator protease has been added, for example, cell culture supernatant or a media compatible with cell culture under unstimulated conditions and enzymatic activity in the same media devoid of zymogen.

Basal secretion: Basal secretion refers to the relative amount of protein secreted by cells in the absence of a modulator of cell exocytosis. In almost all secretory cell types, a level of basal secretion can be detected. It is not known if basal secretion results from release of protein stored into granules or from a fraction of newly synthesized protein that is sorted away from secretory granules, (see for example Burgoyne R D and Morgan A. Physiol Rev (2003) 83: 581-632). For example, in rat parotid acinar cells some secretory proteins are sorted away from secretory granules during their biogenesis to reach constitutive secretory vesicles that account for basal release (see for example, Arvan P and Castle D. Biochem J f1998), 332:593-610) Parotid acinar cells release some amylase via a true constitutive secretion while they also package amylase and other secretory proteins (such as parotid secretory protein, PSP) into conventional secretory granules, which undergo exocytosis in response to an exocytosis modulator. Another example of the relationship between the constitutive or basal secretion versus regulated aspect of exocytosis is demonstrated by the mammary epithelial cell (see Burgoyne R D and Duncan J S. J Mamm Gland Biol Neoplasia, (1998) 3: 275-286). These cells secrete copious amounts of milk constituents including the milk proteins, the caseins, largely by an apparently constitutive route but around one-third of the synthesized casein remains in a stored intracellular pool and can be released in response to Ca2+ elevation in intact cells.

Recombinant DNA (rDNA) molecule, refers to a DNA molecule produced by operatively linking a nucleic acid sequence, such as a gene, to a DNA molecule sequence. Thus, a recombinant DNA molecule is a hybrid DNA molecule comprising at least two nucleotide sequences not normally found together in Nature. Often the introduction of a recombinant DNA that comprises at least a promoter and a DNA coding sequence for a polypeptide not normally found together in Nature are said to be "heterologous" when introduced into an eukaryotic cell. The protein produced by such heterologous or recombinant DNA is also said to be "heterologous". In the context of expressing a heterologous nucleic acid sequence, "host cell" refers to a prokaryotic or eukaryotic cell that is capable of replicating a vector and/or expressing a heterologous gene encoded by a vector. When host cells are "transfected" or "transformed" with nucleic acid molecules, they are referred to as "engineered" or "recombinant" cells or host cells, e.g., a cell into which an exogenous nucleic acid sequence, such as, for example, a vector, has been introduced. Therefore, recombinant cells are distinguishable from naturally-occurring cells which do not contain a recombinantly introduced nucleic acid. Examples of host cells include, but are not limited to, *E. coli* strains that contain the F or F sup.' factor (e.g., DH5 alpha F or DH5 alpha F sup.') or *E. coli* strains that lack the F or F sup.' factor (e.g. DH10B). A host is said to be compatible if it allows replication of the vector or expression of the polypeptides cloned into the vector.

Primer, as used herein refers to an oligonucleotide, whether occurring naturally as in a purified restriction digest or produced synthetically, which is capable of acting as a point of initiation of nucleic acid synthesis when placed under conditions in which synthesis of a primer extension product which is complementary to a nucleic acid strand is induced, (i.e., in the presence of nucleotides and an inducing agent such as DNA polymerase and at a suitable temperature and pH).

PCR, refers to the polymerase chain reaction method of enzymatically amplifying a region of DNA. This exponential amplification procedure is based on repeated cycles of denaturation, oligonucleotide primer annealing, and primer extension by a DNA polymerizing agent such as a thermostable DNA polymerase (e.g. the Taq or Tfl DNA polymerase enzymes isolated from *Thermus aquaticus* or *Thermus flavus*, respectively).

Polylinker or multiple cloning site (MCS) or polycloning, refer to a cluster of restriction enzyme sites on a nucleic acid construct, which are utilized for the insertion, and/or excision of nucleic acid sequences.

Restriction endonucleases or restriction enzymes or endonuclease, refer to enzymes (e.g. bacterial), each of which cut double-stranded DNA at or near a specific nucleotide sequence. Examples include, but are not limited to, AvaII, BamHI, EcoRI, HindIII, Hindi, NcoI, SmaI, and RsaI.

Selective growth media, refers to growth media used to grow cells that has been supplemented with one or more selective agents for example, antibiotics.

Selectable marker or selectable marker sequence or selectable marker gene, refers to a gene, or other DNA fragment, which encodes or provides an activity that confers the ability to grow or survive in what would otherwise be a deleterious environment. For example, a selectable marker may confer resistance to an antibiotic or drug upon the cell in which the selectable marker is expressed. An origin of replication (Ori) may also be used as a selectable marker enabling propagation of a plasmid vector. A selectable marker region, in reference to vector sequence, refers to the portion of a vector component that contains all of the selectable marker sequences present on a particular vector component. In other words, the ends of selectable marker sequences present define the selectable marker region. For example, if a particular vector component only had one selectable marker sequence, the selectable marker region would be defined by the beginning of the selectable marker sequence and the end of the selectable marker sequence. If a particular vector component had, for example, two selectable marker sequences, the selectable marker region is the nucleic acid sequence between the beginning of the first selectable marker sequence and the end of the second selectable marker sequence To clone or cloning when used in reference to an insert sequence and vector means ligation of the insert sequence into a vector capable of replicating in a host. The term "to clone" when used in reference to an insert sequence, a vector, and a host cell refers generally to making copies of a given insert sequence. In this regard, to clone a piece of DNA (e.g., insert sequence), one would insert it into a vector (e.g., a plasmid) which may then be put into a host (usually a bacterium) so that the plasmid and insert replicate with the host. An individual bacterium is grown until visible as a single colony on nutrient media, the colony is picked and grown in liquid culture, and the plasmid containing the "cloned" DNA is re-isolated from the bacteria, at which point there will be many millions of copies of the DNA. The term "clone" can also refer either to a bacterium carrying a cloned DNA, or to the cloned DNA itself.

Transformation or transfection as used herein refers to the introduction of foreign DNA into cells (e.g. prokaryotic or eukaryotic cells). Transformation may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. In particular transfection into eukaryotic cells could be transient when a suitable antibiotic is not included into the cell culture media for selection of cells bearing a stable integration of DNA into the chromosomes. Plasmid vectors for stable selection must have a selectable marker that is expressed into cells that are to be selected with an antibiotic. Although transient transfection could be used in the methods of the present invention preferred cells are those made stable by antibiotic selection.

DETAILED DESCRIPTION OF THE INVENTION

A. Brief Description of the Invention

Figure 1:
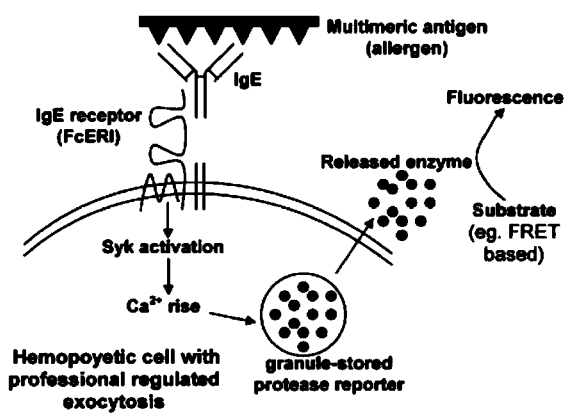
FIG. 1—. Drawing of the general concept of the present invention, using a serine protease as a granule stored reporter, the IgE receptor as the cell surface receptor that modulates granule exocytosis and a FRET based substrate cleaved by secreted granule stored protease reporter for detection. Treatment of cells with a multimeric antigen (for example, an allergen) that binds to high affinity receptor bound IgE induces release of granule stored protease and such protease cleaves the substrate to produce a fluorescent end product. Using this specific substrate of the secreted reporter enzyme, ligand-to-receptor-interation can be determined.
Figure 2:
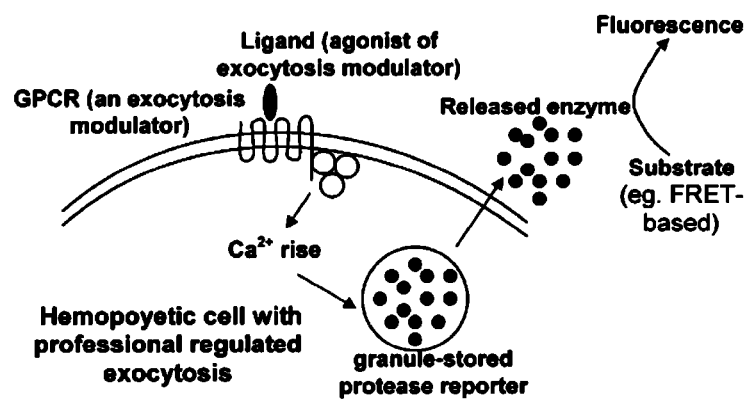
FIG. 2. Drawing of the general concept of the present invention, using a serine protease as a granule stored reporter, a GPCR as the cell surface receptor that modulates granule exocytosis and a FRET based substrate cleaved by secreted granule stored protease reporter for detection. Treatment of cells with an agonist of the GPCR induces release of granule stored protease and such protease cleaves the substrate to produce a fluorescent end product and such protease cleaves the zymogen to produce an active enzyme. Using a specific substrate of the secreted reporter enzyme, ligand-to-receptor-interation can be determined.
Figure 3:
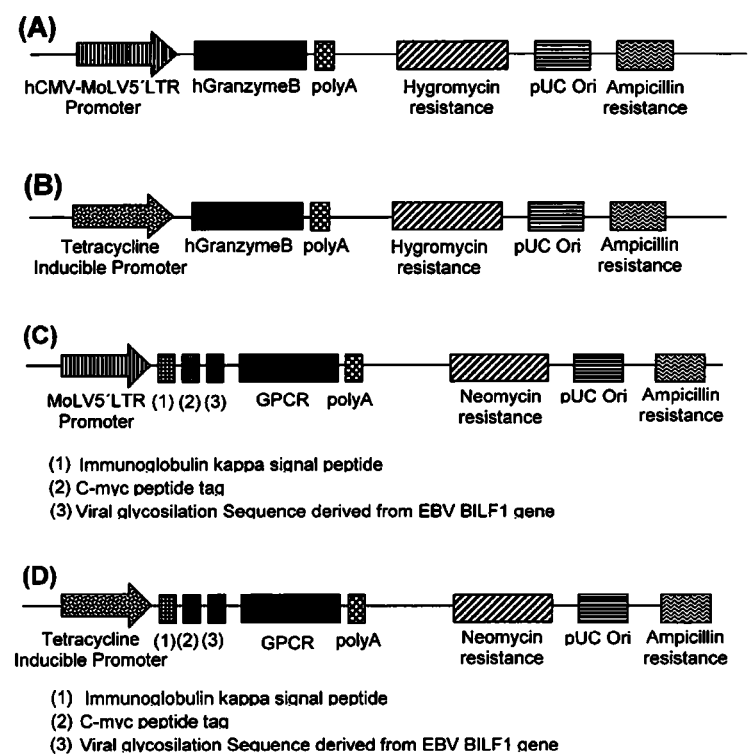
FIG. 3. General structure of representative plasmid vectors of the present invention. Map of the plasmid vector with hygromycin resistance used to stably express granzyme B under the control of a chimeric hCMV-MoMLV5'-LTR strong constitutive promoter (A) or Tetracycline Inducible Promoter (B). Map of the plasmid vector with neomycin resistance used to express a functional surface receptor, such as a GPCR, using the signal peptide of mouse immunoglobulin kappa chain, a c-myc tag for surface detection with anti-cmyc monoclonal antibody and a viral GPCR glycosilation sequence for overexpression under the control of MoMLV5'LTR promoter (C) or under the control of Tetracycline Inducible Promoter (D).
Figure 4:
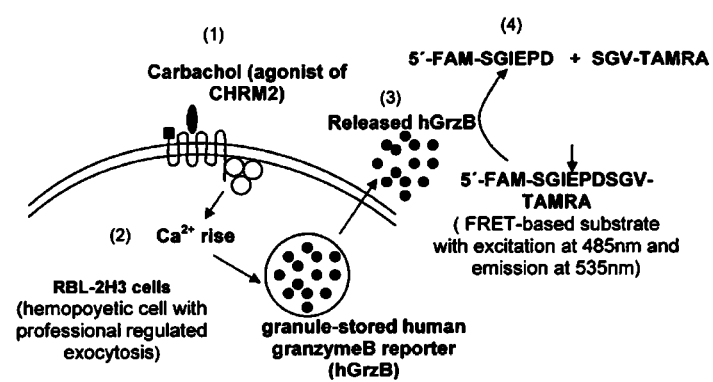
FIG. 4. An example of an assay where the RBL-2H3 cell line is stably transfected with both human granzyme B stored in secretory granules and a N-terminal c-myc tagged human muscarinic type II receptor (CHRM2) under the control of MoMLV5'LTR promoter and comprising a signal peptide and a viral glycosilation sequence for efficient surface expression. (1) Treatment with carbachol (an agonist of CHRM2) induces an increase is intracellular calcium concentration (2) that induces granule release of secreted granzyme B (3) that is detected with 5'FAM-SGIEPDSGV-TAMRA, a FRET based granzyme B substrate (4) using excitation at 485 nm and emission at 535 nm. Increase of fluorescence at 535 nm is proportional to the amount of granzyme B released. Secreted reporters may either be detected directly or the signal amplified by means of a proenzyme like human procaspase-3 for even more sensitive detection of secreted reporter.

The present invention relates to a novel cell based sensor useful for drug discovery, diagnostic and determination of analytes that comprises a cell line with professional regulated exocytosis of secretory granules transfected with a protease as a reporter polypeptide stored in the regulated secretory granules of the cell line with professional regulated exocytosis and having either an endogenous or a heterologous molecule as a modulator of regulated secretory granules exocytosis, such said granule stored protease reporter having at least: a high resistance to conditions already present inside the granules such as low pH and proteolysis by other proteases; enzymatic activity after exocytosis; a highly specific cleavage sequence; a very low level of secretion under unstimulated or basal conditions; and a high signal to background activity in a media compatible with cell culture viability and granule exocytosis for a high throughput robust and sensitive detection.

When the cell based sensor is incubated with a specific ligand of the exocytosis modulator, the reporter polypeptide is released from granules into the extracellular media and the enzymatic activity of such released reporter polypeptide is detected with a specific substrate. The present invention also allows the development of multiplex assays by mixing in the same reaction vessel at least two cells lines, each with a different pair of exocytosis modulator-granule stored protease reporter and detecting exocytosis with highly specific substrates of each granule stored protease reporter.

The cell based sensor of the present invention thus comprises: a hemopoyetic cell line with professional regulated exocytosis; a granule stored protease reporter transfected into such said hemopoyetic cell line and such granule stored reporter under the control of a suitable promoter; an exocytosis modulator for example a surface receptor like a GPCR under the control of a suitable promoter and a specific substrate for detection of the secreted granule stored protease reporter.

Such sensitive cell based sensor is useful for testing interactions between at least two molecules, one acting as the exocytosis modulator and the other as the specific ligand of the exocytosis modulator. Examples of uses of such sensors are: to test interactions between molecules in drug discovery, to quantify molecules such as proteins for diagnostic and for detection of drugs or molecules in several samples for example in the food industry, in environmental samples and in the pharmaceutical industry.

The sensor of the present invention is sensitive and thus uses a lower amount of cells than currently available sensors, response is faster than sensors based into inducible promoters, no lysis is needed for release of reporters, signal can be measured either in end-point mode or in kinetic mode, all reagents can be mixed and then read, no washing or stop steps are needed thus increasing throughput, a high signal to background is obtained for a robust assay and even signal amplification steps are possible for even more sensitive detection. The sensor of the present invention also allows the development of multiplex assays by mixing in the same reaction vessel at least two cells lines, each with a different pair of exocytosis modulator-granule stored protease reporter and detecting exocytosis with highly specific substrates of each granule stored protease reporter. Such multiplex assays reduce the cost per assay and improve signal quality as each assay has the other assay made in the same well as internal control.

B. Detailed Description of the Invention

This invention is best understood by description of relevant properties of each component of the sensor that is, of cells with professional regulated exocytosis, granule stored protease reporters, exocytosis modulators, promoters and conditions for expression of both granule stored protease reporters and exocytosis modulators and detection systems.

B.1. Useful Cells for the Methods of the Present Invention.

The present invention relates to a novel cell based sensor useful for drug discovery, diagnostic and determination of analytes that comprises a cell line with professional regulated exocytosis of secretory granules transfected with a protease as a reporter polypeptide stored in the regulated secretory granules of the cell line with professional regulated exocytosis and having either an endogenous or a heterologous molecule as a modulator of regulated secretory granules exocytosis, such said granule stored protease reporter having at least: a high resistance to conditions already present inside the granules such as low pH and proteolysis by other proteases; enzymatic activity after exocytosis; a highly specific cleavage sequence; a very low level of secretion under unstimulated or basal conditions; and a high signal to background activity in a media compatible with cell culture viability and granule exocytosis for a high throughput robust and sensitive detection.

Secretory granules and their regulated exocytosis are well known in the state of the art and have been most extensively studied in a few cell types chosen either as model systems due to certain experimental advantages or due to their crucial physiological or pathophysiological interest (see for example, Burgoyne, R D and Morgan, A. Physiological Reviews, Vol. 83, No. 2, April 2003, pp. 581-632). Probably the most studied cell types have been the adrenal chromaffin cell (and its tumor counterpart the PC12 cell line), the pancreatic beta-cell and hemopoietic cells like mast cells, platelets and neutrophils but secretory granule exocytosis also occurs, however, in many different neuroendocrine and endocrine cell types for the secretion of peptides and other hormones and in exocrine cells for the secretion of digestive enzymes. Moreover it has been demonstrated that even in non-professional secretory cell lines such as fibroblastoid cell lines (CHO cells) a Ca2+-regulated pathway for exocytosis exist and this probably all cell types might possess a regulated exocytotic pathway, that is, conventional lysosomes can be triggered by Ca2+ to undergo exocytosis. But secretory lysosomes are a distinct class of regulated secretory organelle and this exocytic capacity clearly marks them from conventional lysosomes. Although conventional lysosomes can also fuse with the plasma membrane and release their soluble contents following stimulation (1), the extent of Ca2+-triggered secretion of lysosomal enzymes from cells such as fibroblasts and epithelial cells tends to be only 10-20% (2). In comparison, up to 80% of lysosomal markers are released upon a physiological trigger from cells that possess secretory lysosomes, called herein, cells with professional regulated exocytosis. Thus, preferred cells for the methods of the present invention are selected from a group comprising cells with professional regulated exocytosis. One of the most diverse groups of cells with professional regulated exocytosis is that comprising hemopoyetic cells like neutrophils, basophils, eosinophils, T-cells such as cytotoxic T lymphocytes and Natural Killer cells (NK cells). Central to the normal function of all the above cells is regulated exocytosis of vast amounts of stored components like proteases such as granzymes, mast cell proteases, cathepsins and other hydrolytic enzymes like glycosidases. Thus, hemopoyetic cells with professional regulated exocytosis are highly relevant cells for the methods of the present invention.

In one embodiment of the present invention the cells are selected from a group of hemopoyetic cell lines with professional regulated exocytosis selected from cells such as cytotoxic T lymphocytes, neutrophils, mast cells, and basophils that use their secretory lysosomes to store specialized components such as serine proteases like granzymes, cathepsins, mast cell proteases, neutrophil elastases and proteinases in addition to their usual lysosomal content that comprises several hydrolases like glycosidases and melanin, histamine, and serotonin.

In another embodiment of the present invention preferred cells are selected from RBL-2H3, a rat basophilic leukemia cell line, mouse 32D cell line, a mouse bone marrow hemopoyetic cell, human NK92 cell line, a natural killer cell line and human YT cell line, a natural killer cell line and mouse MC/9 cell line, a mouse mast cell. Particularly preferred cell line for the methods of the present invention is RBL-2H3 because this cell line has a very low constitutive secretion level and highly induced secretion of preferred reporters of the present invention like granzymes that renders a sensor with a high signal to background.

B.2. Exocytosis Modulators

The present invention also comprises exocytosis modulators. In one embodiment of the present invention exocytosis modulators are selected from compounds or polypeptides that induce a change i the level of intracellular calcium. In another embodiment of the invention exocytosis modulators are selected from compounds or polypeptides that induce a change in the levels of cAMP, diacylglycerol (DAG), phospholipids, or ATP that in turn regulate or modulate calcium triggered exocytosis.

One important class of exocytosis modulators are surface receptors that comprises G-protein coupled receptors (GPCR), receptors with instrinsic tyrosine kinase activity, receptors with associated tyrosine kinase activity and receptors bearing an ITAM motif like endogenous or heterologous Fc gamma and epsilon receptors or receptors bearing an ITIM motif normally involved in antigen recognition and present in many hemopoyetic cell receptors.

Thus, in an embodiment of the present invention exocytosis modulators may be surface receptors that upon ligand binding provoke exocytosis of the reporters stored inside the granules of cells with regulated exocytosis. Such exocytosis modulators could be either endogenous exocytosis modulators like the high affinity IgE receptor also known as Fc receptor epsilon I or transfected homologous or heterologous exocytosis modulators like GPCRs or Fc gamma receptors or Fc epsilon I receptors. In another embodiment of the invention exocytosis modulators may be surface receptors that upon ligand binding inhibit exocytosis of reporters induced by ligand binding to another receptor. In a further embodiment exocytosis modulators may comprise chimeric receptors with an extracellular region for ligand binding and a transmembrane and intracellular region for signal transduction for example, a chimeric receptor between extracellular region of interleukin-2 receptor that comprises the IL-2 binding region and at least the transmembrane and intracellular region of rat Fc epsilon receptor I that comprises ITAM sequences and other sequences needed for signal transduction.

In one embodiment cell surface receptors are selected from G-protein coupled receptors (GPCRs), receptors with intrinsic or associated tyrosine kinase activity and ITAM containing receptors that upon specific ligand binding provoke exocytosis of granule stored reporters.

GPCRs are classified according the signal they transduce into four main types: Galpha-$i/o$, Galpha-$q/11$, Galpha-$s$ and Galpha-$12/13$. coupled receptors. Alpha-s coupled GPCRs increase cyclic-AMP inside cells while alpha-i/o coupled GPCRs block the increase in cyclic-AMP inside cells. Alpha-q coupled GPCRs increase intracellular calcium and alpha-12/13 produce an activation of the cytosolic small GTPase, Rho. But it is well known in the state of the art that hemopoyetic cells have promiscous alpha-15/16 chains that couple alpha-s, alpha-12/13 and alpha-i/o coupled GPCRs to an increase in intracellular calcium and the present invention benefits from this fact. In one embodiment of the present invention GPCRs which can be used for reporter exocytosis from granules may be selected from alpha-q/11, or alpha-12/13 or alpha-i/o or alpha-s coupled GPCRs. GPCRs selected as exocytosis modulators in the methods of the present invention may be either full length receptors or receptors where the C-terminal tail has been partially or completely deleted.

It is known that upon ligand binding some GPCR induce the release of beta-hexosaminidase, but according to the state of the art this seems to be a property of only certain GPCR. For example, adenosine 3 receptor has been reported that does not induce degranulation by itself, but potentiates degranulation induced by suboptimal doses of IgE and antigen. Degranulation has been demonstrated mainly in chemokine receptors and certain alpha-i coupled GPCR endogenously expressed in mast cells and basophils such as RBL-2H3 cells. Also, granule exocytosis has been demonstrated in muscarinic type I and type III acetylcholine receptor, both alpha-q coupled GPCR, overexpressed in RBL-2H3 cells. But there is controversy about the pathway leading to degranulation. For example, Barlic et al reported that IL8RA (CXC1 R) alpha-i coupled GPCR devoid of the C-terminal end was unable to degranulate in RBL-2H3 and even attributed such loss of degranulation to serine residues that phosphorylate and bind arrestins upon interleukin-8 interaction. Others investigators questioned such results providing evidence that a C-terminal truncated IL8RA (CXC1 R) is even more effective in degranulation than the natural receptor probably because of a lower rate of internalization after ligand binding. All the above results used beta-hexosaminidase as reporter and the CMV promoter, an extremely weak promoter for most GPCR in cells like RBL-2H3 and partially silenced in hemopoyetic cells like RBL-2H3.

During experimentation we have found that human adenosine 3 receptor (ADORA3) when cloned into a suitable vector such as those described in the methods of the present invention is an extremely potent exocytosis modulator those questioning previous state of the art based mainly in GPCRs expressed under the control of hCMV promoter that is extremely[1] low in cells like RBL2H3 for most GPCRs and is silenced over time in those cells for certain GPCRs that are expressed under hCMV promoter control. Also previous vector did not use any sequence to aid GPCR surface expression. All the above differences make our sensor highly sensitive and thus useful in drug discovery.

Another important consideration for a usefull cell based sensor is the expression level of the target to be modulated by a ligand. Targets like surface receptors, for example, are expressed on the cell surface in amounts form less than 1000 molecules per cell to more than 500.000 molecules per cell and thus there is a variation of up to 1000 fold in the expression level of target molecules. GPCR, the main class of surface receptors, are expressed at generally low levels and only about 10% of GPCR have a signal peptide at the N-terminal end, while the vast majority uses the first transmembrane domain as a signal to translocation to the membrane, probably aided by certain chaperones for surface expression. In general, a higher expression level of the target will result in a higher sensitivity of the sensor and thus, the search for conditions for overexpression of protein targets, especially surface receptors, is desired.

The present invention also comprises promoters and sequences useful for G-protein coupled receptors expression at the surface of useful cells for the methods of the invention. In one embodiment suitable promoters for constitutive GPCR expression may be selected from a group comprising human or mouse elongation factor 1-alpha promoters (SEQ ID NO: 1), human phosphoglycerate kinase (SEQ ID NO: 6), Rous Sarcoma Virus (RSV) promoter (SEQ ID NO:2) and 5'LTR from Moloney Murine Leukaemia Virus promoter MoMLV-5'LTR (SEQ ID NO:3). Such promoters are not silenced over time in the hemopoyetic cells used in the methods of the present invention.

In one embodiment of the present invention suitable promoters for surface expression of GPCR are inducible promoters. In a further embodiment inducible promoters for GPCR expression on cell surface may be selected from a group comprising tetracycline inducible promoter, ecdysone inducible promoter, cumate inducible promoter and progesterone inducible promoter.

In another embodiment GPCRs may comprise a signal peptide for surface overexpression and a tag for surface detection and/or separation of positive cells for example by flow cytometry or by magnetic beads. For example, Andersson, H et al (see Andersson et al Mol Pharmacol (2003) 64:570-577) have demonstrated that the addition of a signal peptide at the N terminus of CB1 or shortening of the long N-tail greatly enhances the stability and cell surface expression of the receptor without affecting receptor binding to a cannabinoid ligand.

In another embodiment the vector useful for GPCR expression may comprise a glycosilation sequence for surface overexpression. Such glycosilation sequence should be inserted between the tag and the first amino acid of the natural GPCR sequence. In a further preferred embodiment the glycosilation sequence is the natural glycosilation sequence selected from a viral GPCR that comprises the sequence SEQ ID NO:4. One example of a useful vector for constitutive GPCR expression is P-MoMLV-5'LTR-SP-cmyc-tag-VGS-MCS-polyA (SEQ ID NO:5) that comprises a promoter that is not silenced in hemopoyetic cells, a signal peptide to aid in translocation across the membrane, a tag for selection of cells with the GPCR on surface, a glycosilation signal to improve membrane expression and a polyadenilation sequence to stabilize messenger RNA. If the sequence of the P-MoMLV5'LTR promoter in the vector of sequence SEQ ID NO:5 is replaced by tetracycline inducible promoter then a vector suitable for inducible GPCR expression is obtained. The present invention is the first to demonstrate that the addition of a glycosilation signal at the N-terminal end of a GPCR, in particular, a glycosilation signal derived from a viral GPCR, improve cell surface receptor expression.

B.3. Granule Stored Reporters

The most widely used reporter for granule secretion is endogenous beta-hexosaminidase but this protein has been traditionally considered a low sensitivity reporter with a low signal to background ratio. In addition, this glycosidase can not be coupled to a signal amplification cascade as for example proteases, which can be coupled into proteolytic cascades for initial signal amplification, similar to blood coagulation cascades where the signal is amplified several fold by a cascade of enzymes with a zymogen as substrate, that results in blood coagulation. Moreover, as beta-hexosaminidase is normally present in granules of most hemopoyetic cells with professional regulated exocytosis, this protein does not allow the development of multiplex assays. Thus the search for other granule stored reporters for the development of a sensitive measurement of degranulation is warranted.

Sorting of soluble proteins between the constitutive and the regulated pathways is clearly complex, and there is substantial evidence for cell-type specificity in the routing of soluble proteins to storage granules, regardless of the level of expression. For example, amylase is a normal granule constituent in exocrine pancreatic cells, and is trafficked to granules when transfected into exocrine pancreatic cell lines but is constitutively secreted in transfected endocrine cell lines (see for example, El Meskini, R et al. Endocrinology (2001) Vol. 142, No. 2 864-873). Cell type specificity may explain some of the contradictory results using portions of the amino terminal of the POMC molecule to study routing in various endocrine and neuronal cell lines (see for example, Tarn W W H et al. Eur J Cell Biol (1993), 62:294-306; Roy P et al. Mol Cell Endocrinol (1991), 82:237-250 and Cool D R et al. J Biol Chem (1995) 270:8723-8729. Cell specificity of protein sorting extends beyond cell lines to primary cultures, as the same constructs can be handled quite differently in primary endocrine and neuronal cells. Thus, for those skilled in the art, other cells different than hemopoyetic cells with regulated exocytosis could be used in the methods of the present invention but the selection of other cell types need to be made in parallel with a specific reporter stored at high concentration in the secretory granules of the selected cell line and with a low level of basal secretion.

One important property of a reporter to be useful in the methods of the present invention stored in secretion granules, especially in secretion granules of cells of hemopoyetic origin, is the resistance to the harsh environment this reporter most withstand inside the granules. Secretion granules of hemopoyectic cells are related with lysosomes, organelles that store inside a vast pool of hydrolases such as cathepsins, tryptases and chymases at a very acidic pH and this environment is not ideal for a protein not naturally stored in such organelles, thus a protease or a pH labile reporter will probably be degraded inside secretory granules thus lowering the sensitivity of such labile reporter protein. For example, proteases are the major protein constituent exocytosed from activated mast cells (see for example Huang et al, J Clin Immunol. 18:169-183, 1998). Tryptases, chymases, and carboxypeptidases are the three major families of proteases stored in the secretory granules of mast cells. Thus, preferred reporters of the present invention are polypeptides with a high resistance to proteolysis and low pH inside the granules of the hemopoyetic cells of the present invention. Although the coexistence of lysosomal enzymes and hematopoyetic serine proteases with several antibiotic proteins in secretory lysosomes indicates that co-storage is possible without degradation not every polypeptide artificially directed to secretory granules will resist this harsh environment. For example, Kaur J and Cutler D F (see Kaur, J and Cutler D F. J. Biol. Chem., (2002) Vol. 277, Issue 12, 10498-10505) have found that a chimeric HRP-Pselectin can be targeted to both secretory and conventional lysosomes but up to 70% of targeted protein was proteolytically degraded.

Secretory granules of hemopoyetic cells used in the methods of the present invention share properties with lysosomes which are organelles that store inside a vast pool of hydrolases such as cathepsins, tryptases and chymases at a very acidic pH environment and thus useful reporters for the methods of the present invention must be polypeptides resistant to the environment inside granules of suitable hemopoyetic cells.

In one embodiment of the present invention useful reporters are selected from polypeptides resistant to the environment inside the granules of hemopoyetic cells, such as proteolysis and low pH. In a further embodiment of the present invention granule stored protease reporters are selected from a group of serine proteases naturally stored in the granules of hemopoyetic cells that comprises enzymes with Asp-ase like activity with cleavage after aspartic acid, enzymes with chymase-like activity with cleavage after phenylalanine, tryptophan and tyrosine, enzymes with tryptase-like activity with cleavage after lysine or arginine and enzymes with elastase-like activity with cleavage after valine, alanine, isoleucine, methionine, leucine or cysteine. In a still further embodiment preferred serine proteases are enzymes with endopeptidase activity selected from a group comprising granzymes, cathepsin G, neutrophil elastase and proteinase 3 and mast cell proteases like chymase.

Granules of hemopoyetic cells also store cathepsins that belong to the papain family of cysteine proteases. Cathepsins are a class of globular proteases, initially described as intracellular peptide hydrolases, although several cathepsins also have extracellular functions. Cathepsins B, C, F, H, L, K, O, S, V, W, and X are cysteine proteases of the papain family, and represent the largest and best-known class of the cathepsins. They primarily function as intracellular proteases mediating terminal nonspecific bulk proteolysis in the acidic environment of lysosomes (see for example Turk V, Turk B and Turk D. EMBO J. 2001; 20:4629-33). Cathepsins A and G are both serine proteases but cathepsin G is an endopeptidase while cathepsin A is a carboxypeptidase. Cathepsins D and E are aspartic proteases. Cathepsins are synthesized as inactive proenzymes and processed to become mature and active enzymes. Because of the function of cysteine cathepsins as intracellular proteases in the acidic environment of lysosomes their optimal pH is around 5 to 5.5 and at the physiological pH needed for cell culture viability and exocytosis in the methods of the present invention their catalytic efficiency is not the optimal. For this reason serine proteases are in general preferred reporters for granule storage in the methods of the present invention when compared with cysteine cathepsins. It is also known in the state of the art that other degrading proteases including metalloproteases are stored into granules and released from hemopoyetic cells such as neutrophils, for example MMP-8 (neutrophil collagenase) and MMP-9 (92 kDa gelatinase) (see for example, Owen C A and Campbell E J. J. Leukoc. Biol. (1999) 65, 137-150). But serine proteases of hemopoyetic cells have the greatest contribution to the proteolytic activity released from preferred cells in the methods of the present invention and thus serine proteases are preferred over metalloproteases and cysteine cathepsins. This greater contribution to proteolytic activity is the result of both greater granule concentration of serine proteases and greater catalytic activity of serine proteases at neutral pH over other proteases that are also stored into granules.

In one embodiment of the present invention DNA coding for reporters could be transfected either to produce a zymogen protein or to produce an active enzyme. Granule reporters synthesized as zymogens are targeted to secretory granules where they are activated while active enzymes are targeted to secretory granules and they do not need activation. For example, granzymes are zymogens that become activated by cathepsin C inside the granules by cleavage at the N-terminal activation dipeptide to produce an active enzyme.

Eventhough constitutive active granzyme B is correctly targeted and stored inside the granules and thus, is useful for the methods of the present invention, such constitutive active granzyme B has a higher basal activity than granzyme B synthesized as a zymogen, thus lowering the signal to background of the sensor. Other investigators have demonstrated (see Isaaz et al. Eur J Immunol 1995; 25(4): 1071-9) that in CD8+ cytotoxic T lymphocyte (CTL) clones during active synthesis, an important amount of granzymes is constitutively secreted and up to one third of granzymes A and B can be secreted directly from the CTL via the constitutive secretory pathway as shown by granzyme A enzymatic activity and immunoblots of secreted granzyme B, where one third of the protein fails to acquire the granule targeting signal. Constitutive secretion of the lytic proteins can be blocked by both CHX and brefeldin A (BFA). While BFA does not affect the directional killing of recognized targets, it abrogates bystander killing, indicating that bystander killing arises from newly synthesized lytic proteins delivered via a non-granule route. Thus, the use of a zymogen that needs to be activated inside granules instead of a constitutive active reporter reduces basal activity and a cell line with a higher signal to background ratio is produced for a more robust sensor useful for the methods of the present invention.

In another embodiment of the present invention useful reporters for the methods of the present invention may be either naturally occurring sequences or codon optimized reporters for high expression in useful cell lines. For example the codon optimized sequence of horse granzyme B is shown as SEQ ID NO:9.

B.4. Promoters for Reporter Expression.

This invention also comprises suitable promoters for expression of reporters. Useful promoters for expression of granule stored reporters of the present invention are promoters suitable for protein expression in hemopoyetic cells, in particular promoters suitable for medium to high protein expression. A promoter with medium protein expression produces more than 10 ng of granule stored granzyme B per million of RBL-2H3 cells while a strong promoter produces more than 100 ng of granule stored granzyme B per million of RBL-2H3 cells when quantified by a specific ELISA (enzyme linked immunosorbent assay). Another relevant property of suitable promoters is that protein expression must be stable during culture. Certain heterologous promoters are down-regulated during culture especially in hemopoyetic cells and this process is called "promoter silencing". Preferred promoters for the methods of the present invention are thus non-silenciable promoters.

In one embodiment of the present invention promoters for reporter expression are selected from a group comprising: a chimeric promoter of hCMV and MoMLV-5'-LTR promoter of SEQ ID NO: 10; MoMLV-5'LTR promoter (SEQ ID NO:3); Elongation Factor 1-alpha promoter (SEQ ID NO:1); RSV promoter (SEQ ID NO:2) and thymidine kinase promoter (SEQ ID NO:7). Other promoters such as human cytomegalovirus promoter, one of the strongest promoters widely used for transfection of eukaryotic cells, is also suitable but in the hemopoyetic cells of the present invention it produces at least 125 times lower granzyme B than a vector with granzyme B under the control of a chimeric hCMV-5'LTR of MoMLV, thus reducing sensor sensitivity. Thus, a vector using granzyme B as a reporter is useful for promoter evaluation to select suitable promoters for reporter expression for the methods of the present invention. In general, preferred promoters for reporter expression in the methods of the present invention are such promoters from which more reporter is produced, that is stronger promoters are preferred than weaker promoters.

In another embodiment of the present invention preferred promoters are those that are not silenced by cells during subculture. Promoter silencing limits the usefulness of a promoter and we have discovered that human CMV (hCMV) promoter is partially silenced in at least one of the preferred cell lines of the present invention, that is, in RBL-2H3. But a chimeric promoter composed also of hCMV fused to 5'-LTR of MoMLV is not silenced in more than 6 months of continuous culture. Promoter silencing must be determined experimentally and for those skilled in the art a vector in which for example human granzyme B is expressed under the control of a promoter to be tested and having an antibiotic resistance for stable selection in mammalian cell lines is useful for cloning of novel promoter and to select stable cell lines that can be cultured by several months to select strong promoters that are not silenced and thus are useful for the methods of the present invention.

In one embodiment of the present invention promoters for expression of granule stored protease reporters are inducible promoters. In a further embodiment inducible promoters for expression of granule stored protease reporters may be selected from a group comprising tetracycline inducible promoter, ecdysone inducible promoter, cumate inducible promoter and progesterone inducible promoter.

B.5. Detection Technologies and Substrates.

Besides resistance to environment inside secretory granules, high level expression, low basal secretion and high induced secretion of a reporter to be useful in the methods of the present invention, other important properties of reporters for regulated exocytosis for the sensitive detection methods of the present invention is type of detection technology used to measure the secreted reporter and the catalytic efficiency of such reporter for the specific substrate used for detection. Both highly sensitive detection technologies and a reporter with a high catalytic efficiency for a specific substrate are beneficial for the methods of the present invention.

Useful reporters for the methods of the present invention are enzymes with proteolytic activity and thus, proteolytic activity detection technologies are of capital importance for the present invention. In one embodiment of the present invention the method used to measure the enzymatic activity of secreted granule stored reporters are selected from a colorimetric, a fluorescent, a FRET, a time resolved-FRET or a luminescent method.

Such methods are well known in the state of the art. For example, human granzyme B activity could be detected by the use of a peptide IEPD C-terminally coupled to p-nitroanilide (pNA) by colorimetric detection at 405 nm, the same peptide C-terminally coupled to 7-amido-4-methylcoumarin could be detected by fluorescence with excitation at 380 nm and emission wavelengths of 460 nm and the same peptide C-terminally coupled to 7-amido-trifluoromethylcoumarin could be detected by fluorescence with excitation at 400 nm and emission at 505 nm.

Especially relevant for the methods of the present invention are highly sensitive fluorescent or luminescent protease substrates, for example, FRET-based protease substrates, luminescent-based protease substrates and rhodamine-110 based fluorescent substrates.

In another embodiment of the present invention the method used to measure the enzymatic activity of useful reporters like granzymes A, B, chymase, proteinase 3 or neutrophil elastase is selected from a Forster resonance energy transfer (FRET) or a time resolved-FRET method. Forster resonance energy transfer or FRET is a technique that detects proximity between two fluorophores that can serve as a FRET pair. For example, if the fluorescence emission spectrum of one fluorophore called the "donor" overlaps with the excitation spectrum of the other fluorophore called the "acceptor", then the two molecules can function as a FRET pair. When in proximity to one another, typically within 100 angstroms or less, excitation of the donor fluorophore leads to non-radiative energy transfer to the acceptor fluorophore, resulting in an increase in fluorescence emission from the acceptor, and a decrease in fluorescence emission from the donor. When the FRET partners are separated, FRET is eliminated. The EDANS/DABCYL fluorophore-quencher pair is one of the most commonly used for FRET applications, owing to excellent spectral overlap between the emission spectrum of EDANS (excitation wavelength 341 nm, emission wavelength 471 nm) and absorbance spectrum of DABCYL (absorbance wavelength maxima 453 nm). Quenching of the fluorescence of EDANS by DABCYL is consequently highly efficient, with up to 40-fold enhancements in fluorescence having been observed upon proteolysis of DABCYL/EDANS labeled peptides. For example, a peptide with the sequence SGIEPDSGV could be labeled with EDANS as a "donor" fluorophore at N-terminal and DABCYL at the C-terminal as an "acceptor" or quencher. When this intact peptide substrate is used for measurement of the enzyme activity, the fluorescence of EDANS is quenched by DABCYL. Upon the cleavage of the FRET peptide by for example human granzyme B, the fluorescence of EDANS is recovered, and can be continuously monitored at excitation/emission=340 nm/470 nm. Increase in EDANS fluorescence is correlated to granzyme B activity. 5'-FAM/TAMRA FRET pair is also widely used for labeling protease substrates, is more sensitive than DABCYL/EDANS based peptides and 5-FAM/TAMRA based FRET substrates are less interfered by autofluorescence of test compounds due to its longer emission wavelength. Also there are many FRET pairs that could be useful for the methods of the present invention. For example, Biosearch Technologies has developed highly efficient quenchers marketed under the trademark BHQsup.T or Blackhole quenchers, while Anaspec has developed QXLsup™ quenchers and Perkin Elmer QSYsup® quenchers. For a quencher-fluorophore pair to be efficient the emission fluorescence spectra of the fluorophore must overlap with the absorbance spectra of the quencher. Another relevant property of FRET pair to be useful for the methods of the present invention is the excitation and emission wavelengths for detection. FRET pairs with a long wavelength for excitation and emission are less prone to interference from cellular components and from compounds used in drug discovery and are thus preferred for the methods of the present invention. Such called NIR dyes useful for FRET based protease assays are well known in the state of the art (see for example, Pham W et al. Bioconj. Chem. (2004); 15 1403-1407) and the present invention benefits from new technologies developed for sensitive and specific detection of protease activities including new NIR dyes (see for example Peng X et al. A nonfluorescent, broad-range quencher dye for Forster resonance energy transfer assays. Analytical Biochemistry Epub Feb. 25, 2009)) with a better signal to background fluorescence ratio upon cleavage by the specific protease. For example a suitable substrate for granzyme B detection using FRET is 5'-FAM-Ser-Ile-Glu-Pro-Asp-Ser-Gly-Ser-TAMRA.

Time resolved FRET or TR-FRET is a variant of FRET in which lanthanide chelates such as those of terbium, are used as the donor species. Because terbium chelates have fluorescent lifetimes that are many orders of magnitude longer than standard organic fluorophores, TR-FRET can be measured after such interference has completely decayed. This, coupled with the ratiometric readout of acceptor intensity to donor intensity provides for a useful readout for HTS assays.

In one embodiment of the present invention peptide cleavage by granule secreted protease is detected with time resolved fluorometry. For example a peptide could be coupled with a fluorescent lanthanide chelate at one end and with a quencher of the lanthanide chelate at the other end. Upon cleavage by the protease the lanthanide chelate and the quencher will be separated as the substrate is cleaved. One relevant property of time resolved FRET technology for the methods of the present invention is that fluorescence emission could be delayed from excitation and thus autofluorescence of compounds used in the drug discovery process is avoided. For example, a useful substrate for detection of secreted granzyme B is Lanthan-IEPDSG-Quench wherein Lanthan is a chelate of a lanthanide, for example, an europium chelate and Quench is a suitable quencher of the lanthanide fluorescence, for example QSYsup® 7.

In one preferred embodiment the method used for sensitive detection of secreted protease is selected from highly efficient FRET pairs with minimal interference from both cellular and compound used in drug discovery such as for example, 5'FAM and TAMRA FRET pair, near infrared FRET pairs and lanthanide chelates based time-resolved FRET methods.

In still another embodiment of the present invention granule secreted proteases are measured with peptide-modified luciferin substrates (see for example, Geiger R and Miska W, U.S. Pat. No. 5,035,999) in a suitable buffer containing both ATP and luciferase. For example, a suitable peptide for determination of secreted granzyme B is Ile-Glu-Pro-Asp-amidoluciferin (IEPD-aminoluciferin), wherein the carboxylic acid of aspartic acid is conjugated to the 6-aminoluciferin to produce an amide luciferin that is not cleaved by luciferase unless IEPD-amidoluciferin is first cleaved by secreted human granzyme B. Using this granzyme B substrate, granule stored exocytosis is coupled to luminescence and thus autofluorescence of both cells and compounds used for drug discovery does not produce interference with assay readout.

Rhodamine 110 based protease substrates are bisamide derivatives of the fluorophore were peptides are covalently linked to each of the amino groups of rhodamine 110 (R110) (see for example, Mangel W et al U.S. Pat. No. 4,557,862), thereby suppressing both the visible absorption and fluorescence of the dye. Upon enzymatic cleavage, the nonfluorescent bisamide substrate is converted in a two-step process, first to the fluorescent monoamide and then to the even more fluorescent R110. The R110 cleavage product has spectral properties similar to those of fluorescein and a large extinction coefficient, thus providing ease of use under standard fluorescein filter set-ups and excellent signal to background ratios. In one embodiment of the present invention protease substrates for proteolytic detection are rhodamine 110 modified peptides.

In another embodiment useful preferred substrates for reporter detection are cell impermeable substrates suitable for reporter detection in a mix that contain cells.

In another embodiment of the present invention preferred detection of secreted proteases comprises an enzymatic cascade for signal amplification. Protease cascades that enable signal amplification are well known in the state of the art (see for example, Harris, C. U.S. Pat. No. 4,463,090). The best example of a protease amplification cascade is the blood coagulation cascade where the first protease activates a zymogen to produce an activate protease and this second protease also activates a zymogen to produce a second active protease, thus creating a cascade where the initial signal is amplified up to 1000 fold. Zymogens with very low basal activity are needed for signal amplification with a high signal to background ratio. For example, native caspase 8 zymogen possesses 1% of the activity of the fully processed enzyme, a very substantial activity compared with most protease zymogens (see Muzio M. et al J. Biol. Chem. (1998) 273: 2926-2930) and thus native caspase-8 has a high background for sensitive detection of secreted reporters like granzyme B. Instead, human procaspase-3 can be efficiently cleaved and activated by either human, rat, horse or chimpanzee granzyme B to produce a mature caspase-3 about 10.000 times more active than uncleaved zymogen and thus highly useful for detection of granule secreted proteases. A high zymogenicity index is a property particularly preferred for proteases useful for detection of secreted reporters in the methods of the present invention. In addition to a high zymogenicity index, preferred zymogens for the methods of the present invention are selected from enzymes with a high catalytic efficiency after activation and a low basal activity of enzyme. Zymogens with those properties need to be selected for a sensitive detection of granule exocytosis in the present invention.

The basal activity of a zymogen is related with zymogenicity index, but here are some differences relevant to the methods of the present invention. First, two enzymes with the same zymogenicity index could have a different basal activity but the enzyme with a higher basal activity is also the enzyme with higher catalytic efficiency. Preferred for the methods of the present invention are enzymes with the highest possible zymogenicity index and with the lowest possible basal enzymatic activity. Second, basal activity is not only related to zymogenicity, because certain enzymes like procaspase-3 could be readily autoactivated when present at high concentration. For example, the zymogenicity index of procaspase-3 is about 10.000 and thus very high but if the enzyme is stored at a high concentration, the enzymes autoactivates and the basal activity could be very high. Third, the basal activity relevant to the methods of the present invention is that present in cell culture supernatant of cells in the absence of a modulator of regulated exocytosis and not only that produced by the transfected granule stored reporter. For example, granzyme A is a serine protease that belongs to tryptase-family of proteases. Such tryptase family is characterized by a cleavage sequence after arginine or lysine amino acids. Although human granzyme A has an optimal cleavage sequence that comprises IGDR or VANR at P4-P3-P2-P1 (see for example, Mahrus S and Craik C S. Chemistry & Biology (2005), 12, 567-577) and thus potentially useful for the methods of the present invention, the activity of tryptases already present in an unstimulated cell culture supernatant of non-transfected RBL-2H3 cells is so high that there is no difference between RBL-2H3 cells stably transfected with human granzyme A stimulated with a secretion modulator like ionomycin and untransfected cells either stimulated or not with ionomycin. But if cell culture supernatant is removed and cells are washed with a serum free buffer, for example a modified HBSS, then the basal tryptase activity is lowered to levels where human granzyme A becomes a useful reporter for the methods of the present invention.

Verheijen et al have developed an artificial amplification cascade useful for protease quantification (see Verheijen J H et al. Biochem. J. (1997) 323, 603-609 and Verheijen J H, U.S. Pat. No. 8,115,252) where pro-urokinase is modified to contain a recognition site which is cleavable by the protease to be quantified. Others have used different proteases modified at the cleavage site like procaspase-3 as a measure of protease activity. For example, Li Y et al (see Li Y. et al. Molecular Biotechnology, (2001) Vol. 18, No 1, 1-10) have developed a modified procaspase-3 containing beta-secretase cleavage site that induces apoptosis in 293T cells a well know effect of active caspase-3 and they have demonstrated that the modified caspase-3 induced apoptosis is correlated with the susceptibility of beta-secretase recognition sequence to beta-secretase and even that protease competitors prevent the modified caspase-3 induced cell death. In another example, Vocero-Akbani A M et al (see Vocero-Akbani A M et al Nat. Med. (1999), Vol 5, No. 1:29-33) have engineered a procaspase-3 that substitutes Human Immunodeficiency Virus (HIV) proteolytic cleavage sites for endogenous ones. Once inside the cells this engineered procaspase-3 remains inactive in uninfected cells but in HIV-infected cells, this procaspase-3 becomes processed into an active form by HIV protease, resulting in apoptosis of the infected cell. All the above examples of protease cascades are relevant for the methods of the present invention, although the preferred zymogen for the methods of the present invention is based on a natural amplification cascade based on native procaspase-3. Several caspases like caspase-3 and caspase-8 are the natural substrates of granzyme B and we have used this property of caspase-3 to develop a fast and sensitive method for quantification of secreted granzyme B.

In one specific embodiment of the present invention, the preferred zymogen used for human, rat, chimpanzee or horse granzyme B is unmodified human procaspase-3 comprising amino acids from serine at position 29 to histidine at position 277 according to Genbank NM_032991.

In another embodiment human procaspase-3 useful for detection of secreted human granzyme B, rat granzyme B, chimpanzee granzyme B or horse granzyme B is a mutated variant with the threonine at position 174 mutated to proline for a more efficient cleavage by human, rat, chimpanzee or horse granzyme B. In a still further embodiment human pro-caspase-3 is further modified to reduce autoactivation by changing at least serine at position 176 to valine or leucine. In one embodiment human procaspase-3 with improved cleavage by human granzyme B has proline at position 174 instead of threonine and the serine at 176 mutated to valine, glycine at 177 mutated to leucine, valine at 178 mutated to methionine and aspartic acid at 179 mutated to glutamic acid. Such procaspase-3 with sequence IEPDVLME comprising amino acids P4-P3-P2-P1-P1'-P2'-P3-P4' is optimal for human granzyme B cleavage and has very low autoactivation in absence of granzyme B but full activity when cleaved by human granzyme B. Such mutated human pro-caspase3 with highly reduced autoactivation is listed as SEQ ID NO:11

It is known that the tetrapeptide specificity of mouse granzyme B differs significantly from human granzyme B. Human and mouse granzyme B cleave the species-specific procaspase-3 more efficiently than the heterologous pro-caspase-3 for each granzyme B. Cleavage of human pro-caspase-3 by mouse granzyme B at P4-P3-P2-P1 sequence comprising IETD (Isoleucine-glutamic acid-threonine-aspartic acid at position 175) is about 6-fold less efficient than by the human protease eventhough both caspases have an identical IETD cleavage sequence, thus the use of a species-specific procaspase-3 is preferred for detection of secreted granzyme B in the methods of the present invention.

In one embodiment of the present invention the method used to measure the enzymatic activity of useful activated zymogens is selected from a colorimetric, a fluorescent, a FRET, a time resolved-FRET or a luminescent method.

Examples of substrates useful for detection of active caspase 3 are: 5'-FAM-Ser-Asp-Glu-Val-Asp-Ser-Gly-Ser- TAMRA, a FRET substrate; Lanthan-CDEVDK-Quench wherein Lanthan is a chelate of a lanthanide, for example, an europium chelate and Quench is a suitable quencher of the lanthanide fluorescence, for example QSYsup.® 7 for time-resolved fluorometry; DEVD-AMC and DEVD-AFC for fluorescence and DEVD-aminoluciferin for luminiscence detection.

In another preferred embodiment, the substrate of the activated zymogen like caspase-3 is a cell impermeable substrate, to reduce background due to intracellular substrate hydrolysis. In another embodiment the preferred cell impermeable substrate of active caspase-3 is a peptide of sequence DEVD coupled to either C-terminally coupled to 7-amido-4-methylcoumarin or to rhodamine-110 or to aminoluciferin or coupled at one end with a fluorophore for either FRET or time-resolved-FRET and at the other end with a suitable quencher of the fluorescence of specific fluorophore.

In another embodiment of the present invention the activity of secreted proteases could be detected by a zymogen activated by such secreted protease where the zymogen is a circularly permuted enzyme devoid of enzymatic activity unless it is activated by the specific protease. Circular permutation is a process where the amino and carboxy termini of an enzyme are joined and a new amino and carboxy termini are created anywhere in the molecule. Useful circularly permuted enzymes for the methods of the present invention are enzymes that are converted into zymogens with low basal activity by circular permutation and the activity is retored by protease cleavage. Circularly permuted zymogens are well known in the state of the art. Plainkum P et al (see Plainkum P et al Nat Struct Biol. 2003 February; 10(2): 115-9.) where the first to demonstrate that by linking the N and C termini of ribonuclease A, the active site is blocked with the amino acid sequence recognized by plasmepsin II, a highly specific protease from *Plasmodium falciparum*. They generated a new N and C termini by circular permutation and inn the presence of plasmepsin II, a ribonuclease zymogen gained approximately 1000-fold in catalytic activity and maintained high conformational stability. Other investigators have applied the circular permutation of N and C termini to create novel zymogens that could be activated by proteases (see for example, Johnson R J et al FEBS Journal Volume 273, Issue 23, pp. 5457-5465, 2006 and Jucovic M et al Protein Engineering Design and Selection 2008 21 (10):631-638)

In another embodiment of the present invention suitable zymogens useful for quantification of secreted proteases are selected from enzymes with low basal activity for a high signal to background ratio and thus a more robust assay and enzymes with a high catalytic efficiency after activation by the secreted protease. For example, a modified pro-enterokinase has a very high basal activity, that is a low zymogenicity index that precludes its use for sensitive detection of human granzyme B.

In another embodiment of the present invention preferred zymogens for quantification of secreted proteases are selected from enzymes whose reaction buffer can be made compatible with media used for exocytosis.

For a sensitive reporter detection based on any of the detection technologies a specific protease substrate that is cleaved with very high efficiency is needed. Amino acids residues around the cleavage sequence are the main determinants of the catalytic efficiency of the protease reporter for any particular substrate.[1]

In one embodiment useful granule stored reporters with tryptase-like activity are selected from a group comprising granzyme A and granzyme K. In another embodiment useful granule stored reporter with Asp-ase like activity is a granzyme B. In another embodiment useful granule stored reporters with chymase-like activity are selected from a group comprising granzyme H, chymase and cathepsin G. In a still further embodiment useful granule stored reporters with elastase-like activity are selected from a group comprising granzyme M, neutrophil elastase and proteinase 3.

In one embodiment useful granule stored reporters are selected from a group of species comprising human, mouse, rat, horse, cow, monodelphis, sheep and goat serine endopeptidases.

In one specific embodiment of the present invention, the heterologous reporter is selected from a group of serine proteases that comprises granzyme B from human, rat, chimpanzee and horse species because granzyme B protease is the only known serine protease with an absolute requirement for cleavage after aspartic acid.

In one embodiment of the present invention the preferred substrate for granzyme B human, rat, chimpanzee and horse species used as a reporter of the sensor comprises at P4 an amino acid selected from isoleucine or valine; at P3 an amino acid selected from glutamic acid, methionine, alanine, glycine, hystidine, serine, glutamine, aspartic acid, threonine, tryptophan, tyrosine or valine; at P2 an amino acid selected from proline, threonine, glutamine, aspartic acid, alanine, phenylalanine, serine, tryptophan, tyrosine, valine, glutamic acid, glycine or histidine; and at P1 aspartic acid.

In another embodiment of the present invention further preferred extended substrates for those granzymes B from human, rat, chimpanzee or horse species comprise at P1' a non charged amino acid selected from valine, serine, tyrosine and phenylalanine and at P2' an amino acid selected from serine, alanine, glycine, tyrosine, leucine or glutamic acid.

In another preferred embodiment of the methods of the present invention further preferred substrate of granzyme B of human, rat, chimpanzee or horse species comprises the sequence isoleucine at P4, glutamic acid at P3, proline or threonine at P2 and aspartic acid at P1. Further preferred substrate comprises also serine at P1' and glycine or leucine at P2'.

In one embodiment of the present invention the substrate for granzyme A of human, rat and mouse species used as a reporter of the sensor comprises at P4 an amino acid selected from isoleucine, valine, or glycine; at P3 an amino acid selected from alanine, glycine, serine, phenylalanine or tyrosine; at P2 an amino acid selected from asparagine or phenylalanine and at P1 arginine or lysine.

In another embodiment of the present invention further preferred extended substrates for the human, rat or mouse granzyme A comprise at P1' long linear hydrophobic amino acids such as the aliphatic side chain of lysine and methionine, or unbranched hydrophobic aminoacids like alanine or polar residues like serine; and at P2'' an amino acid selected from valine, leucine, isoleucine, phenylalanine and tyrosine.

In another preferred embodiment of the methods of the present invention further preferred substrate of human granzyme A comprises valine or isoleucine at P4, alanine, glycine or serine at P3, asparagine or aspartic acid at P2 and arginine at P1. Further preferred substrate comprises also serine or methionine at P1' and valine, leucine or phenylalanine at P2''. In another preferred embodiment of the methods of the present invention further preferred substrate of mouse granzyme A comprises glycine or valine at P4, tyrosine or phenylalanine at P3, phenylalanine or asparagine at P2 and arginine at P1. Further preferred substrate for mouse granzyme A comprises also serine or methionine at P1' and valine, leucine or phenylalanine at P2'.

In one embodiment of the present invention the substrate for human chymase used as a reporter of the sensor comprises at P4 an amino acid selected from glycine, isoleucine, valine, arginine, proline, glutamine or leucine; at P3 an amino acid selected from alanine, valine, leucine, histidine, serine, threonine or glutamic acid; at P2 an amino acid selected from asparagine, serine, aspartic acid, threonine, proline, leucine, alanine or valine and at P1 tyrosine or phenylalanine.

In another embodiment of the present invention further preferred extended substrates for human chymase comprises at P1' serine or glycine; at P2' an amino acid selected from aspartic acid, alanine, glutamic acid or glycine and at P3' an amino acid selected from valine, leucine, alanine or glycine.

In another preferred embodiment of the methods of the present invention further preferred substrate of human chymase comprises histidine, glutamic acid or threonine at P3; proline or threonine at P2; and phenylalanine or tyrosine at P1. Further preferred substrate comprises also serine at P1' and aspartic acid, glutamic acid or alanine at P2'.

In one embodiment of the present invention the substrate for proteinase 3 of human, rat and mouse species used as a reporter of the sensor comprises at P4 an amino acid with a small aliphatic residue like valine and alanine; at P3 an amino acid with a small aliphatic residue like alanine and valine; at P2 a charged amino acid selected from aspartic acid, glutamic acid, arginine and lysine and at P1 an amino acid selected from cysteine, norvaline, valine, alanine and methionine.

In another embodiment of the present invention further preferred extended substrates for the human, rat or mouse proteinase 3 comprise at P1' a positively charged amino acid selected from arginine and lysine or an amino acid with a small aliphatic residue like alanine or valine; and at P2" an amino acid selected from aspartic acid, glutamic acid or glutamine.

In another preferred embodiment of the methods of the present invention further preferred substrate of human proteinase 3 comprises valine or alanine at P4; valine or alanine at P3; aspartic acid at P2 and cysteine, valine or norvaline at P1. Further preferred substrate comprises also alanine or lysine at P1', aspartic acid at P2' and arginine at P3".

In one embodiment of the present invention the substrate for neutrophil elastase of human, rat and mouse species used as a reporter of the sensor comprises at P4 proline or an amino acid with a small aliphatic residue like valine and alanine; at P3 an amino acid with a small aliphatic residue like alanine and valine or a negatively charged amino acid selected from aspartic acid and glutamic acid; at P2 an amino acid with a small aliphatic residue like alanine and valine or a negatively charged amino acid selected from aspartic acid and glutamic acid and at P1 a hydrophobic or a polar amino acid selected from isoleucine, norvaline, valine, alanine and methionine.

In another embodiment of the present invention further preferred extended substrates for the human, rat or mouse neutrophil elastase comprise at P1' a hydrophobic or a polar or a negatively charged amino acid and at P2' a hydrophobic or a negatively charged amino acid.

In another preferred embodiment of the methods of the present invention further preferred substrate of human neutrophil elastase comprises proline or valine or alanine at P4; glutamic acid or valine or alanine at P3; glutamic acid at P2 and isoleucine, valine or norvaline at P1. Further preferred substrate comprises also methionine at P1', arginine or aspartic acid at P2' and arginine at P3'.

One relevant feature of the sensors of the present invention is that different cell based sensors may be combined in the same reaction vessel to produce a multiplex assay in each reaction vessel. To be combined in the same reaction vessel each cell based sensor must produce a unique combination of a specific exocytosis modulator and a specific granule stored reporter. In addition, when released such granule stored reporter must be detected with a specific substrate with minimal or preferably no interference with other substrates or other released reporters.

In one embodiment of the present invention at least two cell based sensors, each producing a unique specific combination of one exocytosis modulator with one granule stored reporter, may be mixed in the same reaction vessel to produce a multiplex reaction.

In a further embodiment two or three or four or five or six different cell based sensors are mixed in the same reaction in a media compatible with cell viability, granule exocytosis and enzymatic activity of all granule stored reporters. In one specific embodiment one media compatible with cell viability, granule exocytosis and enzymatic activity is 25 mM Hepes pH=7.4; 130 mM NaCl 5.65 mM KCl; 1.2 mM of KH2P04; 0.6 mM MgCl2; 1.8 mM CaCl2; 0.1 percent of glucose and 0.1 percent of bovine serum albumin.

In one preferred embodiment the method used for detection of enzymatic activity of mixed reporters is selected from FRET or from time-resolved FRET.

For example, Biosearch Technologies has developed highly efficient quenchers marketed under the trademark BHQsup™ or Blackhole quenchers, while Anaspec has developed QXLsup™ quenchers and Perkin Elmer QSYsup.® quenchers. For a quencher-fluorophore pair to be efficient the emission fluorescence spectra of the fluorophore must overlap with the absorbance spectra of the quencher. Several pairs of fluorophore-quencher may be mixed to develop a multiplex reaction by combining fluorophores whose fluorescence emission spectra is no overlapped or is minimally overlapped.

In another embodiment activity of different reporter enzymes is detected by a combination of fluorescent and luminescent methods.

C. Applications of the Cell Based Sensor of the Present Invention

Cell based sensors of the present invention are in general useful for testing interactions between at least two molecules, one acting as the exocytosis modulator and the other as the specific ligand of the exocytosis modulator. For example, in drug discovery thousands or even millions of small molecules are tested against a target to find small molecules that modify the activity of such target. In a particular example, compounds are screened for agonists or antagonist of G-protein coupled receptors, a highly druggable class of receptors. But the same sensor has applications in detection and quantitation of compounds that modulate granule exocytosis, for example, drugs of abuse in several samples for example in the food industry, environmental samples and for diagnosis. Uses of the sensor are not limited to either cell surface receptors or to small modulators of surface receptors. For example, with a pair of two molecules that bind to a protein to be determined, fast, specific and sensitive detection could be carried out by using the sensor of the present invention provided one of the molecules that bind to the protein to be determined is a specific immunoglobulin E and the other molecule that bind to the protein to be determined induces oligomerization of the protein to be determined. Other uses of the above sensor are for testing anti-allergic compounds and for detection of allergens.

D. Kits for Testing if a Compound Modulates Exocytosis

The present invention also comprises kits for testing if a compound modulates exocytosis.

Such kit comprises at least: a hemopoyetic cell line with professional regulated exocytosis transfected with at least a heterologous protease reporter under the control of a suitable promoter and a specific substrate for detection of secreted heterologous protease reporter. In addition, the hemopoyetic cell line with professional regulated exocytosis may be either transfected with a heterologous exocytosis modulator under the control of a suitable promoter, like a GPCR, a heterologous Fc gamma I receptor or a heterologous Fc epsilon I receptor, or an endogenous exocytosis modulator like the endogenous Fc epsilon receptor I (the IgE receptor) could be used. Kits using the IgE receptor as the exocytosis modulator may contain an IgE specific for the analyte to be determined and a second molecule to induce oligomerization of the analyte bound to IgE.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein. Whereas, particular embodiments of the invention have been described herein for purposes of description, it will be appreciated by those skilled in the art that numerous variations of the details may be made without departing from the invention as described in the appended claims.

The following table describes a summary of granule stored protease reporters used in examples.

TABLE 1

Examples of granule stored reporters used in the methods of the present

| Gene | Genebank Accession Number | Official symbol | Primers used for amplification |
|---|---|---|---|
| Asp-like serine proteases | | | |
| Human granzyme B | NM_004131 | GZMB | 17, 18 |
| Horse granzyme B | NM_001081881 | GZMB | 21, 22 |
| Rat granzyme B | NM_138517 | GZMB | 19, 20 |
| Bovine granzyme B | XM_585453 | GZMB | 25, 26 |
| Chimpanzee granzyme B | XM_509879 | GZMB | 23, 24 |
| Monodelphis granzyme B | XM_001369720 | GZMB | 33, 34 |
| Tryptase-like serine proteases | | | |
| Human granzyme A | NM_006144 | GZMA | 15, 16 |
| Human granzyme K | NM_002104 | GZMK | 29, 30 |

TABLE 1-continued

Examples of granule stored reporters used in the methods of the present

| Gene | Genebank Accession Number | Official symbol | Primers used for amplification |
|---|---|---|---|
| Chymase-like serine proteases | | | |
| Human granzyme H | NM_033423 | GZMH | 27, 28 |
| Human chymase | NM_001836 | CMA1 | 85, 86 |
| Human cathepsin G | NM_001911 | CTSG | 87, 88 |
| Elastase-like serine proteases | | | |
| Human granzyme M | NM_005317 | GZMM | 31, 32 |
| Human neutrophil elastase | NM_001972 | ELA2 | 89, 90 |
| Human proteinase | NM_002777 | PRTN3 | 81, 82 |

The following table describes a summary of cell lines used in examples.

TABLE 2

Cell lines used in examples in the methods of present invention

| Cell Line | Accession Number | Source | Hemopoyetic Origin | Professional Regulated Exocytosis |
|---|---|---|---|---|
| HEK293 | CRL-1573 ™ (ATCC) | Fetal human kidney | No | No |
| CHO-K1 | CCL-61 ™ (ATCC) | Chinese hamster ovary | No | No |
| NK-92 | CRL-2407 ™ (ATCC) | Human malignant non-Hodgkin's lymphoma | Yes | Yes |
| RBL-2H3 | CRL-2256 ™ (ATCC) | Rat (Strain Wistar) basophilic leukemia | Yes | Yes |
| 32D | CRL-11346 ™ (ATCC) | Mouse bone marrow | Yes | Yes |
| A-431 | CRL-1555 ™ (ATCC) | Human epidermoid carcinoma | No | No |
| PC-12 | CRL-1721 ™ (ATCC) | Rat adrenal gland pheochromocytoma | Yes | Yes |
| YT | ACC 434 (DSMZ) | Human T/NK cell leukemia | Yes | Yes |
| Jurkat | ACC 282 (DSMZ) | Human T cell leukemia | Yes | No |

The following table describes a summary of exocytosis modulators used in examples.

TABLE 3

Examples of surface receptors used as exocytosis modulators in the methods of the present invention.

| Gene | Genbank Accession Number | Official symbol | Primers used for amplification |
|---|---|---|---|
| GPCR (G-protein coupled receptors) | | | |
| Human Bradykinin Receptor 81 | NM_000710 | BDKRB1 | 35, 36 |
| Human Adenosine 3 Receptor | NM_001081976 | ADORA3 | 37, 38 |
| Human Adrenergic Alpha 2A Receptor | NM_000681 | ADRA2A | 39, 40 |
| Human Adrenergic Beta 2 Receptor | NM_000024 | ADRB2 | 41, 42 |
| Human Angiotensin II Receptor. type 1 | NM_031850 | AGTR1 | 43, 44 |

TABLE 3-continued

Examples of surface receptors used as exocytosis modulators in the methods of the present invention.

| Gene | Genbank Accession Number | Official symbol | Primers used for amplification |
|---|---|---|---|
| Human Arginine Vasopressin Receptor 2 | NM_000054 | AVPR2 | 45, 46 |
| Human Chamokine (C-X3-C motif) Receptor 1 | NM_001337 | CX3CR1 | 47, 48 |
| Human Cholecystokinin B Receptor | NM_176875 | CCKBR | 49, 50 |
| Human Cholinergic Muscarnic 2 Receptor | NM_001006630 | CHRM2 | 53, 54 |
| Human Corticotropin Releasing Hormone Receptor 1 | NM_004382 | CRHR1 | 55, 56 |
| Human Dopamine Receptor D1 | NM_000794 | DRD1 | 57, 58 |
| Human Dopamine Receptor D2 | NM_016574 | DRD2 | 59, 60 |
| Human Endothelin Receptor type B | NM_000115 | EDNRB | 61, 62 |
| Human Glutamate Receptor, Metabotropic 4 | NM_000841 | GRM4 | 67, 68 |
| Human 5-Hydroxytryptamine/Serotonin Receptor 1B | NM_000863 | HTR1B | 69, 70 |
| Human Interleukin 8 Receptor | NM_000634 | IL8RA | 71, 72 |
| Human Melanocortin 1 Receptor | NM_002386 | MC1R | 73, 74 |
| Human Neuropeptide Y Receptor Y1 | NM_000909 | NPY1R | 75, 76 |
| Human Tachykinin Receptor 3 | NM_001059 | TACR3 | 77, 78 |
| Human Somatostain Receptor 2 | NM_001050 | SSTR2 | 79, 80 |
| Tyrosine kinase receptors | | | |
| Human Epidermal Growth Factor Receptor | NM_201284 | EGFR | 83, 84 |

The following table list all primers used in the examples.

TABLE 4

Sequences of primers used for amplification of genes in examples of the

| SEQUENCE NUMBER | ORIENTATION | SEQUENCE (5'-3') |
|---|---|---|
| SEQ ID NO: 13 | Sense | GTTACATATGTCTGGAATATCCCTGGACAACAG |
| SEQ ID NO: 14 | Antisense | GTTCTGCTCGAGGTGATAGAAATAGAGTTCTTTTGTGA |
| SEQ ID NO: 15 | Sense | TTTTCTCGAGAGCAGCCACAATGAGGAACT |
| SEQ ID NO: 16 | Antisense | GTGCGGCCGCTTAACTGCTCCCTTGATAGTCATAATT |
| SEQ ID NO: 17 | Sense | GATACTCGAGGGCAGCCTTCCTGAGAAGATG |
| SEQ ID NO: 18 | Antisense | GTTGTTGCGGCCGCTTAGTAGCGTTTCATGGTTTTCTT |
| SEQ ID NO: 19 | Sense | TTTTCTCGAGCCTTCCAGGGAAGATGAAGCT |
| SEQ ID NO: 20 | Antisense | TTTTGCGGCCGCTAGTTAGCTCTTTTTCATAGTTTTC |
| SEQ ID NO: 21 | Sense | GTTGTTCTCGAGATGCAACCGATACTCCTGCTG |
| SEQ ID NO: 22 | Antisense | TTTTGCGGCCGCTCAGAGAGATTTCATGGTCTTTTTGAT |
| SEQ ID NO: 23 | Sense | GTTACTCGAGATGAAGTCACTGAGCCTGCTC |
| SEQ ID NO: 24 | Antisense | GTTGTTGCGGCCGCTTAGTGGCGTTTCATGGTTTTCTT |
| SEQ ID NO: 25 | Sense | GTTGTTCTCGAGATGCAGCCGATCCTCCTGCTGCTC |
| SEQ ID NO: 26 | Antisense | TTTTGCGGCCGCTCACACACTACCTTGACGTTTATA |
| SEQ ID NO: 27 | Sense | TTATCTCGAGGAGAAAATGCAGCCATTCCTC |
| SEQ ID NO: 28 | Antisense | TTTTGCGGCCGCTTAGAGGCGCTTCATTGTTCT |
| SEQ ID NO: 29 | Sense | TTATCTCGAGAATATGACTAAGTTTTCTTCCTTTT |
| SEQ ID NO: 30 | Antisense | TTTTGCGGCCGCTTAATTTGTATGAGGCGGGAC |
| SEQ ID NO: 31 | Sense | TTTTCTCGAGAGCGCCATGGAGGCCTGCGT |

TABLE 4-continued

Sequences of primers used for amplification of genes in examples of the

| SEQUENCE NUMBER | ORIENTATION | SEQUENCE (5'-3') |
|---|---|---|
| SEQ ID NO: 32 | Antisense | TTTTGCGGCCGCCATCACCCCAGGGCATCAGGC |
| SEQ ID NO: 33 | Sense | TTTTCTCGAGATGCAACCGATACTCCTGCTC |
| SEQ ID NO: 34 | Antisense | TTTTGCGGCCGCTTAGCGTTTATCTTCCAGAGTTTT |
| SEQ ID NO: 35 | Sense | TTTTCTCGAGTGGCCCCCTCTAGAGCTTCAAT |
| SEQ ID NO: 36 | Antisense | TTTTGCGGCCGCTTGGTTCAATGCTGTTTTAATT |
| SEQ ID NO: 37 | Sense | GAAGCTCGAGCCCAACAACAGCACTGCTCT |
| SEQ ID NO: 38 | Antisense | GATGGCGGCCGCTAACTACTCAGAATTTTTCTCAATG |
| SEQ ID NO: 39 | Sense | ACGCCTCGAGGGATCCCTGCAGCCGGACG |
| SEQ ID NO: 40 | Antisense | TTCTGCGGCCGCTCACACGATCCGCTTCCTGTCCCC |
| SEQ ID NO: 41 | Sense | AACTCTCGAGGGGCAACCAGGGAACGGCA |
| SEQ ID NO: 42 | Antisense | CTTTGCGGCCGCTTACAGCAGTGAGTCATTTGTA |
| SEQ ID NO: 43 | Sense | AATAGCCTCGAGATTCTCAACTCTTCTACTGAAG |
| SEQ ID NO: 44 | Antisense | GATGATGCGGCCGCTCACTCAACCTCAAAACATGG |
| SEQ ID NO: 45 | Sense | TTATCTCGAGCTCATGGCGTCCACCACTT |
| SEQ ID NO: 46 | Antisense | TTTAGCGGCCGCTCACGATGAAGTGTCCTTGG |
| SEQ ID NO: 47 | Sense | GTATCTCGAGGACCAGTTCCCTGAATCAGTG |
| SEQ ID NO: 48 | Antisense | ATCAGCGGCCGCTTCAGAGAAGGAGCAATGCAT |
| SEQ ID NO: 49 | Sense | GTACCTCGAGGATGTGGTTGACAGCCTTCTT |
| SEQ ID NO: 50 | Antisense | GTTGTTGCGGCCGCTCACTGGGGTGGGACCGAGGC |
| SEQ ID NO: 51 | Sense | TTTTCTCGAGAACACTTCAGCCCCACCTGCT |
| SEQ ID NO: 52 | Antisense | TTTTGAATTCGCGGCCGCTCAGCATTGACGAGAGGGAGTG |
| SEQ ID NO: 53 | Sense | CTCACTCGAGAATAACTCAACAAACTCCTCTAAC |
| SEQ ID NO: 54 | Antisense | TTATGCGGCCGCTTACCTTGTTGCTCCTATGTTCTT |
| SEQ ID NO: 55 | Sense | AGGTCTCGAGTCCCTCCAGGACCAGCAC |
| SEQ ID NO: 56 | Antisense | TTAAGCGGCCGCTCAGACTGCTGTGGACTGCTT |
| SEQ ID NO: 57 | Sense | CCTTCTCGAGAGGACTCTGAACACCTCTGC |
| SEQ ID NO: 58 | Antisense | AATAGCGGCCGCTTAGGTTGGGTGCTGACCGTTT |
| SEQ ID NO: 59 | Sense | GTTTTCTCGAGGATCCACTGAATCTGTCCTGG |
| SEQ ID NO: 60 | Antisense | GTAAGCGGCCGCTCAGCAGTGGAGGATCTTCAG |
| SEQ ID NO: 61 | Sense | GATGCTCGAGGAGAGAGGATTCCCGCCT |
| SEQ ID NO: 62 | Antisense | TTTTGCGGCCGCTCAAGATGAACTGTATTTATTACTG |
| SEQ ID NO: 63 | Sense | ACACCTCGAGCTGGCGGTCGGGAACCTCA |
| SEQ ID NO: 64 | Antisense | CGTAGCGGCCGCTCACACATGATGACAATTGGTTG |
| SEQ ID NO: 65 | Sense | TTTTCTCGAGGCTCTAAATGACTGTTTCCTTCT |
| SEQ ID NO: 66 | Antisense | TTTTGCGGCCGCCTAGACATACCGTTCGTGACAGA |
| SEQ ID NO: 67 | Sense | GTCAGTCGACAAACCCAAAGGCCACCCTCAC |
| SEQ ID NO: 68 | Antisense | TTTTGCGGCCGCCTAGATTGCATGGTTGGTGTAA |

TABLE 4-continued

Sequences of primers used for amplification of genes in examples of the

| SEQUENCE NUMBER | ORIENTATION | SEQUENCE (5'-3') |
|---|---|---|
| SEQ ID NO: 69 | Sense | CTGGCTCGAGGAACCGGGTGCTCAGTGC |
| SEQ ID NO: 70 | Antisense | TTAGGCGGCCGCTCAACTTGTGCACTTAAAACGT |
| SEQ ID NO: 71 | Sense | CAGCCTCGAGAATATTACAGATCCACAGATGT |
| SEQ ID NO: 72 | Antisense | TACAGCGGCCGCTCAGAGGTTGGAAGAGACATT |
| SEQ ID NO: 73 | Sense | AGACCTCGAGGCTGTGCAGGGATCCCAGAGA |
| SEQ ID NO: 74 | Antisense | CACTGCGGCCGCTTCACCAGGAGCACGTCAGCAC |
| SEQ ID NO: 75 | Sense | GACGGTCGACAATTCAACATTATTTTCCCAGGTT |
| SEQ ID NO: 76 | Antisense | TATCGCGGCCGCTCAGATTTTTTCATTATCATCATTG |
| SEQ ID NO: 77 | Sense | AATACTCGAGCCTGCAGCAGAAACCTGGATA |
| SEQ ID NO: 78 | Antisense | ATTTGCGGCCGCGGAAATGGAATTAAGAATATTCAT |
| SEQ ID NO: 79 | Sense | GTCACTCGAGGACATGGCGGATGAACCACTC |
| SEQ ID NO: 80 | Antisense | TGGTGCGGCCGCTCAGATACTGGTTTGGAGGTC |
| SEQ ID NO: 81 | Sense | GTTATCTCGAGATGGCTCACCGTCCCCCCAG |
| SEQ ID NO: 82 | Antisense | GTTGTTGCGGCCGCTGTGGGAGGGGCAGTTCAGG |
| SEQ ID NO: 83 | Sense | TTTTCTCGAGCGACCCTCAGGGACGGCC |
| SEQ ID NO: 84 | Antisense | TTTTGCGGCCGCGGTCATGCTCCAATAAATTCACT |
| SEQ ID NO: 85 | Sense | GTTACTCGAGATGCTGCTTCTTCCTCTCCCC |
| SEQ ID NO: 86 | Antisense | GTTGTTGCGGCCGCTTAATTTGCCTGCAGGATCTG |
| SEQ ID NO: 87 | Sense | AAAACTCGAGGGAAAGATGCAGCCACTCCTG |
| SEQ ID NO: 88 | Antisense | AAAAGCGGCCGCCAGTCACAGGGGGGTCTCCA |
| SEQ ID NO: 89 | Sense | GATGACTCGAGATGACCCTGGGCCGCCGACTC |
| SEQ ID NO: 90 | Antisense | GTTGTGCGGCCGCTCAGTGGGTCCTGCTGGCCG |

Example 1

Selection of Useful Cell Lines for the Methods of the Present Invention

Several cell lines were transiently transfected with Lipofectamine 2000 (Invitrogen, USA), Superfect (Qiagen, Germany) or transiently electroporated with a microporator (Digital Bio Technology, South Korea) with pCMVSport-hGranzyme B vector, a vector in which human granzyme B is under the control of human CMV promoter (SEQ ID NO:8). This vector was used for selection of cells with professional granule exocytosis of granule reporters like granzymes. After 48 hours the cell culture media was changed and the basal level after 1 hour of culture without stimulus was evaluated by comparison with cells treated for 1 hour with ionomycin at 10 uM as inductor of granule exocytosis. The amount of granzyme B secreted into the culture media was evaluated by both a sandwich ELISA specific for human granzyme B (Ucytech, Netherlands) to quantify the total amount of protein using supernatant equivalent from 100.000, 50.000, 25.000 and 12.500 cells. Granzyme B activity was determined by hydrolysis of the granzyme B fluorescent substrate IEPD-AMC (Sigma, USA) using excitation at 360 nm and emission at 460 nm to measure activity of secreted enzyme in a BMG Labtech microplate fluorimeter in 96 well microplates using 125 microliters of supernatant from 500.000 cells and 125 microliters of specific substrate at 400 micromol per liter in HBSS buffer (Hanks Balanced Saline Salt buffer containing 25 mM Hepes pH=7.4; 130 mM NaCl 5.65 mM KCl; 1.2 mM of KH2P04; 0.6 mM MgCl2; 1.8 mM CaCl2; 0.1 percent of glucose). Microplates were incubated at 37 Celsius degrees on the reader and were kinetically read at 0, 15, 30, 45 and 60 minutes. Transfected granzyme B into non-hemopoyetic cells like A431, PC12, HEK293 and CHO-1 is not granule stored nor secreted when cells are treated with ionomycin; Jurkat and P815 are hemopoyetic cells without professional regulated exocytosis and constitutively secrete granzyme B without enzymatic activity; and hemopoyetic cells with professional regulated exocytosis like RBL-2H3 and 32D produce granzyme B, the vast majority of enzyme is stored into granules, is secreted by ionomycin treatment and the secreted enzyme is active. Thus hemopoyetic cells with professional granule exocytosis of granule stored protease reporters are suitable for the development of biosensors of the present invention.

Example 2

Selection of Useful Promoters for Reporter Expression in the Methods Of the Present Invention Using Transient Transfection Vectors were developed for expression of human granzyme B under the control of the following promoters: Moloney Leukaemia virus 5'-LTR (MoLV5'LTR, SEQ ID NO:3), human cytomegalovirus promoter, human phosphoglycerate kinase promoter and a chimeric promoter of human cytomegalovirus promoter and Moloney Leukaemia virus 5'-LTR (hCMV-MoLV5'LTR, SEQ ID NO:10). Each vector was individually transiently transfected by electroporation using a microporator (Digital Bio Technology, South Korea) into RBL-2H3 under standard conditions and 48 hour later cell were counted and seeded the night before experiment at a density of 100.000 cells per well in a 96 well microplate. Next day cells were washed with BSS buffer and treated for 1 hour treatment with ionomycin at 10 uM in a total volume of 30 microliters. Supernatants were assayed for granzyme B by a sandwich ELISA (Ucytech, Netherlands). Background of ELISA was 0.2 and the cut-off for a dilution to be considered positive was arbitrary chosen as 0.3. The minimal number of cells needed to produce a signal of 0.3 was determined for each tested promoter.

| Promoter | Minimal cell number for a positive signal by granzyme B ELISA |
| --- | --- |
| Moloney Leukaemia virus 5'-LTR (MoLV5'LTR, SEQ ID NO: 3) | 250 |
| human cytomegalovirus promoter (hCMV) | 2000 |
| human phosphoglycerate kinase promoter | 5000 |
| human cytomegalovirus promoter and Moloney Leukaemia virus 5'-LTR chimeric promoter (hCMV-MoLV5'LTR, SEQ ID NO: 10) | 150 |

Transient transfection by electroporation indicates that the order of potency of promoters for reporter expression is: hCMV-MoLV5'LTR>MoLV5'-LTR>hCMV>hPGK. Thus, transient transfection by electroporation suggests that all tested promoters are suitable for reporter expression. If a high level reporter expression is needed then promoters could be selected from hCMV-MoLV5'LTR chimeric promoter, MoLV-5'LTR promoter or hCMV promoter while if a lower reporter expression is needed then promoters could be selected from hPGK promoter or hCMV promoter.

Example 3

Development of Stable Cell Lines Expressing Human Granzyme B Under the Control of hCMV-MoLV5'LTR Chimeric Promoter, MoLV-5'LTR Promoter and hCMV Promoter Vectors were developed for stable expression of human granzyme B under the control of hCMV-MoLV5'LTR chimeric promoter, MoLV-5'LTR promoter or hCMV promoter. A hygromycin resistance cassette was included in the vector backbone for selection of stable populations of cells. The vector also included an IRES-NGFR (SEQ ID NO: 12) cassette cloned downstream of human granzyme B and thus, under the control of the same promoter for flow cytometry and/or selection of stable cells expressing granzyme B. Each vector was individually electroporated using a microporator (Digital Bio Technology, South Korea) into RBL-2H3 and after 48 hours hygromycin at 1500 ug/mL was added to culture for selection. After selection for about 2 weeks cells were analysed by flow cytometry (Guava Technologies, USA) with an antibody against NGFR coupled to FITC. Positive population where magnetically separated by MACS using anti-NGFR-MACS sup.R (Miltenyi Biotec, Germany). Sorted populations were again analysed by flow cytometry to check the sorting efficiency. Cells were subsequently seeded in 96 well microplates at 100.000 cells per well the night before the experiment for quantitative determination of secretion of human granzyme B by a sandwich ELISA (Ucytech, Netherlands). Next day cells were washed with HBSS buffer and incubated for 60 minutes at 37 Celsius degrees in 30 uL of HBSS containing 10 uM of ionomycin as inductor of granule exocytosis. Background of ELISA was 0.2 and the cut-off for a dilution to be considered positive was arbitrary chosen as 0.3. The minimal number of cells needed to produce a signal of 0.3 was determined for each tested promoter. The results were:

| Promoter | Minimal cell number for a positive signal by granzyme B ELISA |
| --- | --- |
| Moloney Leukaemia virus 5'-LTR (MoMLV5'LTR, SEQ ID NO: 3) | 75 |
| human cytomegalovirus promoter (hCMV) | 3300 |
| human cytomegalovirus promoter and Moloney Leukaemia virus 5'-LTR chimeric promoter (hCMV-MoLV5'LTR, SEQ ID NO: 10) | 40 |

The above results confirmed that all tested promoters were suitable for granule stored reporter expression although the expression from hCMV-MoMLV5'LTR chimeric promoter is higher than that of MoMLV-5'LTR promoter and hCMV promoter. Using cells with hCMV-MoMLV5'LTR chimeric promoter for expression of granzyme B and a sensitive ELISA, granzyme B secretion from less than 50 cells could be readily detected while about 75 cells could be detected when using MoMLV-5'LTR promoter for granzyme B expression.

Example 4

Selection of Useful Reporters for the Methods of the Present Invention

Vectors were developed to express human granzyme A, M, H and K and human neutrophil elastase, human chymase, human cathepsin G and human proteinase 3 under the control of hCMV-MoMLV5'LTR chimeric promoter and RBL-2H3 cells were individually transfected by electroporation using a microporator (Gentelbio, South Korea) with the above plasmids and also with human granzyme B plasmid as control and with cytosolically truncated hNGFR receptor as a surface tag for determination of the percentage of transfection by flow cytometry with a anti-hNGFR monoclonal antibody conjugated to FITC (Miltenyi Biotec, Germany). After 48 hours cells were harvested by pipetting, washed with HBSS buffer and counted. 650.000 cells in 200 microliters of HBSS buffer were treated in suspension with 10 uM ionomycin for 1 hour and after centrifugation at 400 g for 5 minutes the supernatants were analysed for activity with specific fluorescent substrates. Controls of cells incubated with HBSS buffer only were included. Fluorescent substrates were specific tetrapeptides conjugated to 7-Amido-4-Methylcoumarin (AMC) and were custom synthesized by a custom peptide supplier. Specific substrates were: VANR-AMC for granzyme A; KVPL-AMC for granzyme M; PTSY-AMC for granzyme H; YRFK-AMC for granzyme K; PEEI-AMC for human neutrophil elastase; PTSY-AMC for human chymase; PTSY-AMC for human cathepsin G; VADC-AMC for human proteinase 3 and IEPD-AMC for human granzyme B. Released AMC was measured by excitation at 360 nm and emission at 460 nm in a BMG Labtech microplate fluorimeter in 96 well microplates using 125 microliters of supernatant and 125 microliters of specific substrate at 400 micromol per liter in HBSS buffer. Microplates were incubated at 37 Celsius degrees on the reader and were kinetically read at 0, 15, 30, 45 and 60 minutes. Percentage of transient electroporation measured using truncated hNGFR tag and anti-hNGFR-FITC antibody was about 60 percent. All enzymes were active and thus suitable for the methods of the present invention but: among tryptase-like enzymes (granzymes A and K with cleavage after lysine of arginine) granzyme A had higher activity than granzyme K; among chymase-like enzymes (human granzyme H, human chymase and human cathepsin G with cleavage after tyrosine or phenylalanine) human chymase had the highest activity; among elastase-like enzymes (human granzyme M, human neutrophil elastase and human proteinase 3 with cleavage after bulk hydrophobic amino acids or cysteine) neutrophil elastase and proteinase 3 had equivalent activity that was higher than that of human granzyme M. Thus tryptase-like enzymes, chymase-like enzymes, elastase-like enzymes or asp-ase like enzymes may be used in the methods of the present invention.

Example 5

Development of Stable Cell Lines Expressing Granzyme A, Granzyme B, Human Chymase and Human Proteinase 3 Under the Control of hCV-MoLV5'LTR Chimeric Promoter As either tryptase-like enzymes, chymase-like enzymes, elastase-like enzymes or asp-ase like enzymes are useful for the methods of the present invention we selected human granzyme A (tryptase-like enzyme); human granzyme B (Asp-ase-like enzyme); human chymase (chymase-like enzyme) and human proteinase 3 (elastase-like enzyme) for further examples. Vectors were developed for stable expression of human granzyme A, human granzyme B, human chymase and human proteinase 3 under the control of hCMV-MoMLV5'LTR chimeric promoter. A hygromycin resistance cassette was included in the vector backbone for selection of stable populations of cells. The vector also included an IRES-NGFR cassette cloned downstream of granule stored protease reporter and thus, under the control of hCMV-MoMLV5'LTR promoter for flow cytometry and/or selection by MACS of stable cells expressing either human granzyme A or human granzyme B or human chymase or human proteinase 3. Each vector was individually electroporated using a microporator (Digital Bio Technology, South Korea) into RBL-2H3 and after 48 hours hygromycin at 1500 ug/mL was added to culture for selection. After selection for about 2 weeks cells were analysed by flow cytometry (Guava Technologies, USA) with an antibody against NGFR coupled to FITC. Positive population where magnetically separated by MACS using anti-NGFR-MACS sup.R (Miltenyi Biotec, Germany).

Sorted populations were again analysed again by flow cytometry to check the sorting efficiency. Percentage of NGFR positive cells was always higher than 65 percent. Cells were seeded the night before experiment in 24 well microplates at 650.000 cells per well in 800 microliters of complete cell culture medium. Next day cells were washed with HBSS buffer and were treated with 10 uM ionomycin for 1 hour at 37 Celsius degrees in 200 uL of HBSS buffer and after centrifugation at 400 g for 5 minutes supernatants were analysed for activity with specific fluorescent substrates. Controls of cells incubated with HBSS buffer only were included. Fluorescent substrates were: VANR-AMC for granzyme A; PEEI-AMC for human neutrophil elastase; PTSY-AMC for human chymase; VADC-AMC for human proteinase 3 and IEPD-AMC for human granzyme B. Released AMC was measured by excitation at 360 nm and emission at 460 nm in a BMG Labtech microplate fluorimeter in 96 well microplates using 125 microliters of supernatant and 125 microliters of specific substrate at 400 micromol per liter in HBSS buffer. Microplates were incubated at 37 Celsius degrees on the reader and were kinetically read at 0, 15, 30, 45 and 60 minutes. Control wells with substrate only in HBSS buffer were included to subtract autofluorescence of substrates to both cells treated with ionomycin and to cells treated with HBSS buffer only. Autofluorescence of peptide substrates in HBSS buffer was about 3000 while fluorescence of cells treated with HBSS buffer only for 60 minutes at 37 Celsius degrees was about 5000, that is basal release in the absence of exocytosis modulator was about 2000. In contrast, fluorescence of ionomycin-induced release of human granzymes A and B was about 20.000 for a signal to background of 10 when using the supernatant equivalent to 100.000 cells; fluorescence of ionomycin-induced release of human chymase was about 30.000 for a signal to background of 15 when using the supernatant equivalent to 100.000 cells and fluorescence of ionomycin-induced release of human proteinase 3 was about 12.000 for a signal to background of 6 when using the supernatant equivalent to 100.000 cells. Thus, tryptase-like enzymes, chymase-like enzymes, elastase-like enzymes or asp-ase like enzymes can be stably expressed into granules of hemopoyetic cells with professional regulated exocytosis and such granule stored proteases are released by exocytosis modulators to produce sensors with good signal to background ratios using specific AMC-coupled peptide substrates. All those enzymes types are thus useful for the methods of the present invention.

Example 6

Selection of Useful Granule Stored Protease Reporters from Different Species

This experiment was designed to test if granule stored protease reporters from other species different from human could be used for the methods of the present invention. As an example we selected granzyme B from different species. Vectors were developed for expression of human, rat, horse and chimpanzee granzyme B and RBL-2H3 cells were individually transfected with the plasmids comprising the chimeric promoter of hCMV-MoMLV5'LTR-GranzymeB-IRES-NGFR with hygromycin resistance for stable transfections. Each vector was individually electroporated using a microporator (Digital Bio Technology, South Korea) into RBL-2H3 and after 48 hours hygromycin at 1500 ug/ml was added to culture for selection. After selection for about 2 weeks cells were analysed by flow cytometry (Guava Technologies, USA) with an antibody against NGFR coupled to FITC. Positive population where magnetically separated by MACS using anti-NGFR-MACS sup.R (Miltenyi Biotec, Germany). Sorted populations were again analysed again by flow cytometry to check the sorting efficiency. Percentage of NGFR positive cells was always higher than 65 percent. Cells were seeded the night before experiment in 96 well microplates at 100.000 cells per well in 100 microliters of medium. Next day cells were washed with BSS buffer and were treated with 10 uM ionomycin for 1 hour at 37 Celsius degrees in 105 uL of HBSS buffer and after centrifugation at 400 g for 5 minutes supernatants were analysed for activity with specific fluorescent substrates. Controls of cells incubated with HBSS buffer only were included. Fluorescent substrate was IEPD-AMC for all granzymes B tested. Released AMC was measured by excitation at 360 nm and emission at 460 nm in a BMG Labtech microplate fluorimeter in 96 well microplates using 105 microliters of supernatant and 145 microliters of specific substrate at 345 micromol per liter in HBSS buffer. Microplates were incubated at 37 Celsius degrees on the reader and were kinetically read at 0, 15, 30, 45 and 60 minutes. Control wells with substrate only in HBSS buffer were included to subtract autofluorescence of substrates to both cells treated with ionomycin and to cells treated with HBSS buffer only.

| Species of origin of granzyme B | Fluorescence of supernatant from cells treated with HBSS buffer only (Basal) | Fluorescence of supernatant from cells treated with ionomycin | Signal to background |
|---|---|---|---|
| Human | 2000 | 20,000 | 10 |
| Horse | 2000 | 30,000 | 15 |
| Chimpanzee | 2000 | 20,000 | 10 |
| Rat | 2000 | 22,000 | 11 |

The above results demonstrate that granzyme B from different species may be used for the methods of the present invention. Thus, useful granule stored proteases useful for the methods of the present invention are not limited to enzymes from human origin and enzymes from many other species may be used with equal or even greater efficiency than enzymes from human origin.

Example 7

Suitable Promoters for Surface Expression of G Protein Coupled-Receptors (GPCR) Used as Exocytosis Modulators in the Methods of the Present Invention G protein coupled-receptors (GPCRs) is the main class of cell surface receptors with more than 350 different receptors and about 30 percent of currently approved drugs. Also, several GPCRs induce an intracellular calcium rise upon agonist ligand binding and thus GPCRs are very important exocytosis modulators for the methods of the present invention. But heterologous expression of GPCRs on the surface of certain cells, for example on the surface of hemopoyetic cells with professional regulated exocytosis is difficult. Over 90 percent of GPCRs do not have signal peptide and for many GPCRs there are no suitable antibodies for surface detection. Thus this example was designed to test the effect of signal peptide addition on surface expression of a model GPCR and the effect of addition of an amino terminal peptide tag for surface detection by flow cytometry of any tagged GPCR. Human Interleukin-8 receptor was selected as the model GPCR because there is available an antibody from Becton Dickinson for surface detection by flow cytometry. Vectors were developed for expression of human Interleukin-8 receptor (hIL8R) under the control of the following promoters: Moloney Leukaemia virus 5'-LTR (MoMLV5'LTR, SEQ ID NO:3), human phosphoglycerate kinase promoter and promoter for human elongation factor 1 alpha (hEF1 alpha, SEQ ID NO:1). Two vector variants were developed for each promoter: one vector variant with mouse immunoglobulin kappa signal peptide followed by a c-myc tag (EQKLISEEDLN peptide) and the entire GPCR without methionine at position 1 and one vector variant starting at methionine 1 and thus without signal peptide and without c-myc tag. All vectors had the neomycin resistance gene for selection of stable eukaryotic cells. Each vector was individually electroporated using a microporator (Digital Bio Technology, South Korea) into RBL-2H3 and after 48 hours neomycin at 500 ug/mL was added to culture for selection. After selection for about 2 weeks cells were analysed by flow cytometry (Guava Technologies, USA) with an antibody against human Interleukin-8 receptor coupled to FITC (anti-hIL8R-FITC, clone 5A2, Cat. No. 555939, Becton Dickinson, USA) and with anti-cmyc tag antibody (anti-cmyc-FITC, clone 9E10, Sigma-Aldrich, USA) for vectors that included this tag. All promoters were useful for expression of human Interleukin-8 receptor on the cell surface of RBL-2H3 cells and thus all they are useful for the methods of the present invention albeit expression from human phosphoglycerate kinase promoter (hPGK promoter) was lower than that from either hEF1 alpha promoter (hEF1 alpha promoter) or Moloney Leukaemia virus 5'-LTR promoter (MoMLV5'LTR promoter). There was no difference on the expression level of tagged and untagged GPCR and thus a universal tag and a signal peptide allow surface detection of GPCRs useful for the methods of the present invention.

Example 8

Influence of Combinations of Promoters, Signal Peptide and Glycosilation Sequence for Surface Expression in Hemopoyetic Cells with Professional Regulated Exocytosis of GPCRs Used as Exocytosis Modulators in the Methods of the Present Invention Vectors were developed for stable expression of GPCRs in hemopoyetic cells with professional regulated exocytosis under the control of the following promoters: Moloney Leukaemia virus 5'-LTR (MoMLV5'LTR, SEQ ID NO:3), human phosphoglycerate kinase promoter and human elongation factor 1 alpha promoter (hEF1 alpha, SEQ ID NO:1). All vectors had the neomycin resistance gene for selection of stable eukaryotic cells, mouse immunoglobulin kappa signal peptide followed by a c-myc tag (EQKLISEEDLN peptide) and the entire GPCR without the methionine at position 1. Each vector was individually electroporated using a microporator (Digital Bio Technology, South Korea) into RBL-2H3 and after 48 hours neomycin at 500 ug/mL was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Based on surface expression GPCRs were classified into three categories: GPCRs that were positive with all promoters tested with human interleukin-8 receptor as prototype; GPCRs that were positive with at least one of the promoters tested with human bradykinin type B1 receptor as prototype (was positive only with Moloney Leukaemia virus 5'-LTR promoter) and GPCRs that were negative with all promoters tested with human HTR1B receptor as prototype. Thus, new vectors were developed with human HTR1B receptor as a prototype of a receptor that is difficult to be expressed into hemopoyetic cells like RBL-2H3. Vectors were developed for stable expression of human HTR1B in RBL-2H3 cells with professional regulated exocytosis under the control of the following promoters: Moloney Leukaemia virus 5'-LTR (MoMLV5'LTR, SEQ ID NO:3), human phosphoglycerate kinase promoter and human elongation factor 1 alpha promoter (hEF1 alpha, SEQ ID NO:1). All vectors had the neomycin resistance gene for selection of stable eukaryotic cells, mouse immunoglobulin kappa signal peptide followed by a c-myc tag (EQKLISEEDLN peptide), a glycosilation sequence derived from a viral GPCR (VGS, SEQ ID NO:4) and the entire human HTR1B without the methionine at position 1. Such glycosilation sequence was included to test if the limiting step for surface expression is the export from endoplasmic reticulum which is regulated by post-translational modifications of proteins such as glycosilation. Each vector was individually electroporated using a microporator (Digital Bio Technology, South Korea) into RBL-2H3 and after 48 hours neomycin at 500 ug/mL was added to culture for selection. After selection for about 2 weeks cells were analysed by flow cytometry (Guava Technologies, USA) with anti-cmyc tag antibody (anti-cmyc-FITC, clone 9E10, Sigma-Aldrich, USA) for surface expression. Results were expressed as percentage of positive cells after subtraction of values from non transfected RBL-2H3 cells incubated with the same anti-cmyc tag antibody. A percentage of less than 2 percent was indicated as such and was considered negative as isolation of such positive cells by MACS was unsuccessful (data not shown). For positive cells mean fluorescence intensity (MFI) was taken as a marker of surface receptor density on the surface of positive cells. Results are shown in the next table:

| Promoter | Glycosilation | Percentaje of positive cell after selection | Mean fluorescence intensity of positive cell (MFI) |
|---|---|---|---|
| hPGK promoter | No VGS | <2 | — |
| hPGK promoter | Yes | 5.6 | 49.2 |
| hEF1alpha promoter | No VGS | <2 | — |
| hEF1alpha promoter | Yes | 10 | 56.9 |
| MoMLV5'LTR promoter | No VGS | <2 | — |
| MoMLV5'LTR promoter | Yes | 13.7 | 40.3 |
| RSV promoter | No VGS | 5 | 29.3 |
| RSV promoter | Yes | 5.6 | 82.4 |

Thus for HTR1B the inclusion of a glycosilation sequence in the vector to increase surface expression was positive with all promoters tested. Curiously, for a new promoter tested for expression of HTR1B the inclusion of a glycosilation sequence does not improved the percentage of positive cells but the MFI of positive cells was increased 2.8 fold. When vectors were developed for new GPCR including the VGS and either hEF1 alpha promoter or MoMLV-5'LTR promoter and stably transfected vectors with VGS performed always equal or better than their VGS negative counterparts. Such GPCR tested to date included: BDKRB1, AGTR1, CX3CR1, GR 4, AVPR2, DRD1, DRD2, EDNRB, TACR3, ADORA3, HTR1B, CHRM2, IL8RA, NPY1 R, ADRA2A, ADRAB2, CCKBR, SSTR2, MC1 R, BB2R and CHHR1 (data not shown). The same results were also true in other hemopoyetic cells like 32D and P815 cells and results shown for HTR1 B in RBL-2H3 are representative of the effect of a glycosilation sequence on surface expression of all tested GPCRs in several hemopoyetic cells lines. Thus, the above results indicate that the addition of a glycosilation sequence to a GPCR improves surface expression and is thus useful for the methods of the present invention.

Example 9

Development of Cells Stable Expressing Both a Granule Stored Protease Reporter and a GPCR as an Exocytosis Modulator Useful for the Methods Of the Present Invention. Regulated Exocytosis of Granule Stored Reporters Upon Ligand Binding of Exocytosis Modulator (Agonist) to Cell Surface Expressed GPCR After selection of useful cells, reporters, promoters for reporters and vectors for surface expression of GPCRs used as exocytosis modulators for the methods of the present invention a combination of all components was made in this example. Human granzyme B was selected as reporter, chimeric promoter of hCMV-MoLV5'LTR as promoter for reporter expression, RBL-2H3 as hemopoyetic cells with professional regulated exocytosis and several GPCRs as exocytosis modulators under the control of Moloney Leukaemia virus 5'-LTR (MoMLV5'LTR, SEQ ID NO:3) as promoter for expression of exocytosis modulators. All vectors for expression of exocytosis modulators had the neomycin resistance gene for selection of stable eukaryotic cells, mouse immunoglobulin kappa signal peptide followed by a c-myc tag (EQKLISEEDLN peptide), a glycosilation sequence derived from a viral GPCR (VGS, SEQ ID NO:4) and the entire human GPCR without the methionine at position 1. Vectors for expression of granzyme B had the chimeric promoter of hCMV-MoLV5'LTR-GranzymeB-IRES-NGFR with hygromycin resistance for stable transfections. Vectors for GPCR were electroporated first, cells were selected with neomycin at 500 ug/mL for about two weeks and cells were analysed by flow cytometry (Guava Technologies, USA) with anti-cmyc tag antibody (anti-cmyc-FITC, clone 9E10, Sigma-Aldrich, USA) for surface expression. Positive cells were separated by magnetic separation using anti-cmyc monoclonal antibody conjugated to biotin (Miltenyi Biotec, Germany) and streptavidin-MACS (Miltenyi Biotec, Germany). After growing positive fraction of cells was again analysed by flow cytometry with the anti-cmyc tag antibody. Positive cells were individually electroporated with the vector for expression human granzyme B using a microporator (Digital Bio Technology, South Korea) and after 48 hours hygromycin at 1500 ug/mL and neomycin at 500 ug/mL were added to culture for selection. After selection for about 2 weeks cells were analysed by flow cytometry (Guava Technologies, USA) with an antibody against NGFR coupled to FITC. Positive population where magnetically separated by MACS using anti-NGFR-MACS sup.R (Miltenyi Biotec, Germany). Sorted populations were again analysed again by flow cytometry to check both the expression of the GPCR with the anti-cmyc tag antibody and with anti-NGFR antibody to check granzyme B expression. Expression of GPCRs was detected in over 70 percent of cells isolated as positive fraction while granzyme B was positive for over 65 percent of cells. GPCRs included were: SSTR2 and CHRM2 as alpha-i coupled GPCRs; AGTR1 and bradykinin type B1 receptor (BDKRB1) as alpha-q coupled GPCRs and AVPR2 as alpha-s coupled GPCR. Ligands for the above GPCRs were purchased from Sigma-Aldrich (USA) and used at 10 uM final concentration in HBSS buffer unless otherwise stated: seglitide (for SSTR2); carbachol (for CHRM2); angiotensin (for AGTR1); kallinin (for bradykinin type B1) and arginine-vasopressin (for AVPR2). Cells were seeded the night before experiment at 100.000 cells per well of a 96-well microplate in 100 uL of complete cell culture medium. Next day cells were washed with HBSS buffer and incubated with the ligand (agonist) at 10 uM of each GPCR in 30 uL of HBSS buffer at 37 Celsius degrees for 60 minutes and after centrifugation at 400 g for 5 minutes supernatants were analysed for human granzyme B protein by a sandwich ELISA specific for human granzyme B (Ucytech, Netherlands). Controls were included with cells treated with HBSS only for basal release. Background of ELISA was 0.2. The maximal dilution factor for a positive ELISA was used to calculate the minimal number of cells for granzyme B quantification using the following data: 100.000 cells were seeded, exocytosis was made in 30 uL and in the ELISA plate 100 uL of supernatant were loaded per well. For example, if 30 uL of supernatant of ligand (agonist) treated cells are used per well of ELISA plate and the volume is completed to 100 uL then the sensitivity of such assay for such GPCR is of 100.000 cells because 100.000 cells are divided by 30 uL, multiplied by 100 uL used per well of ELISA plate and divided by a dilution factor of 3.33 as the volume is completed from 30 uL to 100 uL. A better assay is such for which a lower amount of cells is needed. The results were as follows:

| GPCR as exocytosis modulator (type) | Ligand used (agonist) | Maximal dilution of ELISA tested | Absorbance at maximal dilution of ELISA tested (1) | Sensitivity (minimal amount of cells needed) |
|---|---|---|---|---|
| SSTR2 (alpha-i coupled) | Seglitide | 2250 | 2.4 | <150 cells |
| CHRM2 (alpha-i coupled) | Carbachol | 2250 | 0.6 | <150 cells |
| AGTR1 (alpha-q coupled) | Angiotensin | 2250 | 1.8 | <150 cells |
| BDKRB1 (alpha-q coupled) | Kallinin | 2250 | 0.8 | <150 cells |
| AGTR1 (alpha-s coupled) | Arginine-vasopressin | 2250 | 0.2 | 150 cells |

(1) After subtraction of 0.2 corresponding to blank wells

The above results demonstrate that hemopoyetic cells with professional regulated exocytosis of granule stored protease reporters bearing GPCRs as exocytosis modulators could be extremely sensitive sensor for testing interactions between ligans and exocytosis modulators.

Example 10

Direct Detection of Secreted Granule Proteases with Highly Sensitive Substrates

The experiment of example 9 demonstrated that sensors based on exocytosis of granule stored proteins can be extremely sensitive (enzyme secreted from less than 100 cells may be readily detected by ELISA) but in experiments of example 6 for detection of enzymatic activity about 100.000 cells were needed for a signal to background ratio of 10. Thus, the factor that limited the assay sensitivity in homogeneous assays was the combination of granule stored proteases with AMC-coupled peptides. It is known in the state of the art that amino acids at both sides of cleavage site are primary determinants of both cleavage specificity and efficiency. Thus, in order to increase sensitivity of detection of enzymatic activity from secreted proteases, peptide substrates with amino acids at both sides of cleavage sites may be synthesized. As an alternative, protease amplification cascades with zymogens may be used for signal amplification. In this example a substrate based on FRET were custom designed to test if either a different detection technology, that is FRET versus fluorescence of released AMC, or a better cleavage sequence due to existence of amino acids at both sides of cleavage site improves detection of enzymatic activity of granule released protease. Human granzyme B was used as a model enzyme. Substrates for detection of secreted human granzyme B were: IEPD-AMC which was used at 200 uM final concentration and read at 505 nm after excitation at 400 nm and FAM-Ser-Ile-Glu-Pro-Asp-Ser-Gly-Ser-TAMRA (FAM-SIEPDSGS-TAMRA) which was custom synthesized by a peptide supplier. Cleavage of FAM-TAMRA labelled peptide was detected by fluorescence using excitation at 485 nm and emission at 535 nm and labelled peptide at 1 uM final concentration.

For each substrate the exocytosis of 50.000, 25.000, 12.500, 6.250, 3.125, 1560, 780 and 390 cells was analysed. Cells were seeded the night before experiment at the above densities in 96 well plates using 100 uL of complete cell culture medium per well. The day of experiment cells were washed with HBSS buffer and exocytosis was initiated by addition of ionomycin at 10 uM final concentration in HBSS buffer and incubation for 60 minutes at 37 Celsius degrees. Controls of cells treated with HBSS buffer only were included for basal release determination. Five replicas of each cell density for each substrate were seeded. Supernatant from cells were centrifuged at 400 g for 5 minutes and used for fluorescence determination in 96 well plates. Released AMC was measured by excitation at 360 nm and emission at 460 nm in a BMG Labtech microplate fluorimeter in 96 well microplates while released FAM was measured by excitation at 485 nm and emission at 535 nm in the same reader. Microplates were incubated at 37 Celsius degrees on the reader and were kinetically read at 0, 15, 30, 45 and 60 minutes. Control wells with substrate only in HBSS buffer were included to subtract autofluorescence of substrates to both cells treated with ionomycin and to cells treated with HBSS buffer only. An arbitrary signal to background of about two was selected as sensitivity. Results were as follows: for IEPD-AMC sensitivity was of 25.000 cells that produced a signal to background of 2 while for FAM-TAMRA peptide sensitivity was between 390 and 780 cells as 780 cells produced a signal to background of 3 while 390 produced a signal to background below the arbitrary limit of 2. Selecting the sensitivity as 780 cells the FAM-TAMRA peptide is more than 30 times more sensitive for detection of granzyme B than IEPD-AMC peptide. Thus, this example illustrates that selection of highly sensitive protease substrates like FRET peptides is useful for the methods of the present invention.

Example 11

Development of Zymogens for an Amplification Cascade

The last example demonstrated that highly sensitive substrates are useful for sensitive detection of granule stored protease reporters when they are released, thus this example was designed to demonstrate that another way of sensitive signal amplification is the use of a proteolytic cascade. As a model we selected human granzyme B. A human granzyme B activated-zymogen was developed from human native unmodified procaspase-3 (huCasp3) and from a mutated human procaspase-3 (mut-huCasp3) where the amino acids from 172 to 179 has been changed from Ile-Glu-Thr-Asp-Ser-Gly-Val-Asp to Ile-Glu-Pro-Asp-Val-Leu-Met-Glu, that is Threonine at 174 has been mutated to Proline because IEPD is a better granzyme B substrate than IETD and serine at 176 has been mutated to valine, glycine at 177 has been mutated to leucine, valine at 178 has been mutated to methionine and aspartic acid at 179 has been mutated to glutamic acid in order to both improve cleavage efficiency by human granzyme B and to reduce autoactivation of procaspase-3. cDNA from both variants of human pro-caspase-3 comprising amino acids from Serine at 29 to Aspartic acid at 192 were cloned into pET43a+ vector from Novagen. After sequencing expression vectors were transformed into BL21 DE3pLys *E. coli* strain for protein expression. Each protein was cloned with a polyhistidine tag at C-terminal end for purification. Human native procaspase-3 (huCasp3) was induced for only 30 minutes to prevent autoactivation, while mutated pro-caspase-3 (mut-huCasp3) was induced both for 30 minutes and for 2 hours. DEVD-AMC substrate was used for detection of active caspase-3 with excitation at 360 nm and emission at 460 nm. A supernatant equivalent to 15.000 RBL-2H3 stably transfected with human granzyme B treated with 10 uM ionomycin for 60 minutes was used for zymogen activation. Human granzyme B activity of such supernatant when measured with IEPD-AMC produced a signal to background of 2.6 after incubation for 60 minutes at 37 Celsius degrees using a supernatant equivalent to 25.000 cells. Background of fluorescence of DEVD-AMC substrate was 2775 and was subtracted from both granzyme B treated caspase-3 and non-granzyme B treated caspase-3 (caspase-3 only) used as control and all samples were tested by triplicate. Results were as follows:

| Human Caspase-3 | Fluorescecen of Caspase-3 only | Fluorescence of caspase-3 treated with granzyme B | Signal to Brackgroun (S/B) |
|---|---|---|---|
| Native (unmodified) huCasp-3 | 15775 | 43548 | 2.8 |
| Mut-huCasp-3 (Mutated at 172 to 179) | 588 | 45472 | 77 |

The above results demonstrate that human procaspase-3 is useful for detection of granule secreted granzyme B and is about 1.7 times more sensitive than direct detection of secreted granzyme B with substrate IEPD-AMC as the signal to background using the supernatant equivalent to 15.000 cells and pro-caspase-3 is the same than direct detection of human granzyme B using the supernatant equivalent to 25.000 cells. While mutation of procaspase-3 does not improve cleavage by human granzyme B as the fluorescence is about the same (45472 vs 43548), the basal autoactivation of mutated human procaspase-3 was 27 times lower than that of human native procaspase-3. The signal to background ratio of mutated human procaspase-3 was 77, that is, about 27 times higher than that of native human procaspase-3. Using the supernatant equivalent to 5.000 cells and a 384 well plate the signal to background was higher than 20, thus mutated human procaspase-3 allow the development of a homogeneous cells based sensor useful for the methods of the present invention. In addition, human mutated procaspase-3 can be expressed to about 10 mg/L of *E. coli* culture (about 10 times more protein than native procaspase-3 expressed for only 30 minutes to prevent autoactivation), has no basal activity even after 120 minutes incubation at 37° C. in optimal reaction conditions and can be stored for at least 6 months at −20 Celsius degrees without autoactivation. Thus, zymogens with a high zymogenicity index and low basal activity are useful for both sensitivity improvement and for a high signal to background ratio that benefit the cell based sensors of the present invention.

Example 12

Optimization of Assay Conditions: Exocytosis Time

An experiment was designed to optimize assay conditions such as: exocytosis time, number of steps needed for assay and uses of cells in suspension. Cells developed in example #9 expressing both a GPCR and human granzyme B were used in this example for optimization of exocytosis time. GPCRs included were CHRM2 (an alpha-i coupled GPCR) and bradykinin type B1 receptor (an alpha-q coupled GPCR). Carbachol and kallinin from Sigma-Aldrich (USA) were used as ligands for CHRM2 and bradykinin type B1 receptor, respectively and used at 10 uM final concentration in HBSS buffer. Cells were seeded the night before experiment at 20.000 cells per well of a 96-well microplate in 100 uL of complete cell culture medium. Next day cells were washed with HBSS buffer and incubated with the ligand (agonist) at 10 uM of each GPCR in 30 uL of HBSS buffer at 37 Celsius degrees for 5, 15, 30 or 60 minutes and after centrifugation at 400 g for 5 minutes supernatants were analysed for human granzyme B activity using FAM-SIEPDSGS-TAMRA at 1 uM final concentration as the human granzyme B substrate. Released FAM was measured by excitation at 485 nm and emission at 535 nm in a BMG Labtech microplate fluorimeter in 96 well microplates. Microplates were incubated at 37 Celsius degrees on the reader and were kinetically read at 0, 15, 30, 45 and 60 minutes. Control wells with substrate only in HBSS buffer were included to subtract autofluorescence of substrates to both cells treated with ligands and to cells treated with HBSS buffer only. For both bradykinin type B1 receptor and for CHRM2 it was found that exocytosis is over than 90% of maximal at 5 minutes and the signal to background (S/B) is about 20-22 if medium is taken at 5 to 15 minutes; S/B is about 15-17 if medium is taken at 30 minutes and S/B is about 8-10 if medium is taken at 60 minutes. The signal to background is lower at longer exocytosis times due to the higher increase in basal release than the increase in specific signal after the first 5 to 15 minutes. Thus, any exocytosis time from probably less than 5 minutes to at least 60 minutes may be used for the methods of the present invention but longer exocytosis times produce a sensor with a lower signal to background, exocytosis is nearly complete at 5 minutes and signal to background is good for a robust sensor. This example also suggests that due to low exocytosis time it is possible to mix a cell impermeable reporter substrate directly with cells for a mix and read assay to increase throughput.

Example 13

Optimization of Assay Conditions: Number of Steps Needed for Assay

This experiment was designed to test how many steps are needed for an assay with the cell based sensor, in particular if a washing step is needed before assay. As the RBL-2H3 is an adherent cell line at least one step of aspiration of cell culture medium is needed. If all cell culture medium is aspirated then cells should become dry and eventually die in particular if there is a time interval between aspiration and addition of compounds to test for exocytosis. For this reason an additional treatment was included were not all cell culture medium is aspirated. But if not all the cell culture medium is aspirated then some of the reporter secreted by cells after overnight culture contributes to basal exocytosis. CHRM2 and granzyme B expressing cells from example #12 were used in this experiment but cells were seeded 16 hours before experiment at 5.000 cells per well of a 384 well plate with black walls in 20 uL of culture medium. Before experiment three treatments were made: (1) discarding all the 20 uL of medium without washing; (2) discarding only 15 uL of cell culture medium and (3) discarding only 15 uL of cell culture medium and washing of the cells using 75 uL of Hanks Balanced Salt Solution (HBSS) containing 0.1% BSA and aspiration of 75 uL of washing buffer. Exocytosis was made in HBSS containing carbachol (a CHRM2 receptor agonist) at 10 uM final concentration. For basal exocytosis, HBSS without carbachol was included. Wells for both basal and agonist induced secretion included FAM-SIEPDSGS-TAMRA at 1 uM final concentration as human granzyme B substrate for both exocytosis and activity determination in the same well. Plates were incubated at 37° C. in the fluorescence reader and read at 0, 15, 30, 45 and 60 minutes. Results were as follows: (a) when all the culture medium is aspirated from the wells there is no need to make an additional washing step of the cells as the granzyme B activity corresponding to basal exocytosis in the wells without carbachol is low and signal to background is from 18 to 20 in 30 minutes; (b) when only 15 uL of cell culture medium is aspirated from the wells basal activity reduces signal to background to 8-10 in 30 minutes; when only 15 uL of cell culture medium is aspirated and a washing step with 75 uL of HBSS is included then signal to background is similar to the treatment were all the cell culture medium is aspirated. Thus, if all the cell culture medium is aspirated then a washing step is not needed and just a single step before experiment is needed (discard of cell culture medium). If only a portion of cell culture medium is aspirated then a washing step is needed and two steps are needed before experiment (discard of cell culture medium and a washing step with an addition-discard of washing buffer). Thus, a good sensor could be developed by either aspiration of all the cell culture medium or by aspiration of a fixed amount and making an additional washing step.

Example 14

Development of a Sensor to Measure More than One Reaction Per Well

Figure 5:
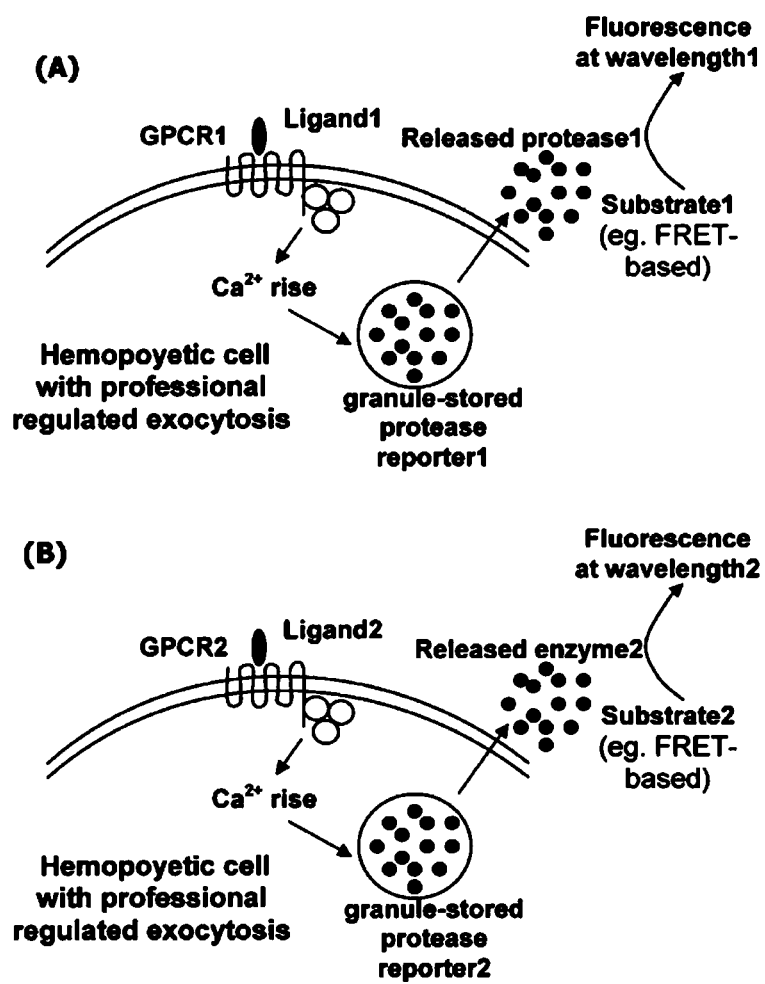
FIG. 5. Drawing of duplex assay made with methods described in the present invention. Two different cell lines (A) and (B), are mixed in the same reaction vessel. Cell line A express a combination of GPCR1 (exocytosis modulator)-granule stored protease reporterl. The GPCR1 has Ligandl as agonist while Protease reporterl cleaves the Substratel (for example a FRET based substrate) that is read at wavelength"!. Cell line B express a combination of GPCR2 (exocytosis modulator)-granule stored protease reporter2. The GPCR2 has Ligand2 as agonist while Protease reporter2 cleaves the Substrate2 (for example a FRET based substrate) that is read at wavelength2. Treatment of a mix of cells A and B with a mix of Ligandl and Ligand2 of the GPCR1 and GPCR2 induces release of granule stored proteasesl and 2 and the increase in fluorescence at wavelengths 1 and 2 could be determined.

This example was designed to illustrate that sensors of the present invention may be used to develop multiplex reactions, that is, to measure more than one reaction in the same reaction vessel. The principle of multiplex reactions is illustrated in FIG. 5. RBL2H3 cells were stably transfected with a pair of a GPCR as exocytosis modulator and a granzyme as a granule stored reporter as described in example 9. Combinations included were: hIL8 receptor (hIL8RA) and human granzyme A (Sensor A) and CHRM2 and granzyme B expressing cells of example #12 (Sensor B). Human IL8 was used as agonist of hIl_8R while carbachol was used as CHRM2 agonist. Granzyme A FRET based substrate was: FAM-EVANRSVSEK-TAMRA while granzyme B FRET based substrate was FAM-SIEPDSGS-TAMRA. As both substrates uses the same pair of fluorophore (FAM) and quencher (TAMRA) only one substrate could be added to reaction vessel for specific detection at 535 nm after excitation at 485 nm. In a first experiment it was found that maximal enzymatic activity of human granzyme A secreted by sensor A upon IL8 treatment was about 40 percent of granzyme B activity secreted by sensor B upon carbachol treatment (data not shown), thus 12500 cells of sensor A were mixed with 5000 cells of sensor B. Each well was tested by triplicate. Sensors, agonists and substrates were mixed in a total volume of 20 uL of HBSS in a black walled 384 well microplate and the microplate was incubated at 37 Celsius degrees in a BMG-Labtech microplate fluorimeter and read at 0, 15, 30, 45 and 60 minutes. Signal to background after 30 minutes of incubation at 37 Celsius degrees are summarized in the following table. Condition 1 was selected as signal to background of 1 for sensor A and condition 6 was selected as signal to background of 1 for sensor B because there are different basal releases due to difference in the total number of cells in assay. Conditions 5 and 10 illustrates that more than one sensor may be combined in the same reaction well to produce a multiplex biosensor with good signal to background ratio at each channel. Thus, results demonstrate that at least two sensors may be mixed in the same reaction vessel to produce a multiplex assay provided granule released reporters do not have interference with each other. This example also demonstrates that sensors with different maximal activities could be mixed in different proportions to produce a sensor with equivalent signal in each channel.

| Condition | Cells of Sensor A | IL8 (uM) | Granzyme A substrate (uM) | Cells of Sensor B | Carbachol (uM) | Granzyme B substrate (uM) | Signal to background at 30 min |
|---|---|---|---|---|---|---|---|
| 1 | 12500 | 0 | 1 | 0 | 0 | 0 | 1 |
| 2 | 12500 | 10 | 1 | 0 | 0 | 0 | 16 |
| 3 | 12500 | 0 | 1 | 5000 | 0 | 0 | 0.83 |
| 4 | 12500 | 0 | 1 | 5000 | 10 | 0 | 0.78 |
| 5 | 12500 | 10 | 1 | 5000 | 10 | 0 | 12.5 |
| 6 | 0 | 0 | 0 | 5000 | 0 | 1 | 1 |
| 7 | 0 | 0 | 0 | 5000 | 10 | 1 | 20 |
| 8 | 12500 | 0 | 0 | 5000 | 0 | 1 | 0.97 |
| 9 | 12500 | 10 | 0 | 5000 | 0 | 1 | 0.95 |
| 10 | 12500 | 10 | 0 | 5000 | 10 | 1 | 20 |

Example 15

Development of a Sensor Useful for Tyrosine Kinase Surface Receptors

EGFR surface receptor was cloned into a pcDNA3.1 vector modified to express proteins under the control of hCMV-MoMLV-5'LTR chimeric promoter with a signal peptide and a c-myc tag for surface detection and or separation. Such EGF receptor was stably transfected into RBL-2H3 cells and such cells were stably transfected with human granzyme B (exocytosis reporter) under the control of hCMV-MoMLV-5'LTR chimeric promoter. Cells in suspension were used at 5.000 cells per well of a 384 well plate in 20 uL total volume. Wells for both basal and agonist induced secretion included FAM-SIEPDSGS-TAMRA at 1 uM final concentration as human granzyme B substrate for both exocytosis and activity determination in the same well. Agonist of the receptor was Epidermal Growth Factor (EGF) and was used at 10 uM final concentration. Plates were incubated at 37° C. in the fluorescence reader and read at 0, 15, 30, 45 and 60 minutes. Results were as follows: EGF treatment induced strong specific release of human granzyme B when compared with non EGF treated cells. Signal to background was 15 after 45 minutes. The above results demonstrate that tyrosine kinase receptors could be used as exocytosis modulators in the methods of the present invention and thus that sensors of the present invention may be applied to test interaction between tyrosine kinase receptors and their ligands.

Example 16

Uses of the Sensor for Testing IgE-Allergen Interactions

This example describes the use of the sensor for testing modulators of mast cells granule exocytosis widely used to find novel anti-allergic compounds as illustrated in FIG. 1. RBL2H3 were stably transfected with human granzyme B under the control of hCMV-MoLV5'LTR chimeric promoter as described in example 3. A mouse IgE monoclonal antibody against trinitrophenyl hapten was purified from IgELb4 hybridoma purchased from ATCC (TIB-141). TNP-N-hydroxysuccinimide esther was purchased from Biosearch Technologies Inc and conjugated to bovine serum albumin (BSA) using a standard protocol. Conjugation was determined at pH 7.0 by measuring TNP absorbance at 348 nm using 15400 units per mol per 10 mm light pass length as the extinction coefficient of TNP. Molar ratio of TNP to BSA in the TNP-BSA conjugate was calculated assuming the molecular weight of BSA is 60000. Sensor cells were cultivated as adherent cells for 48 hours in 6 well plates and then washed with HBSS and harvested by pippeting. 500.000 cells were labelled with anti-TNP IgE at 1 ug/ml_in HBSS for 60 minutes at 37 Celsius degrees, washed with 10 mL of HBSS, centrifuged and pellet was resuspended in 1 mL of HBSS. In a black wall 384 well plate 10 uL of serial dilutions of TNP-BSA in HBSS were added each containing the FRET-based granzyme B substrate FAM-Ser-Ile-Glu-Pro-Asp-Ser-Gly-Ser-TAMRA (FAM-SIEPDSGS-TAMRA) at 1 uM final concentration whose cleavage was detected by fluorescence using excitation at 485 nm and emission at 535 nm. Dilutions of TNP-BSA tested were: 1 ug/mL, 1 ng/mL, 1 pg/mL and 1 fg/mL. To each well 10 uL (5000 cells) of anti-TNP IgE labelled cells were added and plates were incubated at 37 Celsius degrees in a BMG-Labtech microplate fluorimeter. Microplate was read at 0, 15, 30, 45 and 60 minutes. The following controls were included: (1) wells with anti-TNP IgE labelled cells plus granzyme B substrate but without TNP-BSA; (2) wells with non-labelled cells plus granzyme B substrate and TNP-BSA at 1 ug/ml_; (3) wells with granzyme B substrate and TNP-BSA at 1 ug/ml_but no cells. Each well was included by triplicate. Results after 30 minutes of incubation at 37 Celsius degrees are summarized in the following table:

| RBL2H3-hGB cells | Anti-TNP IgE | Amount of TNP-BSA | FRET-based granzyme B substrate | Fluorescence after 30 minutes at 37° C. |
|---|---|---|---|---|
| 5000 | Yes | 1 ug/mL | 1 uM | 30942 |
| 5000 | Yes | 1 ng/mL | 1 uM | 34556 |
| 5000 | Yes | 1 pg/mL | 1 uM | 35884 |
| 5000 | Yes | 1 fg/mL | 1 uM | 29826 |
| 5000 | Yes | 0 | 1 uM | 2872 |
| 5000 | No | 1 ug/mL | 1 uM | 2935 |
| 0 | Yes | 1 ug/mL | 1 uM | 1535 |

The above results indicate that the sensor developed in the methods of the present invention is highly sensitive for detection of allergens like the TNP-BSA model allergen used in this example as the signal is saturated even to 1 fg/mL. By further diluting TNP-BSA it was found that the limit of detection for TNP-BSA was 0.1 ag/mL, that is 10sup-19 g/mL that probably makes this sensor the most sensitive developed to date (data not shown). Thus, sensor of the present invention may be used for both highly sensitive allergen detection and for testing modulators of mast cells granule exocytosis widely used to find novel anti-allergic compounds.

The invention claimed is:

1. a cell based sensor that comprises:
 a) a hemopoyetic cell line with professional regulated exocytosis of secretory granules;
 b) granzyme B as a protease reporter transfected into the cell line of (a) that is stored into the secretory granules of such cell line;
 c) a transfected heterologous surface receptor used as a modulator of regulated exocytosis of the secretory granules of the cell line of (a); and
 d) a specific substrate for detection of the secreted granule stored protease reporter or means for immunologically detecting the protease reporter.

2. The cell based sensor of claim 1 wherein the cell line with professional regulated exocytosis of secretory granules is a hemopoyetic cell line and/or their progeny selected from the group consisting of myeloid cell lines and lymphoid cell lines, wherein the myeloid cell lines comprise monocytes, macrophages, neutrophils, basophils, eosinphils, mast cells, erythrocytes, megakaryocytes, platelets or dendritic cells, and wherein the lymphoid cell lines comprise T-cells, B-cells, or NK-cells.

3. The cell based sensor of claims 1, wherein the cells are selected from the group consisting of the rat basophilic leukemia cell line RBL-2H3, the mouse bone marrow hemopoyetic cell line 32D, the natural killer cell line human NK92 cell line, the natural killer cell line human YT cell line and the mouse mast cell mouse MC/9 cell line.

4. The cell based sensor of claim 1, wherein the surface receptor used a exocytosis modulator is a polypeptide that when activated or inhibited induces a change in the levels of intracellular calcium, cAMP, diacylglycerol (DAG) phospholipids or ATP that in turn regulate or modulate calcium triggered exocytosis.

5. The cell based sensor of claim 1, wherein the surface receptor is a G-protein coupled receptor (GPCR).

6. A kit comprising the cell based sensor of claim 1 for testing if a compound modulates exocytosis.

* * * * *